United States Patent
Hayashi et al.

(10) Patent No.: US 11,594,683 B2
(45) Date of Patent: Feb. 28, 2023

(54) ORGANIC ELECTROLUMINESCENT DEVICE

(71) Applicant: Hodogaya Chemical Co., Ltd., Tokyo (JP)

(72) Inventors: Shuichi Hayashi, Tokyo (JP); Naoaki Kabasawa, Tokyo (JP); Takeshi Yamamoto, Tokyo (JP); Hideyoshi Kitahara, Tokyo (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 405 days.

(21) Appl. No.: 15/771,194

(22) PCT Filed: Oct. 26, 2016

(86) PCT No.: PCT/JP2016/081685
§ 371 (c)(1),
(2) Date: Apr. 27, 2018

(87) PCT Pub. No.: WO2017/073594
PCT Pub. Date: May 4, 2017

(65) Prior Publication Data
US 2018/0331298 A1   Nov. 15, 2018

(30) Foreign Application Priority Data
Oct. 29, 2015   (JP) .............................. JP2015-212681

(51) Int. Cl.
*H01L 51/00* (2006.01)
*C07C 211/54* (2006.01)
(Continued)

(52) U.S. Cl.
CPC ........ *H01L 51/0059* (2013.01); *C07C 211/54* (2013.01); *C07C 211/58* (2013.01);
(Continued)

(58) Field of Classification Search
CPC ............ H01L 51/0059; H01L 51/5048; H01L 51/5056; H01L 51/5064
See application file for complete search history.

(56) References Cited

U.S. PATENT DOCUMENTS

2004/0023060 A1   2/2004   Kim et al.
2004/0170863 A1   9/2004   Kim et al.
(Continued)

FOREIGN PATENT DOCUMENTS

JP   2002-356462 A     12/2002
JP   2002356462 A  *  12/2002
(Continued)

OTHER PUBLICATIONS

English machine translation of Yokoyama et al. (WO 2014/129201 A1) provided by the EPO website. 2020. (Year: 2020).*
(Continued)

*Primary Examiner* — Daniel P Malley, Jr.
(74) *Attorney, Agent, or Firm* — Locke Lord LLP; James E. Armstrong, IV; Nicholas J. DiCeglie, Jr.

(57) ABSTRACT

A material for an organic electroluminescent device that is excellent in hole injection and transport abilities, electron blocking ability, stability in a thin film state, and durability is provided as a material for an organic electroluminescent device having high efficiency and high durability. Further, an organic electroluminescent device having low driving voltage, high efficiency, and a long lifetime is provided by combining the material with various materials for an organic EL device that is excellent in hole and electron injection and transport abilities, electron blocking ability, thin film stability, and durability, in such a manner that the characteristics of the materials can be effectively exhibited. An organic electroluminescent device comprising at least an anode, a
(Continued)

← 9 CATHODE
← 8 ELECTRON INJECTION LAYER
← 7 ELECTRON TRANSPORT LAYER
← 6 LIGHT EMITTING LAYER
← 5 SECOND HOLE TRANSPORT LAYER
← 4 FIRST HOLE TRANSPORT LAYER
← 3 HOLE INJECTION LAYER
← 2 TRANSPARENT ANODE
← 1 GLASS SUBSTRATE hole transport layer, a light emitting layer, an electron transport layer, and a cathode in this order, wherein the hole transport layer comprises an arylamine compound of the following general formula (1).

[Chemical Formula 1]

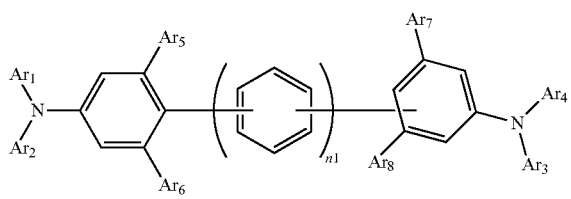

(1)

11 Claims, 1 Drawing Sheet

(51) Int. Cl.
H01L 51/50 (2006.01)
C09K 11/06 (2006.01)
C07D 209/86 (2006.01)
C07C 211/61 (2006.01)
C07D 401/10 (2006.01)
C07C 211/58 (2006.01)
C07D 213/38 (2006.01)
H01L 51/52 (2006.01)

(52) U.S. Cl.
CPC .......... C07C 211/61 (2013.01); C07D 209/86 (2013.01); C07D 213/38 (2013.01); C07D 401/10 (2013.01); C09K 11/06 (2013.01); H01L 51/0054 (2013.01); H01L 51/50 (2013.01); H01L 51/5024 (2013.01); H01L 51/5092 (2013.01); H01L 51/5206 (2013.01); H01L 51/5221 (2013.01); C07C 2603/18 (2017.05); H01L 51/5056 (2013.01); H01L 51/5072 (2013.01)

(56) References Cited

U.S. PATENT DOCUMENTS

| | | | | |
|---|---|---|---|---|
| 2005/0236976 | A1* | 10/2005 | Leung | H01L 51/0059 313/504 |
| 2012/0181922 | A1 | 7/2012 | Kawamura et al. | |
| 2015/0034923 | A1* | 2/2015 | Kim | H01L 27/3209 257/40 |
| 2015/0380657 | A1* | 12/2015 | Yokoyama | C07D 471/04 257/40 |
| 2016/0163982 | A1 | 6/2016 | Ishihara et al. | |

FOREIGN PATENT DOCUMENTS

| | | | |
|---|---|---|---|
| JP | 2004-529937 A | | 9/2004 |
| JP | 2007-108308 A | | 4/2007 |
| JP | 2007-164037 A | | 6/2007 |
| JP | 2010-202638 A | | 9/2010 |
| JP | 2011-222831 A | | 11/2011 |
| JP | 2013-191649 A | | 9/2013 |
| JP | 2016-111099 A | | 6/2016 |
| KR | 10-2010-0123172 A | | 11/2010 |
| KR | 10-2011-0057078 A | | 5/2011 |
| KR | 10-2011-0084797 A | | 7/2011 |
| KR | 10-2011-0084798 A | | 7/2011 |
| KR | 20110084797 A | * | 7/2011 |
| KR | 10-2015-0007476 A | | 1/2015 |
| WO | 2007/043484 A1 | | 4/2007 |
| WO | 2014/129201 A1 | | 8/2014 |
| WO | WO-2014129201 A1 | * | 8/2014 ........... C07C 211/54 |

OTHER PUBLICATIONS

English machine translation of Park et al. (KR-20110084797-A) provided by the EPO website, 2021, All Pages. (Year: 2021).*
STN structure search for 15771194 conducted by the examiner, 2021, all pages. (Year: 2021).*
STN Structure search conducted by the Examiner for U.S. Appl. No. 15/771,194—All Pages, dated May 27, 2021. (Year: 2021).*
English machine translation of Kita (JP-2002356462-A) provided by the EPO website, All Pages, 2022. (Year: 2022).*
STN structure search conducted by the Examiner for U.S. Appl. No. 15/771,194, All Pages, 2022. (Year: 2022).*
English machine translation of Yokoyama (WO-2014129201-A1) provided by the EPO website, All Pages, 2022. (Year: 2022).*
STN structure search conducted by the Examiner dated Oct. 19, 2022, All Pages. (Year: 2022).*
International Search Report dated Jan. 24, 2017, issued for PCT/JP2016/081685.

* cited by examiner

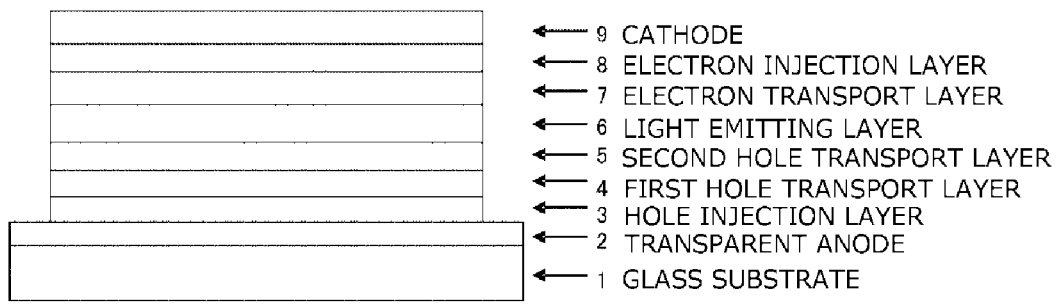

ORGANIC ELECTROLUMINESCENT DEVICE

TECHNICAL FIELD

The present invention relates to an organic electroluminescent device which is a preferred self-luminous device for various display devices. Specifically, this invention relates to specific arylamine compounds, and organic electroluminescent devices (hereinafter referred to as organic EL devices) using specific arylamine compounds (and compounds having a pyrimidine ring structure having the particular structure).

BACKGROUND ART

The organic EL device is a self-luminous device and has been actively studied for their brighter, superior visibility and the ability to display clearer images in comparison with liquid crystal devices.

In 1987, C. W. Tang and colleagues at Eastman Kodak developed a laminated structure device using materials assigned with different roles, realizing practical applications of an organic EL device with organic materials. These researchers laminated an electron-transporting phosphor and a hole-transporting organic substance, and injected both charges into a phosphor layer to cause emission in order to obtain a high luminance of 1,000 cd/m$^2$ or more at a voltage of 10 V or less (refer to PTLs 1 and 2, for example).

To date, various improvements have been made for practical applications of the organic EL device. Various roles of the laminated structure are further subdivided to provide an electroluminescence device that includes an anode, a hole injection layer, a hole transport layer, a light emitting layer, an electron transport layer, an electron injection layer, and a cathode successively formed on a substrate, and high efficiency and durability have been achieved by the electroluminescence device (refer to NPL 1, for example).

Further, there have been attempts to use triplet excitons for further improvements of luminous efficiency, and the use of a phosphorescence-emitting compound has been examined (refer to NPL 2, for example).

Devices that use light emission caused by thermally activated delayed fluorescence (TADF) have also been developed. In 2011, Adachi et al. at Kyushu University, National University Corporation realized 5.3% external quantum efficiency with a device using a thermally activated delayed fluorescent material (refer to NPL 3, for example).

The light emitting layer can be also fabricated by doping a charge-transporting compound generally called a host material, with a fluorescent compound, a phosphorescence-emitting compound, or a delayed fluorescent-emitting material. As described in the NPL, the selection of organic materials in an organic EL device greatly influences various device characteristics such as efficiency and durability (refer to NPL 2, for example).

In an organic EL device, charges injected from both electrodes recombine in a light emitting layer to cause emission. What is important here is how efficiently the hole and electron charges are transferred to the light emitting layer in order to form a device having excellent carrier balance. The probability of hole-electron recombination can be improved by improving hole injectability and electron blocking performance of blocking injected electrons from the cathode, and high luminous efficiency can be obtained by confining excitons generated in the light emitting layer. The role of a hole transport material is therefore important, and there is a need for a hole transport material that has high hole injectability, high hole mobility, high electron blocking performance, and high durability to electrons.

Heat resistance and amorphousness of the materials are also important with respect to the lifetime of the device. The materials with low heat resistance cause thermal decomposition even at a low temperature by heat generated during the drive of the device, which leads to the deterioration of the materials. The materials with low amorphousness cause crystallization of a thin film even in a short time and lead to the deterioration of the device. The materials in use are therefore required to have characteristics of high heat resistance and satisfactory amorphousness.

N,N'-diphenyl-N,N'-di(α-naphthyl)benzidine (NPD) and various aromatic amine derivatives are known as the hole transport materials used for the organic EL device (refer to PTLs 1 and 2, for example). Although NPD has desirable hole transportability, its glass transition point (Tg), which is an index of heat resistance, is as low as 96° C., which causes the degradation of device characteristics by crystallization under a high-temperature condition (refer to NPL 4, for example). The aromatic amine derivatives described in the PTLs include a compound known to have an excellent hole mobility of 10$^{-3}$ cm$^2$/Vs or higher (refer to PTLs 1 and 2, for example). However, since the compound is insufficient in terms of electron blocking performance, some of the electrons pass through the light emitting layer, and improvements in luminous efficiency cannot be expected. For such a reason, a material with higher electron blocking performance, a more stable thin-film state and higher heat resistance is needed for higher efficiency. Although an aromatic amine derivative having high durability is reported (refer to PTL 3, for example), the derivative is used as a charge transporting material used in an electrophotographic photoconductor, and there is no example of using the derivative in the organic EL device.

Arylamine compounds having a substituted carbazole structure are proposed as compounds improved in the characteristics such as heat resistance and hole injectability (refer to PTLs 4 and 5, for example). However, while the devices using these compounds for the hole injection layer or the hole transport layer have been improved in heat resistance, luminous efficiency and the like, the improvements are still insufficient. Further lower driving voltage and higher luminous efficiency are therefore needed.

In order to improve characteristics of the organic EL device and to improve the yield of the device production, it has been desired to develop a device having high luminous efficiency, low driving voltage and a long lifetime by using in combination the materials that excel in hole and electron injection/transport performances, stability as a thin film and durability, permitting holes and electrons to be highly efficiently recombined together.

Further, in order to improve characteristics of the organic EL device, it has been desired to develop a device that maintains carrier balance and has high efficiency, low driving voltage and a long lifetime by using in combination the materials that excel in hole and electron injection/transport performances, stability as a thin film and durability.

CITATION LIST

Patent Literature

PTL 1: JP-A-8-048656
PTL 2: Japanese Patent No. 3194657
PTL 3: Japanese Patent No. 4943840

PTL 4: JP-A-2006-151979
PTL 5: WO2008/62636
PTL 6: WO2011/059000
PTL 7: WO2003/060956
PTL 8: JP-A-7-126615
PTL 9: JP-A-2005-108804

Non Patent Literature

NPL 1: The Japan Society of Applied Physics, 9th Lecture Preprints, pp. 55 to 61 (2001)
NPL 2: The Japan Society of Applied Physics, 9th Lecture Preprints, pp. 23 to 31 (2001)
NPL 3: Appl. Phys. Let., 98, 083302 (2011)
NPL 4: Organic EL Symposium, the 3rd Regular presentation Preprints, pp. 13 to 14 (2006)

SUMMARY OF INVENTION

Technical Problem

An object of the present invention is to provide a material for an organic EL device that is excellent in hole injection and transport abilities, electron blocking ability, thin film stability, and durability, as a material for an organic EL device with high efficiency and high durability, and also to provide an organic EL device having a high efficiency, a low driving voltage, and a long lifetime by combining the material with various materials for an organic EL device that is excellent in hole and electron injection and transport abilities, electron blocking ability, thin film stability, and durability, in such a manner that the characteristics of the materials can be effectively exhibited.

Physical properties of the organic compound to be provided by the present invention include (1) good hole injection characteristics, (2) large hole mobility, (3) excellent electron blocking ability, (4) stability in a thin-film state, and (5) excellent heat resistance. Physical properties of the organic EL device to be provided by the present invention include (1) high luminous efficiency and high power efficiency, (2) low turn on voltage, (3) low actual driving voltage, and (4) a long lifetime.

Solution to Problem

For achieving the object, the present inventors have focused the fact that an arylamine material is excellent in hole injection ability and transport ability, thin film stability, and durability, and they have synthesized various compounds and have earnestly investigated the characteristics thereof. As a result, it has been found that an arylamine compound substituted with an aryl group at a particular position can efficiently inject and transport holes to a light emitting layer. Furthermore, they have focused the fact that a compound having a pyrimidine ring structure is excellent in electron injection ability and transport ability, thin film stability, and durability, and they have produced various organic EL devices in such a manner that the arylamine compound substituted with an aryl group at a particular position and a compound having a pyrimidine ring structure having a particular structure are selected to inject and transport holes and electrons efficiently to a light emitting layer, and the hole transport material and the electron transport material are combined to maintain carrier balance, and have earnestly investigated the characteristics of the devices. Also, they have formed a hole transport layer having a two-layer structure of a first hole transport layer and a second hole transport layer, and have selected two specific kinds of triphenylamine derivative. And, they have selected a material of a first hole transport layer and a second hole transport layer such that holes can be efficiently injected and transported into a light emitting layer. They have produced various organic EL devices that maintain carrier balance by refining combinations of those. Then, they have intensively conducted characteristic evaluations of the devices. As a result, they have completed the present invention.

Specifically, according to the present invention, the following organic EL devices are provided.

1) An organic EL device comprising at least an anode, a hole transport layer, a light emitting layer, an electron transport layer, and a cathode in this order, wherein the hole transport layer comprises an arylamine compound of the following general formula (1):

[Chemical Formula 1]

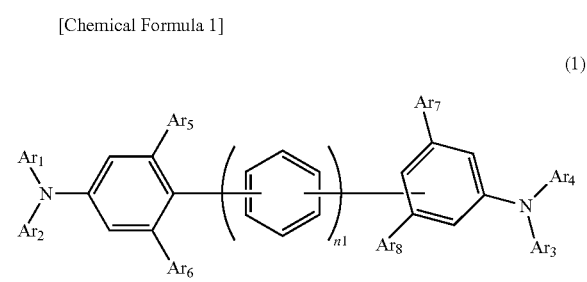

In the formula, $Ar_1$ to $Ar_5$ may be the same or different, and represent a substituted or unsubstituted aromatic hydrocarbon group, a substituted or unsubstituted aromatic heterocyclic group, or a substituted or unsubstituted condensed polycyclic aromatic group. $Ar_6$ to $Ar_8$ may be the same or different, and represent a hydrogen atom, a substituted or unsubstituted aromatic hydrocarbon group, a substituted or unsubstituted aromatic heterocyclic group, or a substituted or unsubstituted condensed polycyclic aromatic group. n1 represents 0, 1 or 2.

2) The organic EL device of 1), wherein the arylamine compound is an arylamine compound of the following general formula (1a).

[Chemical Formula 2]

(1a)

In the formula, $Ar_1$ to $Ar_5$ may be the same or different, and represent a substituted or unsubstituted aromatic hydrocarbon group, a substituted or unsubstituted aromatic heterocyclic group, or a substituted or unsubstituted condensed polycyclic aromatic group. $Ar_6$ to $Ar_8$ may be the same or different, and represent a hydrogen atom, a substituted or unsubstituted aromatic hydrocarbon group, a substituted or unsubstituted aromatic heterocyclic group, or a substituted or unsubstituted condensed polycyclic aromatic group. n1 represents 0, 1 or 2.

3) The organic EL device of any one of 1) to 2), wherein the electron transport layer includes a compound of the following general formula (2) having a pyrimidine ring structure.

[Chemical Formula 3]

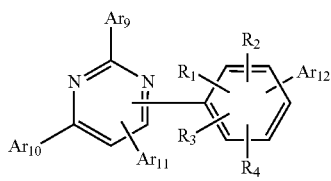

(2)

In the formula, $Ar_9$ represents a substituted or unsubstituted aromatic hydrocarbon group or a substituted or unsubstituted condensed polycyclic aromatic group. $Ar_{10}$ to $Ar_{11}$ may be the same or different, and represent a hydrogen atom, a substituted or unsubstituted aromatic hydrocarbon group or a substituted or unsubstituted condensed polycyclic aromatic group. $Ar_{12}$ represents a substituted or unsubstituted aromatic heterocyclic group. $R_1$ to $R_4$ may be the same or different, and represent a hydrogen atom, a deuterium atom, a fluorine atom, a chlorine atom, cyano, trifluoromethyl, linear or branched alkyl of 1 to 6 carbon atoms, a substituted or unsubstituted aromatic hydrocarbon group, a substituted or unsubstituted aromatic heterocyclic group, or a substituted or unsubstituted condensed polycyclic aromatic group. $Ar_{10}$ and $Ar_{11}$ are not simultaneously a hydrogen atom.

4) The organic EL device of any one of 1) to 3), wherein the hole transport layer has a two-layer structure of a first hole transport layer and a second hole transport layer, and the second hole transport layer includes the arylamine compound.

5) The organic electroluminescent device of 4), wherein the first hole transport layer includes a triphenylamine derivative different from the arylamine compound included in the second hole transport layer, and the triphenylamine derivative is a compound having a molecular structure containing two triphenylamine skeletons bonded to each other via a single bond or a divalent hydrocarbon group, and having 2 to 6 triphenylamine skeletons as a whole molecule.

6) The organic EL device of 5), wherein the triphenylamine derivative contained in the first hole transport layer is a derivative of the following general formula (3).

[Chemical Formula 4]

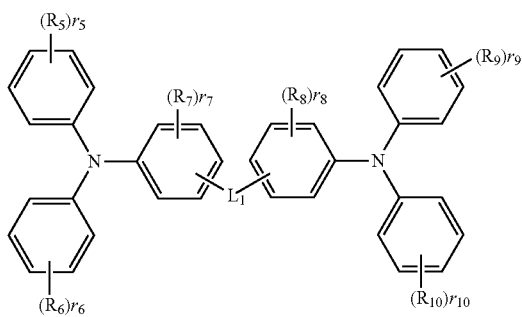

(3)

In the formula, $R_5$ to $R_{10}$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. $r_5$ to $r_{10}$ may be the same or different, $r_5$, $r_6$, $r_9$ and $r_{10}$ representing 0 to 5, and $r_7$ and $r_8$ representing 0 to 4. When $r_5$, $r_6$, $r_9$ and $r_{10}$ are 2 to 5, or when $r_7$ and $r_8$ are 2 to 4, $R_5$ to $R_{10}$, a plurality of which bind to the same benzene ring, may be the same or different and may bind to each other via a single bond, substituted or unsubstituted methylene, an oxygen atom, or a sulfur atom to form a ring. $L_1$ represents a divalent group of the following structural formulas (C) to (G), or a single bond.

[Chemical Formula 5]

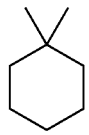

(C)

[Chemical Formula 6]

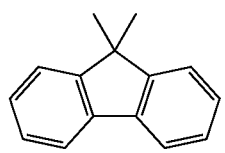

(D)

[Chemical Formula 7]

—$CH_2$—

(E)

[Chemical Formula 8]

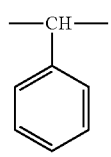

(F)

[Chemical Formula 9]

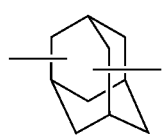

(G)

7) The organic EL device of 5), wherein the triphenylamine derivative contained in the first hole transport layer is a derivative of the following general formula (4).

[Chemical Formula 10]

(4)

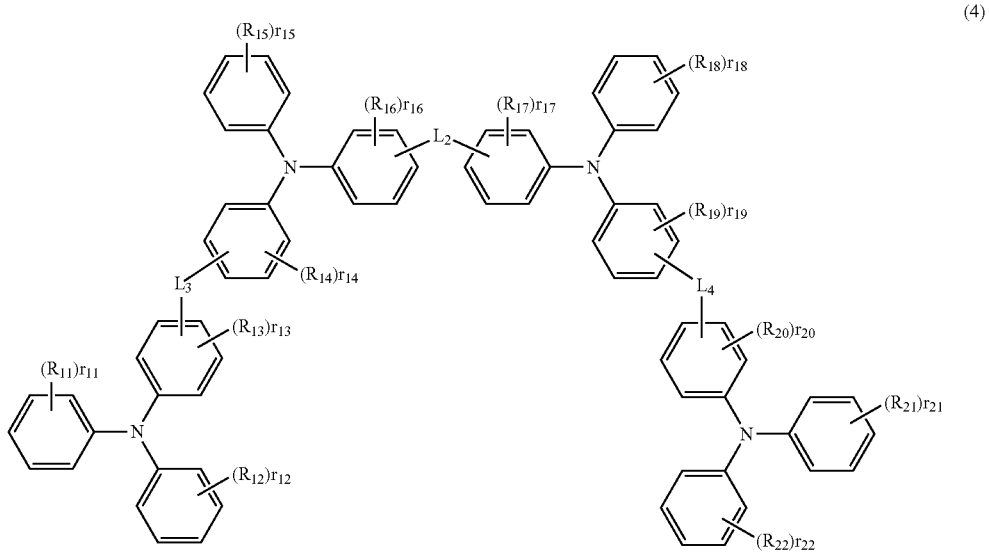

In the formula, $R_{11}$ to $R_{22}$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. $r_{11}$ to $r_{22}$ may be the same or different, $r_{11}$, $r_{12}$, $r_{15}$, $r_{18}$, $r_{21}$ and $r_{22}$ representing 0 to 5, and $r_{13}$, $r_{14}$, $r_{16}$, $r_{17}$, $r_{19}$ and $r_{20}$ representing 0 to 4. When $r_{11}$, $r_{12}$, $r_{15}$, $r_{18}$, $r_{21}$ and $r_{22}$ are 2 to 5, or when $r_{13}$, $r_{14}$, $r_{16}$, $r_{17}$, $r_{19}$ and $r_{20}$ are 2 to 4, $R_{11}$ to $R_{22}$, a plurality of which bind to the same benzene ring, may be the same or different and may bind to each other via a single bond, substituted or unsubstituted methylene, an oxygen atom, or a sulfur atom to form a ring. $L_2$, $L_3$ and $L_4$ may be the same or different, and represent a divalent group of the following structural formulas (B) to (G), or a single bond.

[Chemical Formula 11]

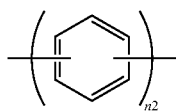

(B)

In the formula, n2 represents 1 to 3.

[Chemical Formula 12]

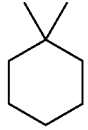

(C)

[Chemical Formula 13]

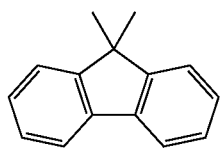

(D)

[Chemical Formula 14]

—CH$_2$—

(E)

[Chemical Formula 15]

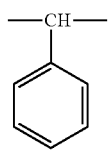

—CH—

(F)

[Chemical Formula 16]

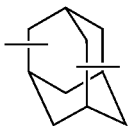

(G)

8) The organic EL device of any one of 1) to 7), wherein the light emitting layer includes a blue light emitting dopant.

9) The organic EL device of 8), wherein the light emitting layer includes a blue light emitting dopant, which is a pyrene derivative.

10) The organic EL device of any one of 1) to 9), wherein the light emitting layer includes an anthracene derivative.

11) The organic EL device of 10), wherein the light emitting layer includes a host material which is the anthracene derivative.

12) An arylamine compound of the following general formula (1).

[Chemical Formula 17]

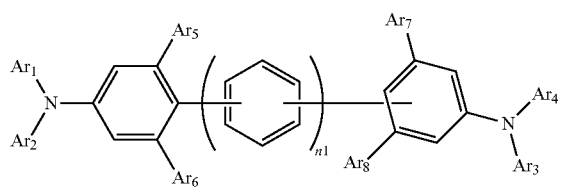

(1)

In the formula, $Ar_1$ to $Ar_5$ may be the same or different, and represent a substituted or unsubstituted aromatic hydrocarbon group, a substituted or unsubstituted aromatic heterocyclic group, or a substituted or unsubstituted condensed polycyclic aromatic group. $Ar_6$ to $Ar^8$ may be the same or different, and represent a hydrogen atom, a substituted or unsubstituted aromatic hydrocarbon group, a substituted or unsubstituted aromatic heterocyclic group, or a substituted or unsubstituted condensed polycyclic aromatic group. n1 represents 0, 1 or 2.

13) The arylamine compound of 12), wherein the arylamine compound of the following general formula (1a).

[Chemical Formula 18]

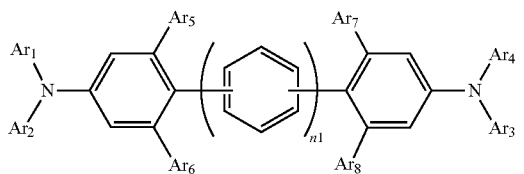

(1a)

In the formula, $Ar_1$ to $Ar_5$ may be the same or different, and represent a substituted or unsubstituted aromatic hydrocarbon group, a substituted or unsubstituted aromatic heterocyclic group, or a substituted or unsubstituted condensed polycyclic aromatic group. $Ar_6$ to $Ar^8$ may be the same or different, and represent a hydrogen atom, a substituted or unsubstituted aromatic hydrocarbon group, a substituted or unsubstituted aromatic heterocyclic group, or a substituted or unsubstituted condensed polycyclic aromatic group. n1 represents 0, 1 or 2.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar^8$ in the general formula (1) and the general formula (1a) include phenyl, biphenylyl, terphenylyl, naphthyl, anthracenyl, phenanthrenyl, fluorenyl, indenyl, pyrenyl, perylenyl, fluoranthenyl, triphenylenyl, pyridyl, pyrimidinyl, triazinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, naphthyridinyl, phenanthrolinyl, acridinyl, and carbolinyl.

Specific examples of the "substituent" in the "substituted aromatic hydrocarbon group", the "substituted aromatic heterocyclic group", or the "substituted condensed polycyclic aromatic group" represented by $Ar_1$ to $Ar_8$ in the general formula (1) and the general formula (1a) include a deuterium atom, cyano, nitro; halogen atoms, such as a fluorine atom, a chlorine atom, a bromine atom, and an iodine atom; linear or branched alkyls of 1 to 6 carbon atoms, such as methyl, ethyl, n-propyl, isopropyl, n-butyl, isobutyl, tert-butyl, n-pentyl, isopentyl, neopentyl, and n-hexyl; linear or branched alkyloxys of 1 to 6 carbon atoms, such as methyloxy, ethyloxy, and propyloxy; alkenyls, such as vinyl and allyl; aryloxys, such as phenyloxy and tolyloxy; arylalkyloxys, such as benzyloxy and phenethyloxy; an aromatic hydrocarbon group or a condensed polycyclic aromatic group, such as phenyl, biphenylyl, terphenylyl, naphthyl, anthracenyl, phenanthrenyl, fluorenyl, indenyl, pyrenyl, perylenyl, fluoranthenyl, and triphenylenyl; an aromatic heterocyclic group, such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzimidazolyl, pyrazolyl, dibenzofuranyl, dibenzothienyl, and carbolinyl; arylvinyls, such as styryl and naphthylvinyl; acyls, such as acetyl and benzoyl. These substituents may be further substituted with the exemplified substituents above. These substituents may bind to each other via a single bond, substituted or unsubstituted methylene, an oxygen atom, or a sulfur atom to form a ring.

Specific examples of the "aromatic hydrocarbon group" or the "condensed polycyclic aromatic group" in the "substituted or unsubstituted aromatic hydrocarbon group" or the "substituted or unsubstituted condensed polycyclic aromatic group" represented by $Ar_9$, $Ar_{10}$ and $Ar_{11}$ in the general formula (2) include phenyl, biphenylyl, terphenylyl, quaterphenyl, styryl, naphthyl, anthracenyl, acenaphthenyl, phenanthrenyl, fluorenyl, indenyl, pyrenyl, perylenyl, fluoranthenyl and triphenylenyl.

Further, these groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_8$ in the general formula (1) and the general formula (1a), and possible embodiments may also be the same embodiments as the exemplified embodiments.

Specific examples of the "aromatic heterocyclic group" in the "substituted or unsubstituted aromatic heterocyclic group" represented by $Ar_{12}$ in the general formula (2) include triazinyl, pyridyl, pyrimidinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, naphthyridinyl, phenanthrolinyl, acridinyl, and carbolinyl.

Further, these groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_8$ in the general formula (1) and the general formula (1a), and possible embodiments may also be the same embodiments as the exemplified embodiments.

Specific examples of the "linear or branched alkyl of 1 to 6 carbon atoms" represented by $R_1$ to $R_4$ in the general formula (2) include methyl, ethyl, n-propyl, isopropyl, n-butyl, 2-methylpropyl, tert-butyl, n-pentyl, 3-methylbutyl, tert-pentyl, n-hexyl, isohexyl and tert-hexyl.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_1$ to $R_4$ in the general formula (2) include phenyl, biphenylyl, terphenylyl, quaterphenyl, styryl, naphthyl, anthracenyl, acenaphthenyl, phenanthrenyl, fluorenyl, indenyl, pyrenyl, perylenyl, fluoranthenyl, triphenylenyl, triazinyl, pyridyl, pyrimidinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, naphthyridinyl, phenanthrolinyl, acridinyl, and carbolinyl.

Further, these groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_8$ in the general formula (1) and the general formula (1a), and possible embodiments may also be the same embodiments as the exemplified embodiments.

The "substituent" in the "substituted aromatic hydrocarbon group", the "substituted aromatic heterocyclic group", or the "substituted condensed polycyclic aromatic group" represented by $Ar_1$ to $Ar_8$ in the general formula (1) and the general formula (1a) is preferably a deuterium atom, the "linear or branched alkyl of 1 to 6 carbon atoms that may have a substituent", the "linear or branched alkenyl of 2 to 6 carbon atoms that may have a substituent", the "substituted or unsubstituted aromatic hydrocarbon group", or the "substituted or unsubstituted condensed polycyclic aromatic group", far preferably, a deuterium atom, phenyl, biphenylyl, naphthyl, or vinyl. It is also preferable that these groups bind to each other via a single bond to form a condensed aromatic ring.

In the general formula (1) and the general formula (1a), n1 represents 0 or an integer of 1 to 2, in which the case where n1 is 0 shows that the two benzene rings substituted with a diarylamino group are bonded directly (via a single bond), the case where n1 is 1 shows that the two benzene rings substituted with a diarylamino group are bonded via one phenylene group, and the case where n1 is 2 shows that the two benzene rings substituted with a diarylamino group are bonded via two phenylene groups (biphenylene group).

$Ar_9$ in the general formula (2) is preferably phenyl, biphenylyl, naphthyl, anthracenyl, acenaphthenyl, phenanthrenyl, fluorenyl, indenyl, pyrenyl, perylenyl, fluoranthenyl or triphenylenyl, and further preferably phenyl, biphenylyl, naphthyl, anthracenyl, phenanthrenyl, pyrenyl, fluoranthenyl or triphenylenyl. The phenyl group preferably has a substituted or unsubstituted condensed polycyclic aromatic group as a substituent, and further preferably has a substituent selected from naphthyl, anthracenyl, phenanthrenyl, pyrenyl, fluoranthenyl and triphenylenyl.

$Ar_{10}$ in the general formula (2) is preferably phenyl that has a substituent. The substituent of the phenyl in this case is preferably an aromatic hydrocarbon group, such as phenyl, biphenylyl, and terphenyl, or a condensed polycyclic aromatic group, such as naphthyl, anthracenyl, acenaphthenyl, phenanthrenyl, fluorenyl, indenyl, pyrenyl, perylenyl, fluoranthenyl, and triphenylenyl, and further preferably phenyl, naphthyl, anthracenyl, phenanthrenyl, pyrenyl, fluoranthenyl, or triphenylenyl.

$Ar_{11}$ in the general formula (2) is preferably phenyl that has a substituent. The substituent of the phenyl in this case is preferably an aromatic hydrocarbon group, such as phenyl, biphenylyl, and terphenyl, or a condensed polycyclic aromatic group, such as naphthyl, anthracenyl, acenaphthenyl, phenanthrenyl, fluorenyl, indenyl, pyrenyl, perylenyl, fluoranthenyl, and triphenylenyl, and further preferably phenyl, naphthyl, anthracenyl, phenanthrenyl, pyrenyl, fluoranthenyl, or triphenylenyl.

In the general formula (2), it is preferable that $Ar_9$ and $Ar_{10}$ are not the same as each other from the viewpoint of thin film stability. When $Ar_9$ and $Ar_{10}$ are the same groups, the groups may have different substituents and may be substituted on different positions.

In the general formula (2), $Ar_{10}$ and $Ar_{11}$ may be the same groups, but there may be a possibility that the compound is easily crystallized due to the high symmetry of the entire molecule, and from the viewpoint of thin film stability, it is preferable that $Ar_{10}$ and $Ar_{11}$ are not the same as each other, and $Ar_{10}$ and $Ar_{11}$ are not simultaneously a hydrogen atom.

In the general formula (2), it is preferable that one of $Ar_{10}$ and $Ar_{11}$ is a hydrogen atom.

$Ar_{12}$ in the general formula (2) is preferably a nitrogen-containing heterocyclic group such as triazinyl, pyridyl, pyrimidinyl, pyrrolyl, quinolyl, isoquinolyl, indolyl, carbazolyl, benzoxazolyl, benzothiazolyl, quinoxalinyl, benzoimidazolyl, pyrazolyl, naphthyridinyl, phenanthrolinyl, acridinyl, or carbolinyl, more preferably triazinyl, pyridyl, pyrimidinyl, quinolyl, isoquinolyl, indolyl, quinoxalinyl, benzoimidazolyl, naphthyridinyl, phenanthrolinyl, or acridinyl, particularly preferably pyridyl, pyrimidinyl, quinolyl, isoquinolyl, indolyl, quinoxalinyl, benzoimidazolyl, phenanthrolinyl, or acridinyl.

In the general formula (2), a bonding position of $Ar_{12}$ in the benzene ring is preferably a meta position with respect to a bonding position of the pyrimidine ring from the viewpoint of stability as a thin film.

Examples of the compound having a pyrimidine ring structure represented by the general formula (2) include compounds having a pyrimidine ring structure represented by the following general formula (2a) and general formula (2b) in which a bonding pattern of a substituent is different.

[Chemical Formula 19]

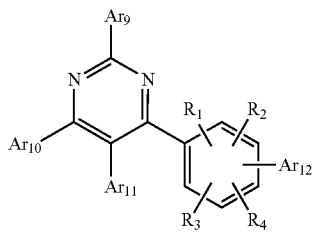

(2a)

In the formula, $Ar_9, Ar_{10}, Ar_{11}, Ar_{12}$ and $R_1$ to $R_4$ represent the same meanings as described in the above general formula (2).

[Chemical Formula 20]

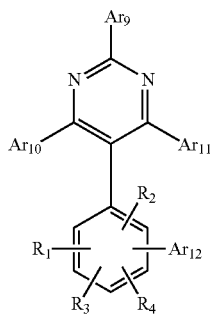

(2b)

In the formula, $Ar_9, Ar_{10}, Ar_{11}, Ar_{12}$ and $R_1$ to $R_4$ represent the same meanings as described in the above general formula (2).

An embodiment in which the organic EL device of the present invention is configured to laminate two hole transport layers is also preferably used. That is, the organic EL device of the present invention in this case is configured to have at least an anode, a first hole transport layer, a second hole transport layer, a light emitting layer, an electron transport layer, and a cathode in this order. In this case, an embodiment in which the second hole transport layer includes an arylamine compound represented by the general formula (1) or the general formula (1a) is preferable. Furthermore, an embodiment in which the first hole transport layer includes a triphenylamine derivative different from the arylamine compound included in the second hole transport layer, and the triphenylamine derivative is a compound having a molecular structure containing two triphenylamine skeletons bonded to each other via a single bond or a divalent hydrocarbon group, and having 2 to 6 triphenylamine skeletons as a whole molecule is far preferable.

The compound having a molecular structure containing the two triphenylamine skeletons bonded to each other via a single bond or a divalent hydrocarbon group, and having 2 to 6 triphenylamine skeletons as a whole molecule is preferably a triphenylamine derivative having two triphenylamine skeletons as a whole molecule represented by the following general formula (3) or a triphenylamine derivative having four triphenylamine skeletons as a whole molecule represented by the following general formula (4).

[Chemical Formula 21]

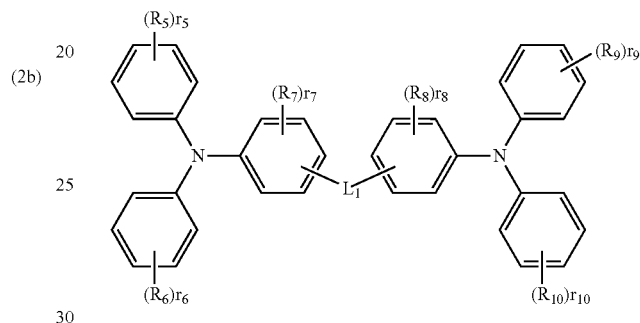

(3)

In the formula, $R_5$ to $R_{10}$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. $r_5$ to $r_{10}$ may be the same or different, $r_5$, $r_6$, $r_9$, and $r_{10}$ representing 0 to 5, and $r_7$ and $r_8$ representing 0 to 4. When $r_5$, $r_6$, $r_9$, and $r_{10}$ are 2 to 5, or when $r_7$ and $r_8$ are 2 to 4, $R_5$ to $R_{10}$, a plurality of which bind to the same benzene ring, may be the same or different, and may bind to each other via a single bond, substituted or unsubstituted methylene, an oxygen atom, or a sulfur atom to form a ring. $L_1$ represents a divalent group represented by the following structural formulas (C) to (G), or a single bond.

[Chemical Formula 22]

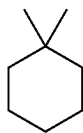

(C)

[Chemical Formula 23]

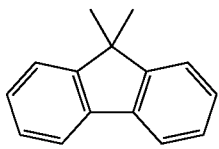

(D)

[Chemical Formula 24]

(E)

[Chemical Formula 25]

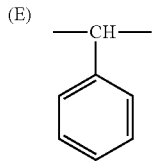
(F)

[Chemical Formula 26]

(G)

[Chemical Formula 27]

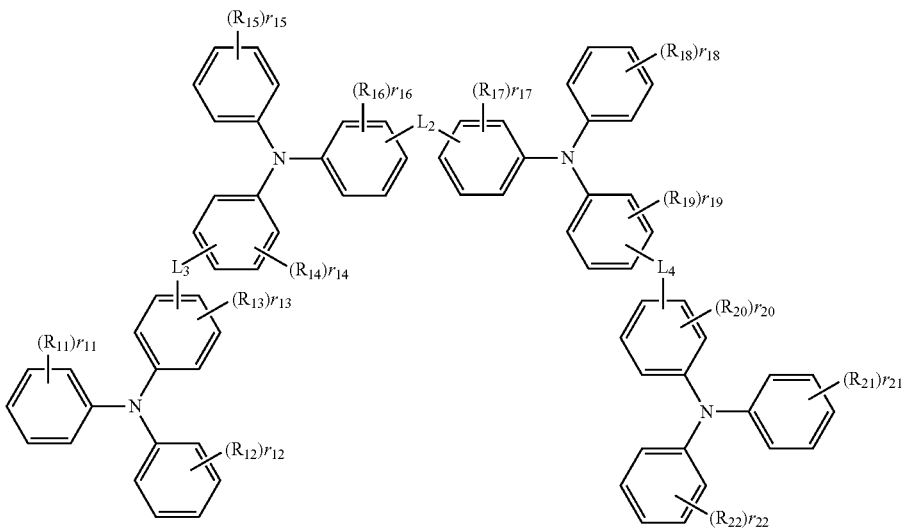
(4)

In the formula, $R_{11}$ to $R_{22}$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. $r_{11}$ to $r_{22}$ may be the same or different, $r_{11}$, $r_{12}$, $r_{15}$, $r_{18}$, $r_{21}$, and $r_{22}$ representing 0 to 5, and $r_{13}$, $r_{14}$, $r_{16}$, $r_{17}$, $r_{19}$, and $r_{20}$ representing 0 to 4. When $r_{11}$, $r_{12}$, $r_{15}$, $r_{18}$, $r_{21}$, and $r_{22}$ are 2 to 5, or when $r_{13}$, $r_{14}$, $r_{16}$, $r_{17}$, $r_{19}$, and $r_{20}$ are 2 to 4, $R_{11}$ to $R_{22}$, a plurality of which bind to the same benzene ring, may be the same or different, and may bind to each other via a single bond, substituted or unsubstituted methylene, an oxygen atom, or a sulfur atom to form a ring. $L_2$, $L_3$, and $L_4$ may be the same or different, and represent a divalent group represented by the following structural formulas (B) to (G), or a single bond.

[Chemical Formula 28]

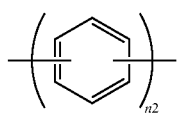
(B)

In the formula, n2 represents 1 to 3.

[Chemical Formula 29]

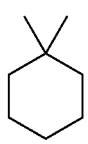
(C)

-continued

[Chemical Formula 30]

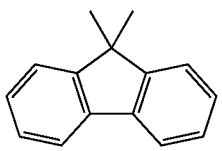
(D)

[Chemical Formula 31]

—CH$_2$—
(E)

[Chemical Formula 32]

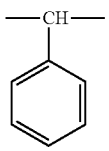
(F)

[Chemical Formula 33]

(G)

Specific examples of the "linear or branched alkyl group of 1 to 6 carbon atoms", the "cycloalkyl group of 5 to 10 carbon atoms", or the "linear or branched alkenyl group of 2 to 6 carbon atoms" in the "linear or branched alkyl group of 1 to 6 carbon atoms that may have a substituent", the "cycloalkyl group of 5 to 10 carbon atoms that may have a substituent", or the "linear or branched alkenyl group of 2 to 6 carbon atoms that may have a substituent" represented by $R_5$ to $R_{10}$ in the general formula (3) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These groups may bind to each other via a single bond, a substituted or unsubstituted methylene group, an oxygen atom, or a sulfur atom to form a ring.

Specific examples of the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_5$ to $R_{10}$ in the general formula (3) include a deuterium atom; cyano; nitro; halogen atoms such as a fluorine atom, a chlorine atom, a bromine atom, and an iodine atom; linear or branched alkyloxy of 1 to 6 carbon atoms such as methyloxy, ethyloxy, and propyloxy; alkenyl such as vinyl, and allyl; aryloxy such as phenyloxy, and tolyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, and carbolinyl. These substituents may be further substituted with the exemplified substituents above. These substituents may bind to each other via a single bond, substituted or unsubstituted methylene, an oxygen atom, or a sulfur atom to form a ring.

Specific examples of the "linear or branched alkyloxy of 1 to 6 carbon atoms", or the "cycloalkyloxy of 5 to 10 carbon atoms" in the "linear or branched alkyloxy of 1 to 6 carbon atoms that may have a substituent", or the "cycloalkyloxy of 5 to 10 carbon atoms that may have a substituent" represented by $R_5$ to $R_{10}$ in the general formula (3) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These groups may bind to each other via a single bond, substituted or unsubstituted methylene, an oxygen atom, or a sulfur atom to form a ring.

These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_5$ to $R_{10}$ in the general formula (3), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_5$ to $R_{10}$ in the general formula (3) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_8$ in the general formula (1) and the general formula (1a), these groups may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_8$ in the general formula (1) and the general formula (1a), and possible embodiments may also be the same embodiments as the exemplified embodiments.

Specific examples of the "aryloxy" in the "substituted or unsubstituted aryloxy" represented by $R_5$ to $R_{10}$ in the general formula (3) include phenyloxy, biphenylyloxy, terphenylyloxy, naphthyloxy, anthracenyloxy, phenanthrenyloxy, fluorenyloxy, indenyloxy, pyrenyloxy, and perylenyloxy. These groups may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_8$ in the general formula (1) and the general formula (1a), and possible embodiments may also be the same embodiments as the exemplified embodiments.

In the general formula (3), $R_5$ to $R_{10}$ may be the same or different, $r_5$, $r_6$, $r_9$, and $r_{10}$ representing 0 to 5, and $r_7$ and $r_8$ representing 0 to 4.

Examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{11}$ to $R_{22}$ in the general formula (4) include the same groups exemplified as the groups for the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_5$ to $R_{10}$ in the general formula (3), and possible embodiments may also be the same embodiments as the exemplified embodiments.

These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_5$ to $R_{10}$ in the general formula (3), and possible embodiments may also be the same embodiments as the exemplified embodiments.

Examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent", or the "cycloalkyloxy of 5 to 10 carbon atoms that may have a substituent" represented by $R_{11}$ to $R_{22}$ in the general formula (4) include the same groups exemplified as the groups for the "linear or branched alkyloxy of 1 to 6 carbon atoms", or the "cycloalkyloxy of 5 to 10 carbon atoms" in the "linear or branched alkyloxy of 1 to 6 carbon atoms that may have a substituent", or the "cycloalkyloxy of 5 to 10 carbon atoms that may have a substituent" represented by $R_5$ to $R_{10}$ in the general formula (3), and possible embodiments may also be the same embodiments as the exemplified embodiments.

These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_5$ to $R_{10}$ in the general formula (3), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{11}$ to $R_{22}$ in the general formula (4) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_8$ in the general formula (1) and the general formula (1a), these groups may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_8$ in the general formula (1) and the general formula (1a), and possible embodiments may also be the same embodiments as the exemplified embodiments.

Examples of the "aryloxy group" in the "substituted or unsubstituted aryloxy group" represented by $R_{11}$ to $R_{22}$ in the general formula (4) include the same groups exemplified as the groups for the "aryloxy group" in the "substituted or unsubstituted aryloxy group" represented by $R_5$ to $R_{10}$ in the general formula (3), and these groups may bind to each other via a single bond, a substituted or unsubstituted methylene group, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_8$ in the general formula (1) and the general formula (1a), and possible embodiments may also be the same embodiments as the exemplified embodiments.

$r_{11}$ to $r_{22}$ in the general formula (4) may be the same or different, $r_{11}$, $r_{12}$, $r_{15}$, $r_{18}$, $r_{21}$, and $r_{22}$ representing 0 to 5, and $r_{13}$, $r_{14}$, $r_{16}$, $r_{17}$, $r_{19}$, and $r_{20}$ representing 0 to 4.

In the structural formula (B), n2 represents 1 to 3.

The arylamine compounds of the general formula (1), and the general formula (1a), for preferred use in the organic EL device of the present invention, can be used as a constitutive material of a hole injection layer, an electron blocking layer, or a hole transport layer of an organic EL device. The arylamine compounds of the general formula (1) and the general formula (1a) have high hole mobility and are therefore preferred compounds as a material of a hole injection layer or a hole transport layer. Further, the arylamine compounds of the general formula (1) and the general formula (1a) have high electron blocking performance, and are therefore preferred compounds as a material of an electron blocking layer.

The compounds of the general formula (2) having a pyrimidine ring structure, for preferable use in the organic EL device of the present invention, can be used as a constitutive material of an electron transport layer of an organic EL device.

The compounds of the general formula (2) having a pyrimidine ring structure, excel in electron injection and transport abilities and further excel in stability as a thin film and durability, and are therefore preferred compounds as a material of an electron transport layer.

The triphenylamine derivatives of the general formula (3) having two triphenylamine skeletons as a whole molecule and the triphenylamine derivatives of the general formula (4) having four triphenylamine skeletons as a whole molecule, for preferable use in a first hole transport layer in the case where a hole transport layer has a two-layer structure of a first hole transport layer and a second hole transport layer for preferable embodiments in the organic EL device of the present invention, are preferred compounds as a constitutive material of a hole injection layer or a hole transport layer of an organic EL device.

The second hole transport layer in the case where a hole transport layer has a two-layer structure of a first hole transport layer and a second hole transport layer for preferable embodiments in the organic EL device of the present invention preferably includes an arylamine compound of the general formula (1) or the general formula (1a).

In the organic EL device of the present invention, materials for an organic EL device having excellent hole and electron injection/transport performances, stability as a thin film, and durability are combined while taking carrier balance into consideration. Therefore, compared with the conventional organic EL devices, hole transport efficiency to a light emitting layer from a hole transport layer is improved, and electron transport efficiency to a light emitting layer from an electron transport layer is also improved (further, two kinds of triphenylamine derivatives having a specific structure are combined while taking carrier balance and characteristics of materials into consideration in the case where a hole transport layer has a two-layer structure of a first hole transport layer and a second hole transport layer). As a result, luminous efficiency is improved, and also driving voltage is decreased, and thus, durability of the organic EL device can be improved.

Thus, an organic EL device having high luminous efficiency, low driving voltage, and a long lifetime can be attained.

The organic EL device of the present invention can achieve an organic EL device which can efficiently inject/transport holes into a light emitting layer, and therefore has high efficiency, low driving voltage, and a long lifetime by selecting a specific arylamine compound, which has excellent hole and electron injection/transport performances, stability as a thin film, and durability, and can effectively exhibit hole injection/transport roles. Further, an organic EL device having high efficiency, low driving voltage, and particularly a long lifetime can be achieved by selecting a specific arylamine compound, and by combining this compound with a specific electron transport material so as to achieve good carrier balance. Further, in the case where a hole transport layer has a two-layer structure of a first hole transport layer and a second hole transport layer, an organic EL device having higher efficiency and a longer lifetime can be realized by combining two kinds of triphenylamine derivatives having a specific structure while taking carrier balance and characteristics of materials into consideration. According to the present invention, the luminous efficiency, driving voltage, and durability of the conventional organic EL devices can be improved.

BRIEF DESCRIPTION OF DRAWINGS

FIG. 1 is a diagram illustrating the configuration of the organic EL devices of Examples 12 to 17 and Comparative Examples 1 to 2.

DESCRIPTION OF EMBODIMENTS

The following presents specific examples of preferred compounds among the arylamine compounds of the general formula (1) preferably used in the organic EL device of the present invention. The present invention, however, is not restricted to these compounds.

[Chemical Formula 34]

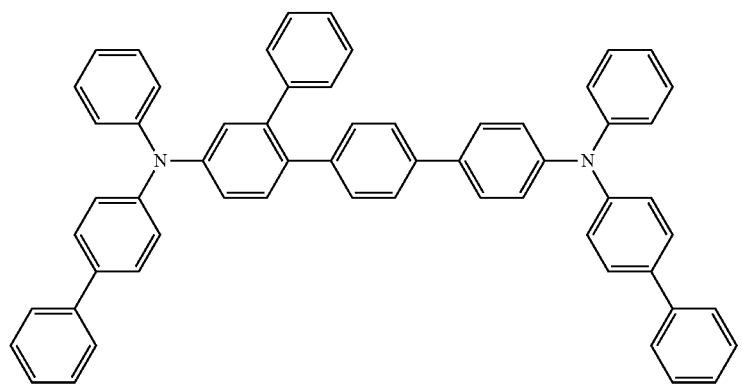

(1-1)

[Chemical Formula 35]

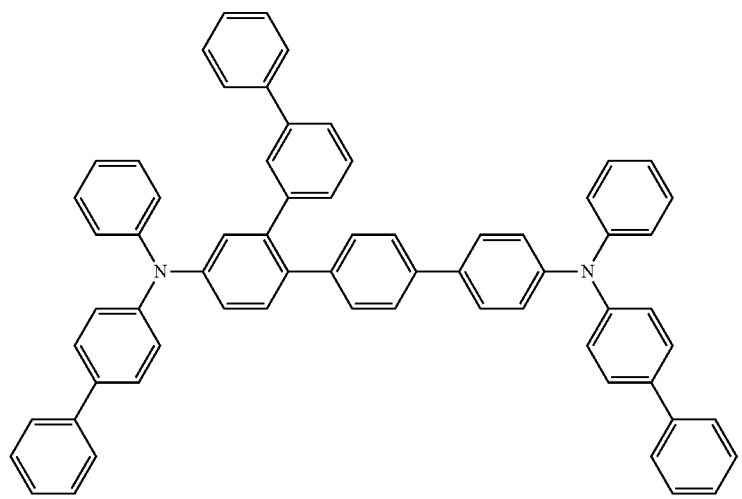

(1-2)

[Chemical Formula 36]
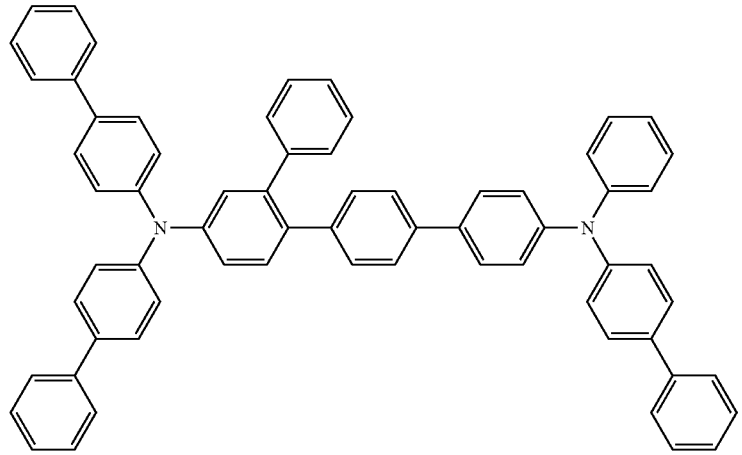
(1-3)
[Chemical Formula 37]
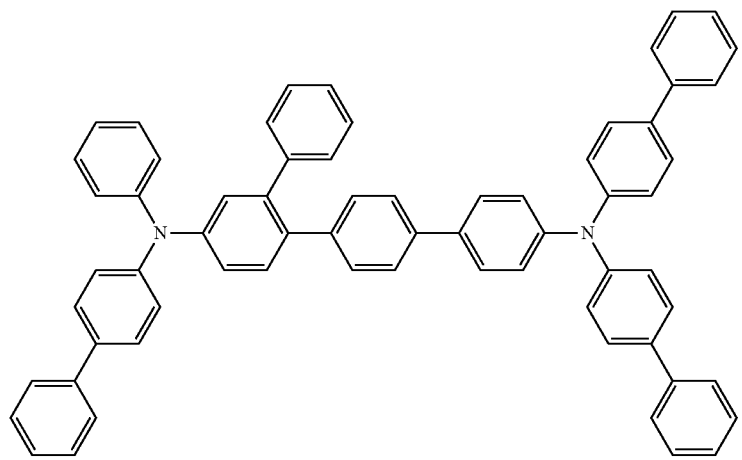
(1-4)
[Chemical Formula 38]
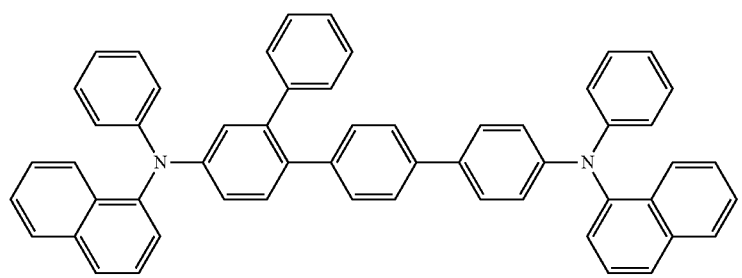
(1-5)

[Chemical Formula 39]
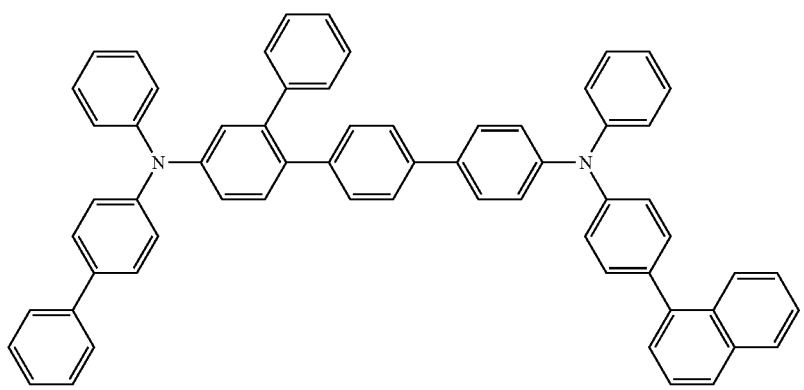
(1-6)
[Chemical Formula 40]
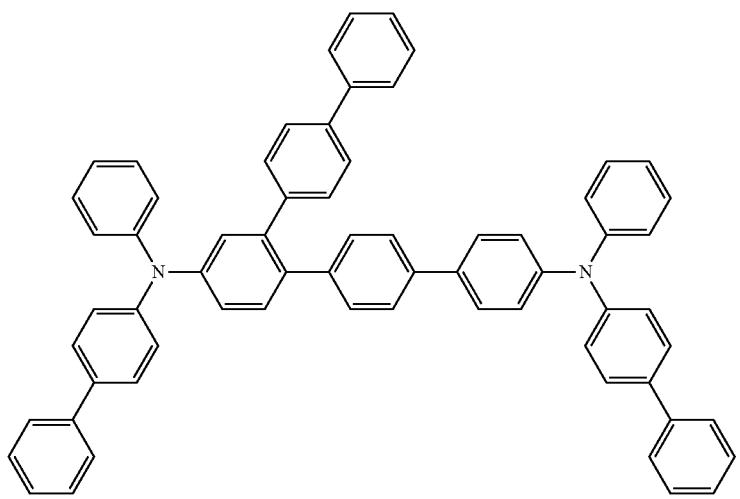
(1-7)
[Chemical Formula 41]
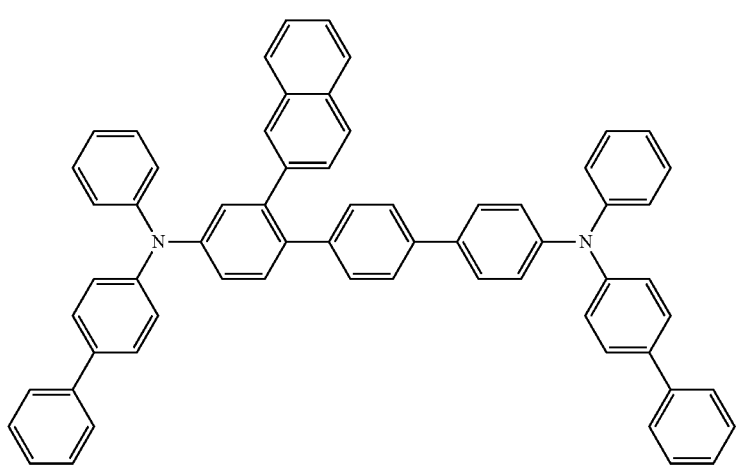
(1-8)

[Chemical Formula 42]
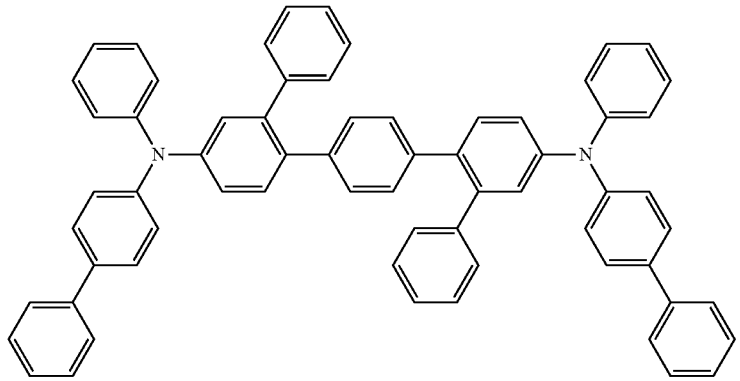
(1-9)
[Chemical Formula 43]
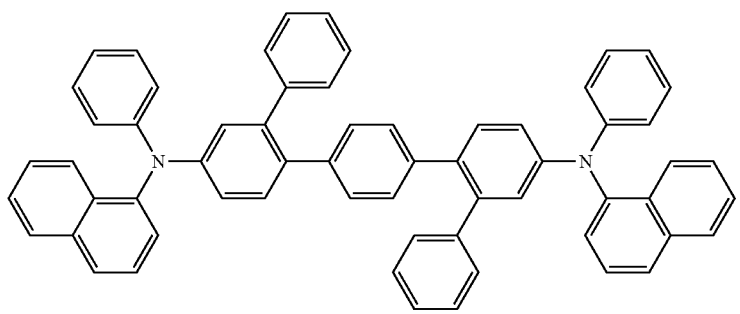
(1-10)
[Chemical Formula 44]
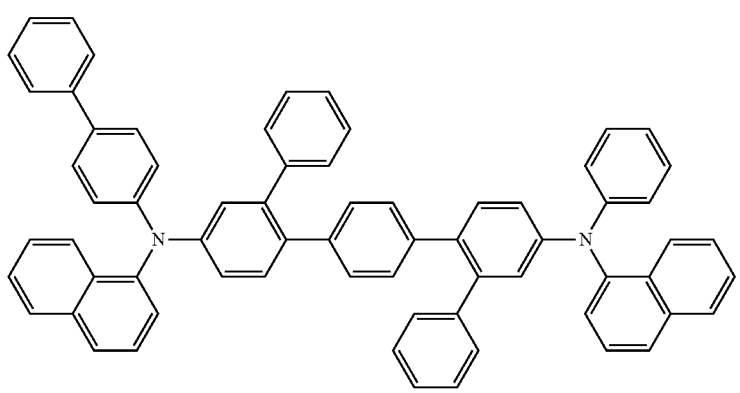
(1-11)

[Chemical Formula 45]
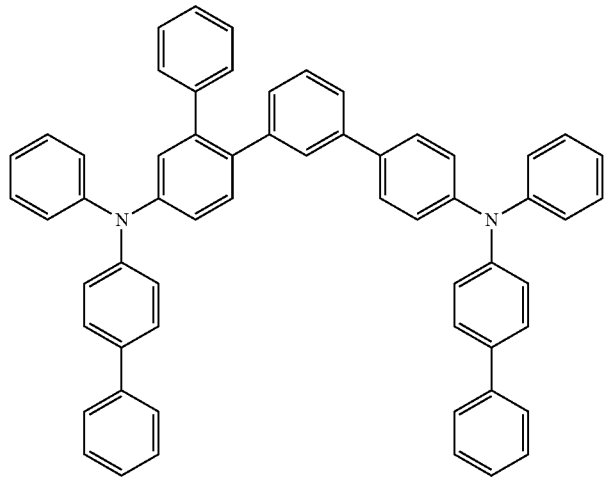
(1-12)
[Chemical Formula 46]
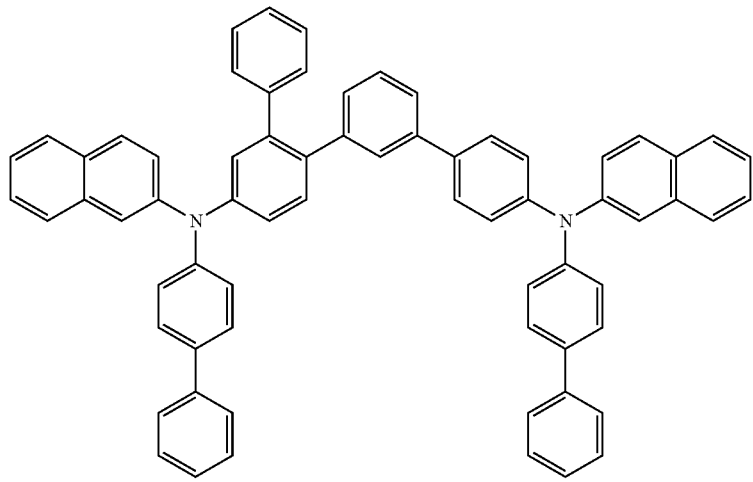
(1-13)
[Chemical Formula 47]
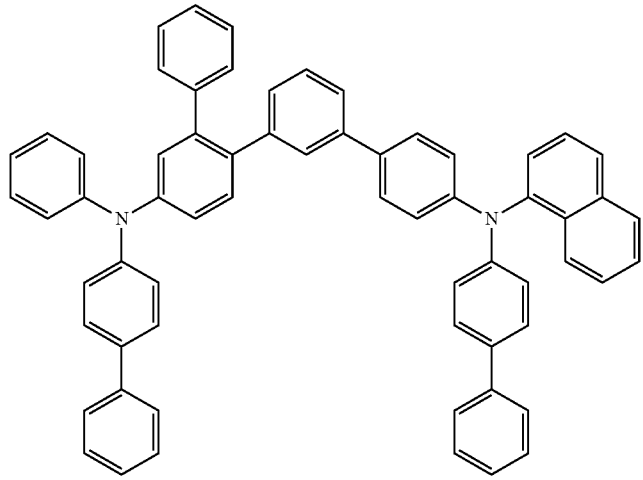
(1-14)

[Chemical Formula 48]
(1-15)
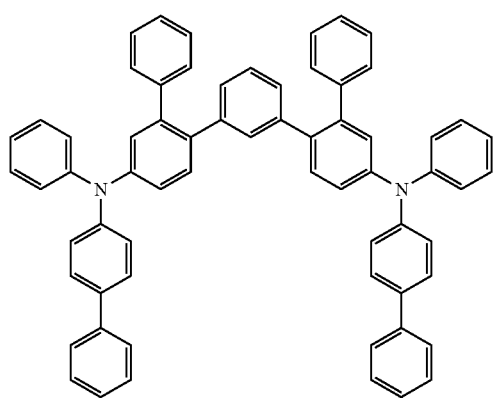
[Chemical Formula 49]
(1-16)
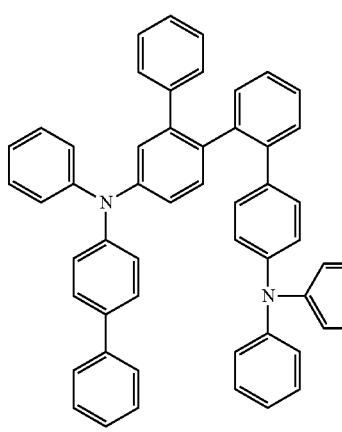
[Chemical Formula 50]
(1-17)
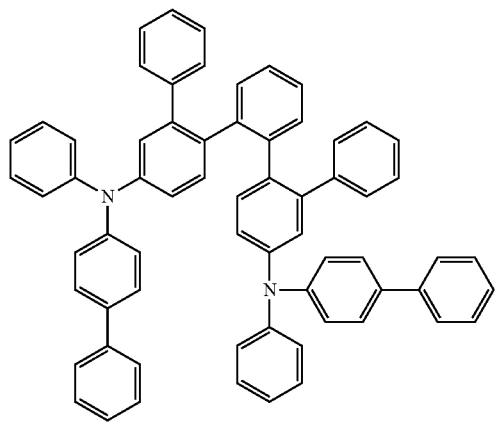
[Chemical Formula 51]
(1-18)
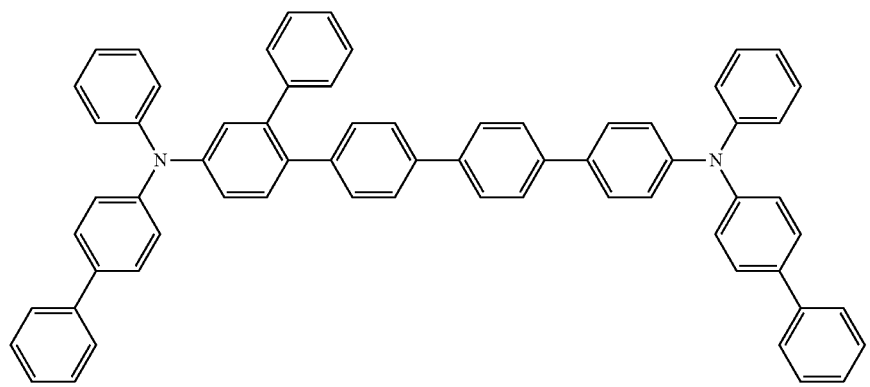

[Chemical Formula 52]
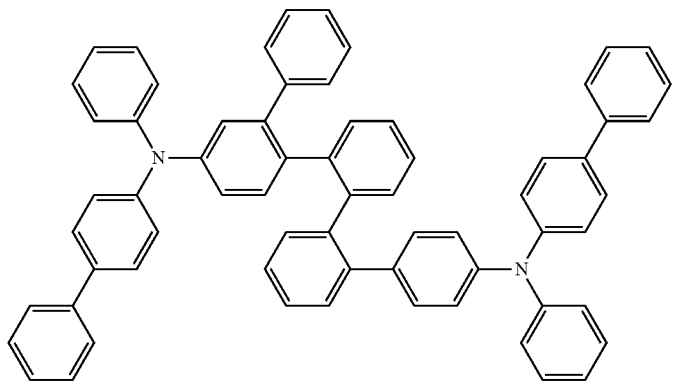
(1-19)
[Chemical Formula 53]
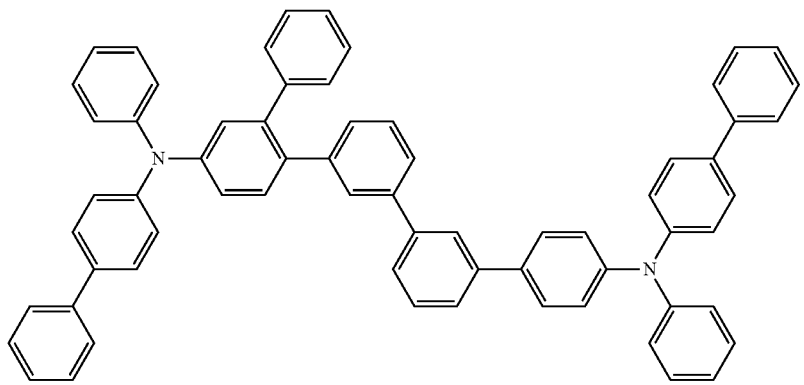
(1-20)
[Chemical Formula 54]
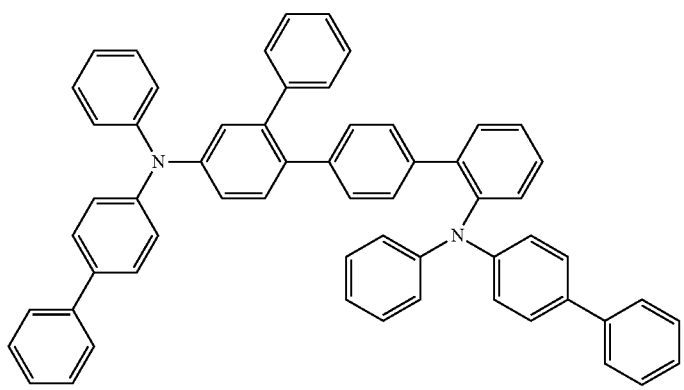
(1-21)

[Chemical Formula 55]
(1-22)
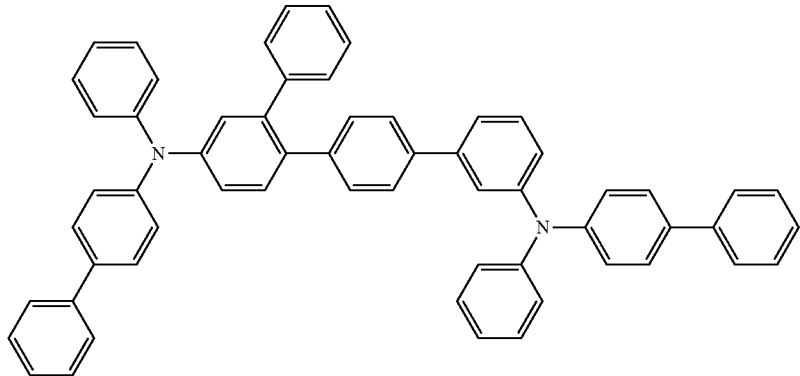
[Chemical Formula 56]
(1-23)
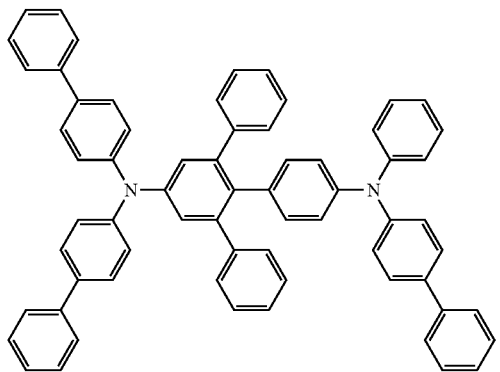
[Chemical Formula 57]
(1-24)
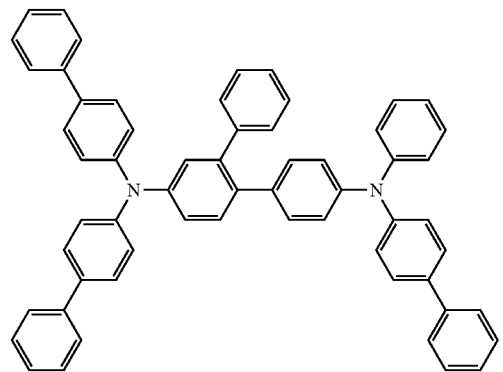
[Chemical Formula 58]
(1-25)
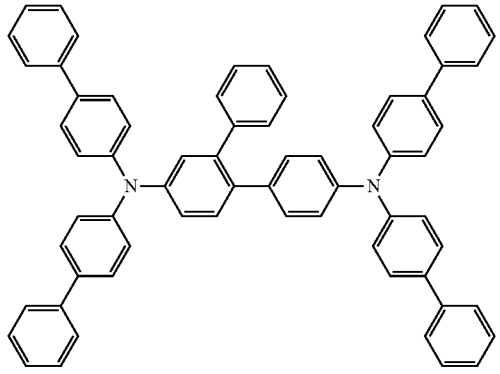
[Chemical Formula 59]
(1-26)
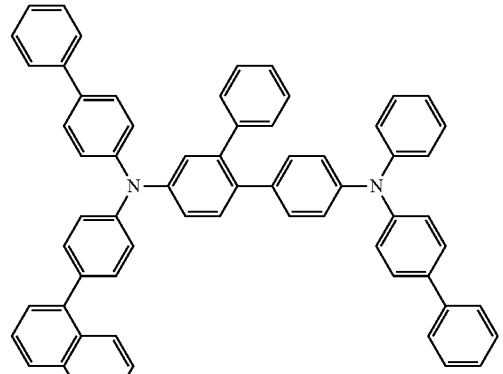

-continued
[Chemical Formula 60]
(1-27)
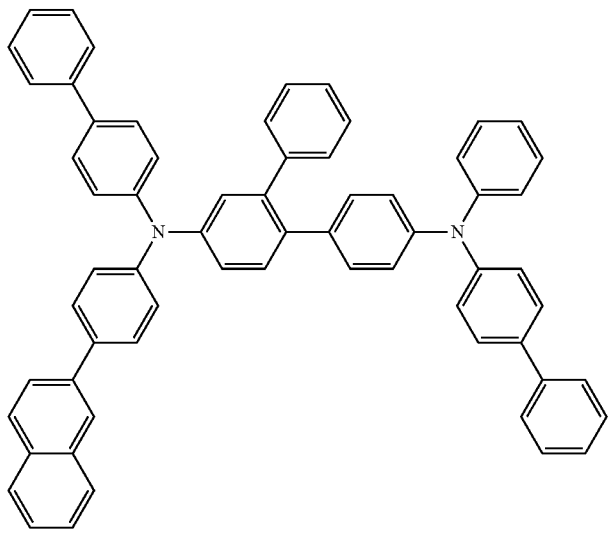
[Chemical Formula 61]
(1-28)
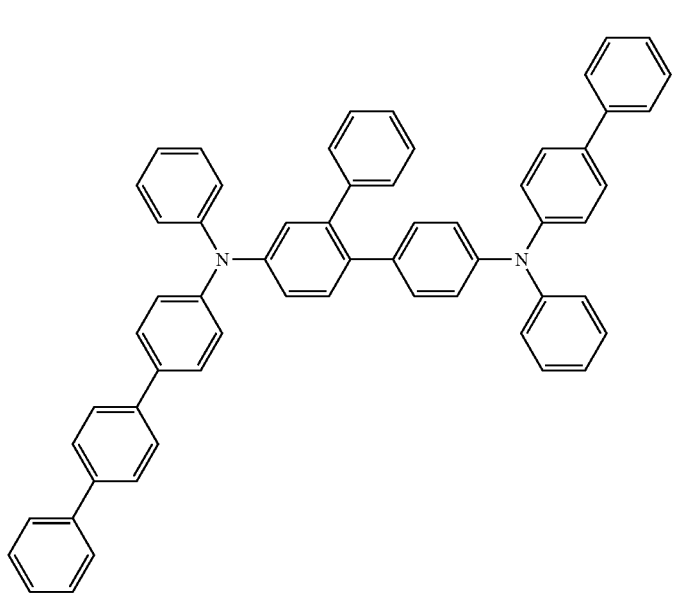
[Chemical Formula 62]
(1-29)
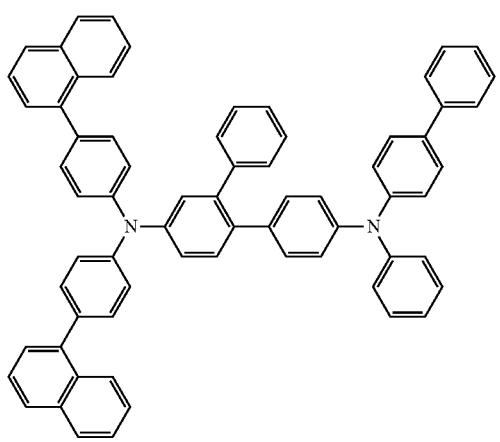
[Chemical Formula 63]
(1-30)
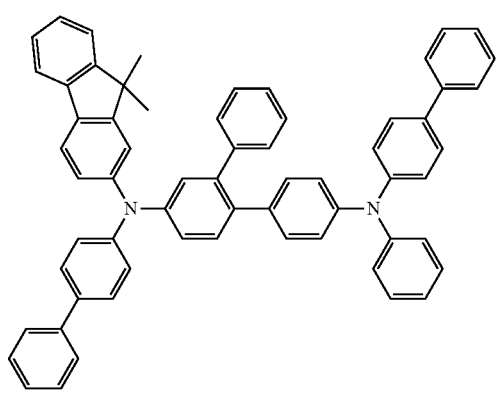

[Chemical Formula 64]
(1-31)
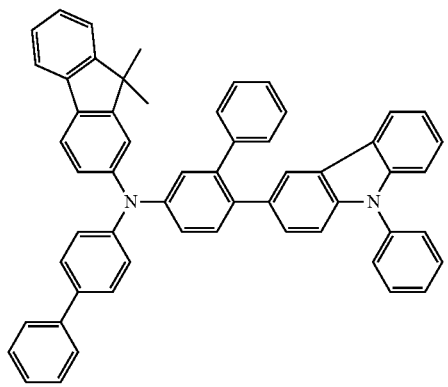
[Chemical Formula 65]
(1-32)
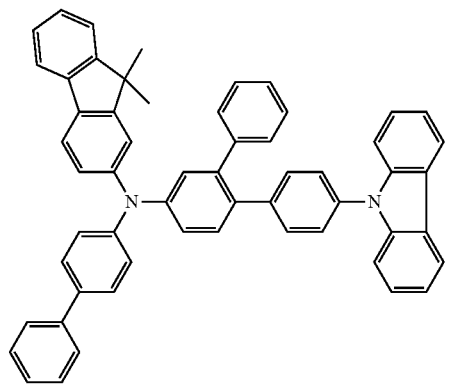
[Chemical Formula 66]
(1-33)
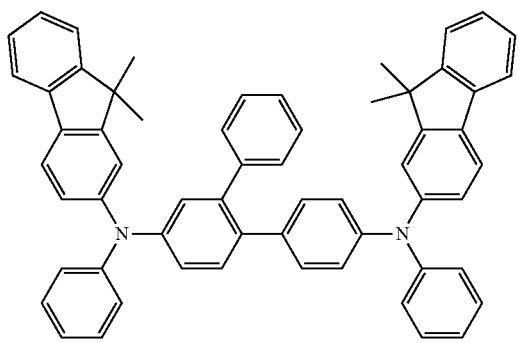
[Chemical Formula 67]
(1-34)
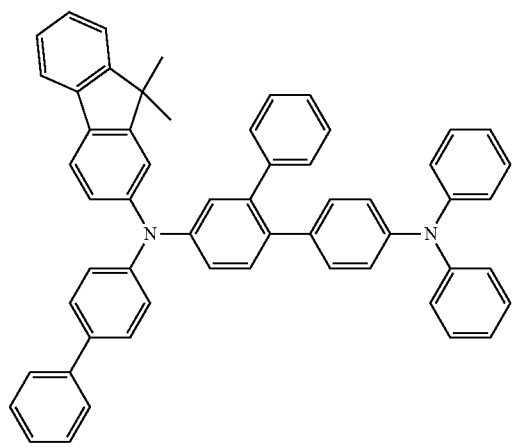
[Chemical Formula 68]
(1-35)
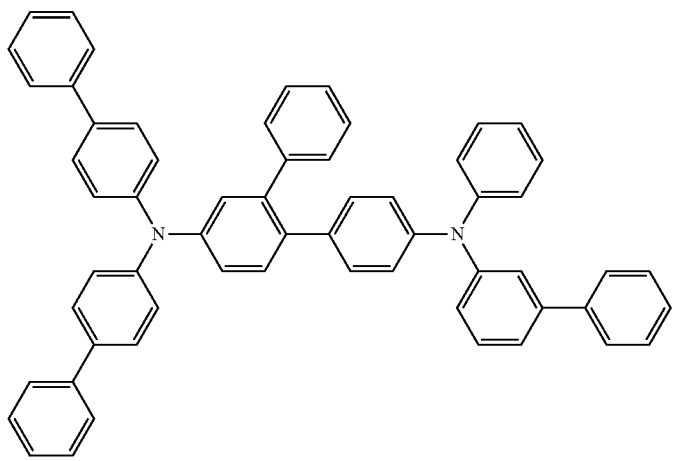

[Chemical Formula 69]
(1-36)
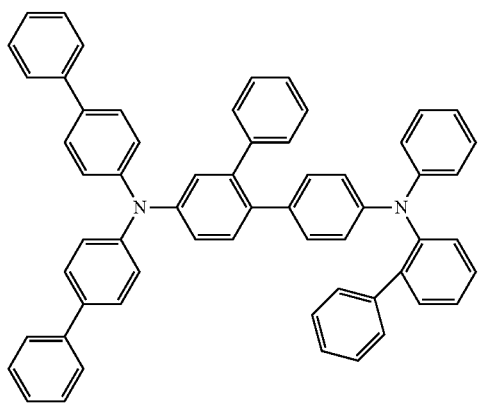
[Chemical Formula 70]
(1-37)
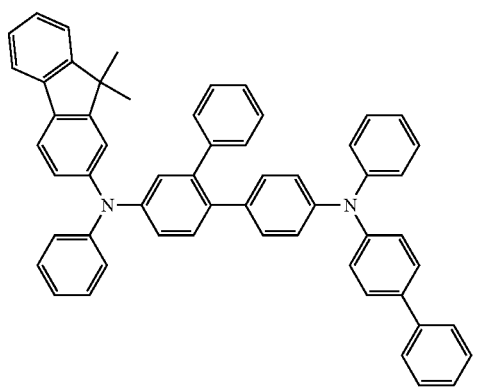
[Chemical Formula 71]
(1-38)
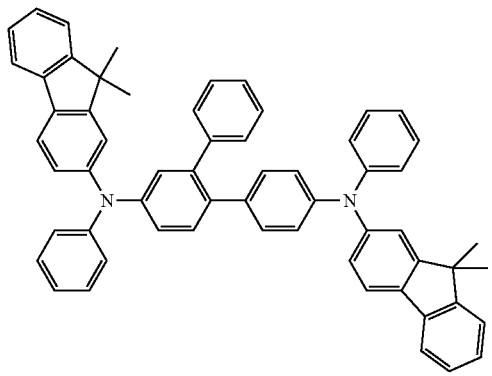
[Chemical Formula 72]
(1-39)
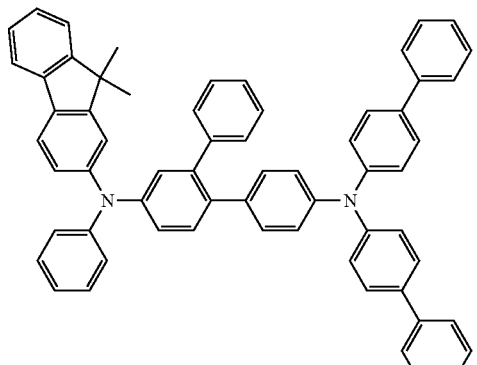
[Chemical Formula 73]
(1-40)
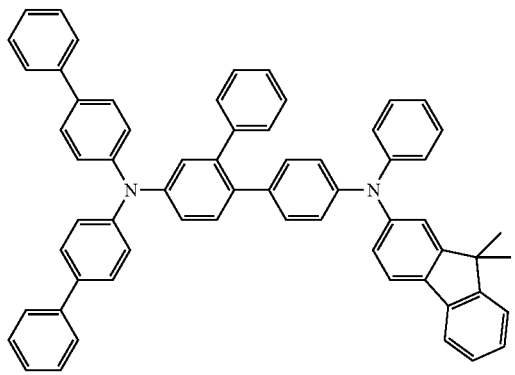
[Chemical Formula 74]
(1-41)
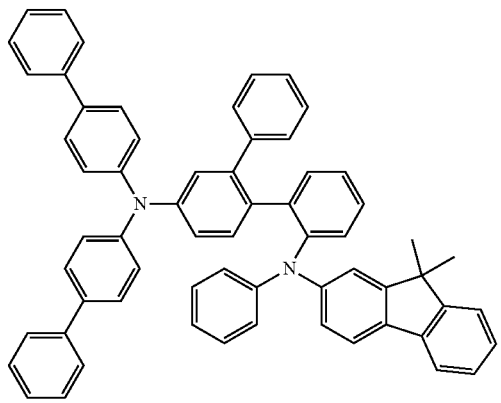

[Chemical Formula 75]

(1-42)

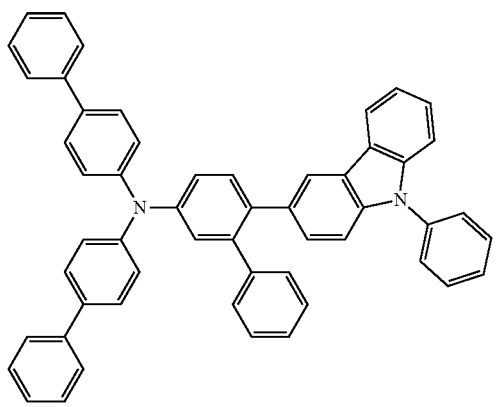

[Chemical Formula 76]

(1-43)

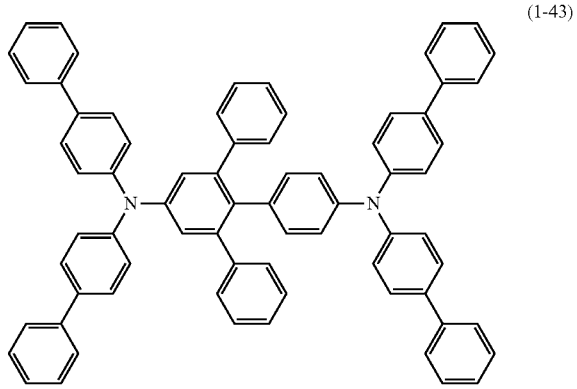

The following presents specific examples of preferred compounds among the compounds of the general formula (2) preferably used in the organic EL device of the present invention and having a pyrimidine ring structure. The present invention, however, is not restricted to these compounds.

[Chemical Formula 77]

(2-1)

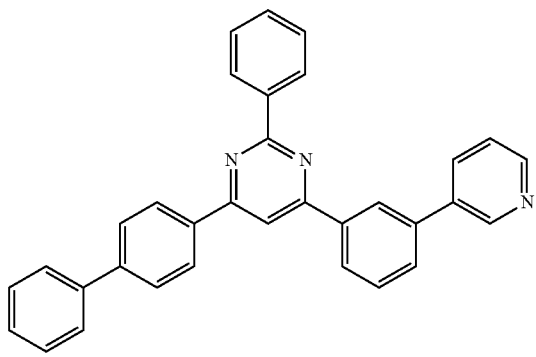

[Chemical Formula 79]

(2-3)

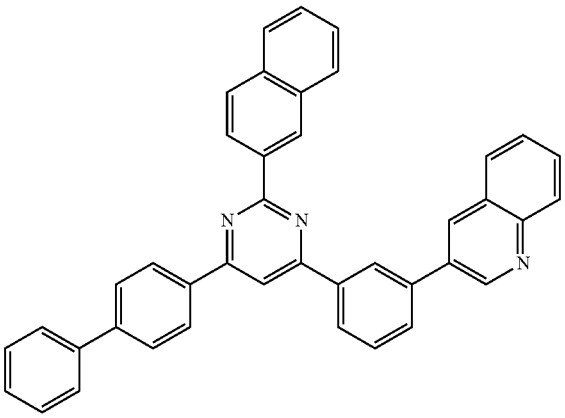

[Chemical Formula 78]

(2-2)

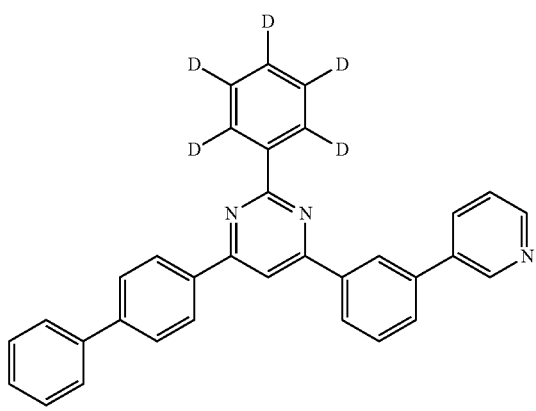

[Chemical Formula 80]

(2-4)

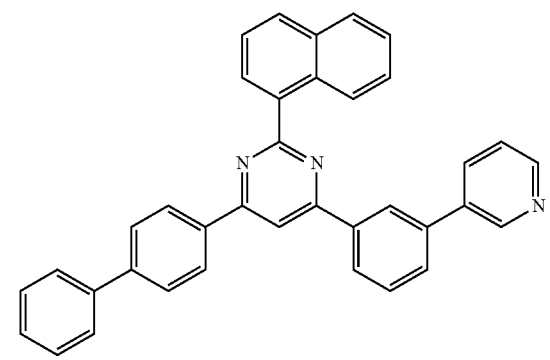

[Chemical Formula 81]
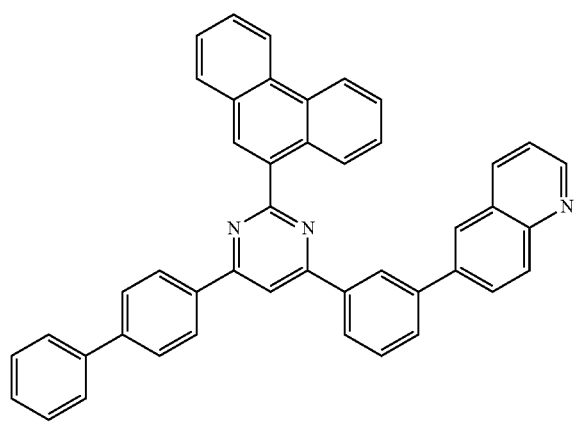
(2-5)
[Chemical Formula 82]
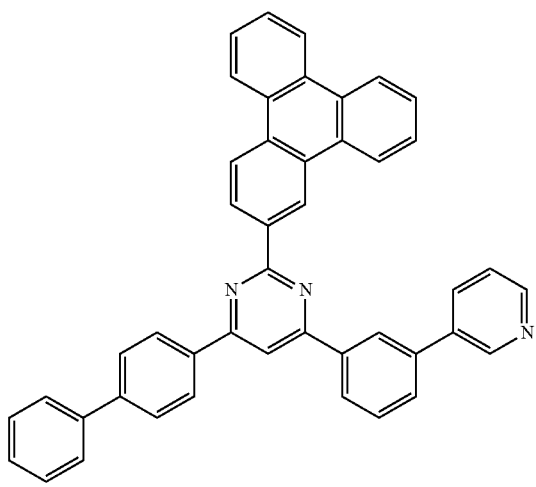
(2-6)
[Chemical Formula 83]
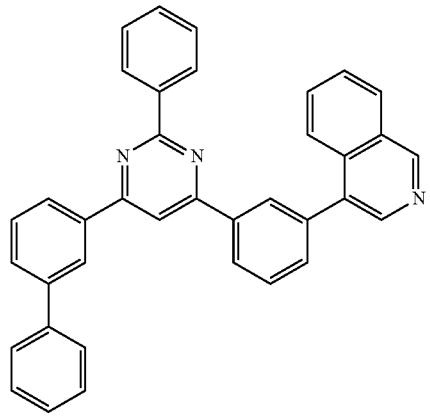
(2-7)
[Chemical Formula 84]
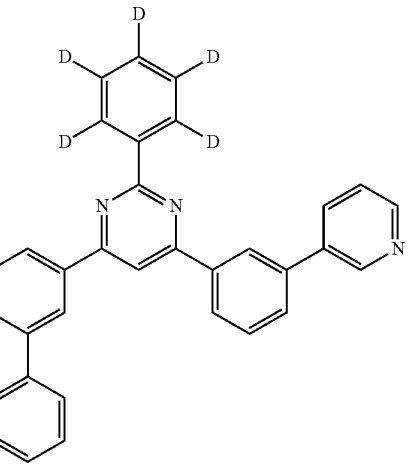
(2-8)
[Chemical Formula 85]
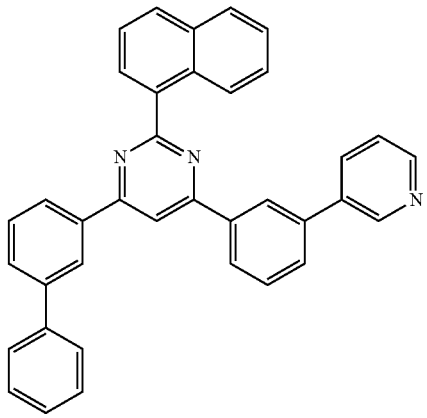
(2-9)
[Chemical Formula 86]
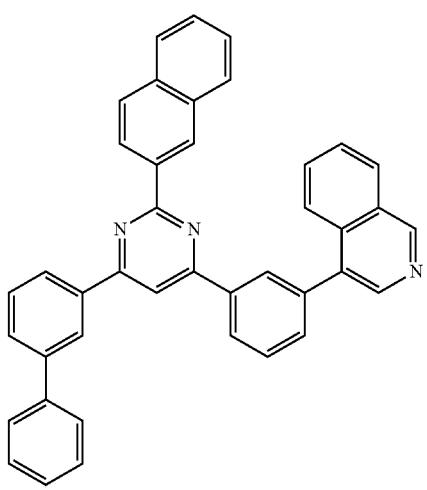
(2-10)

[Chemical Formula 87]
(2-11)
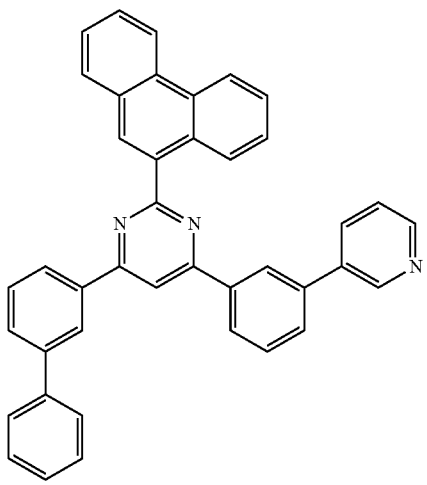
[Chemical Formula 88]
(2-12)
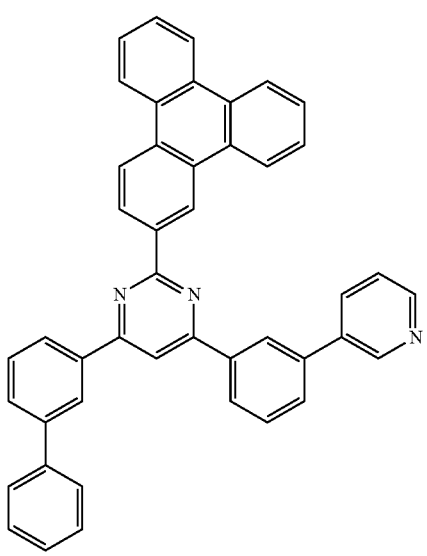
[Chemical Formula 89]
(2-13)
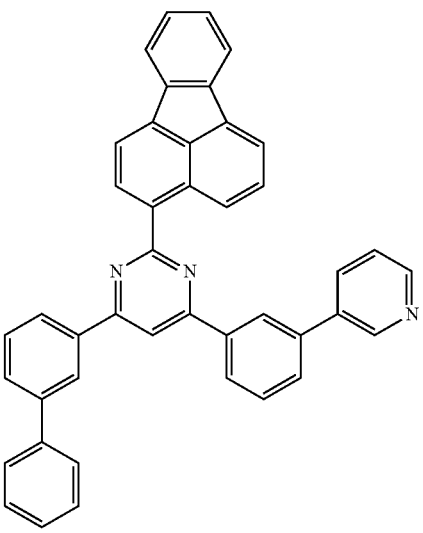
[Chemical Formula 90]
(2-14)
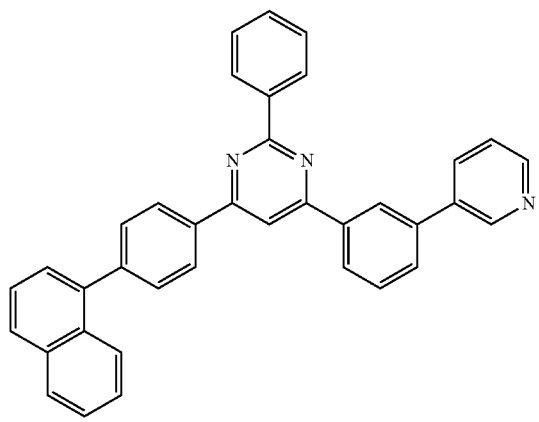
[Chemical Formula 91]
(2-15)
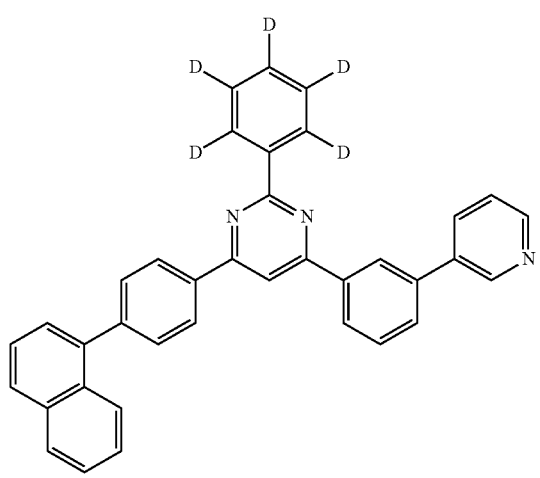

[Chemical Formula 92]
(2-16)
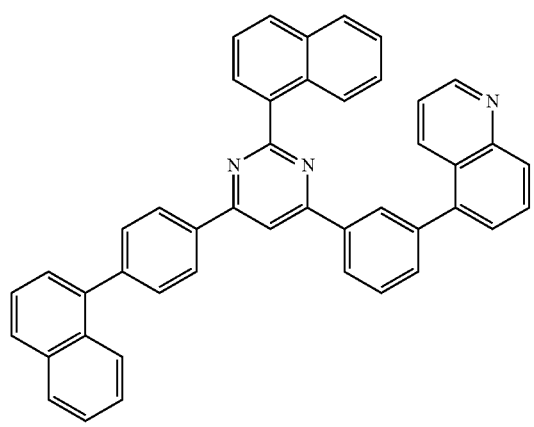
[Chemical Formula 93]
(2-17)
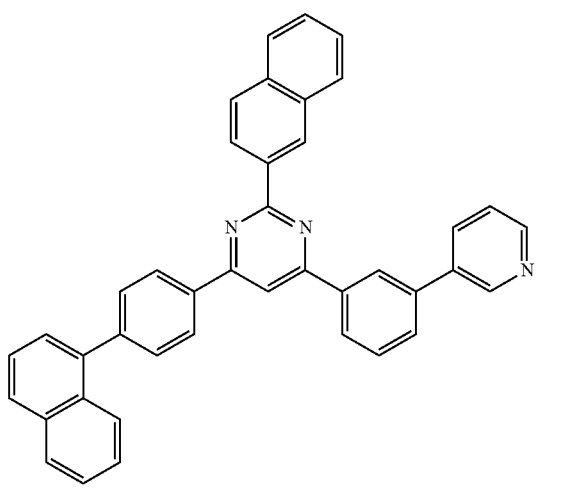
[Chemical Formula 94]
(2-18)
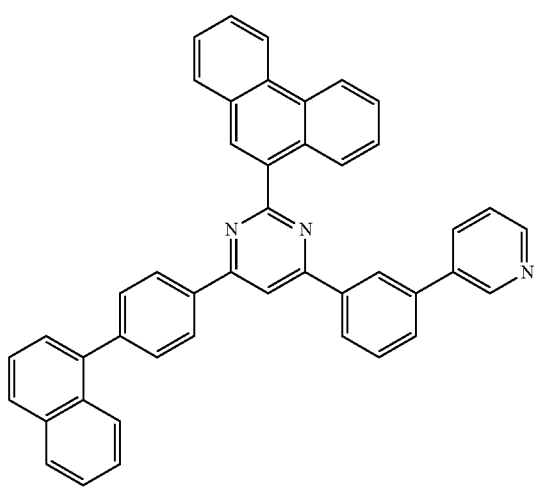
[Chemical Formula 95]
(2-19)
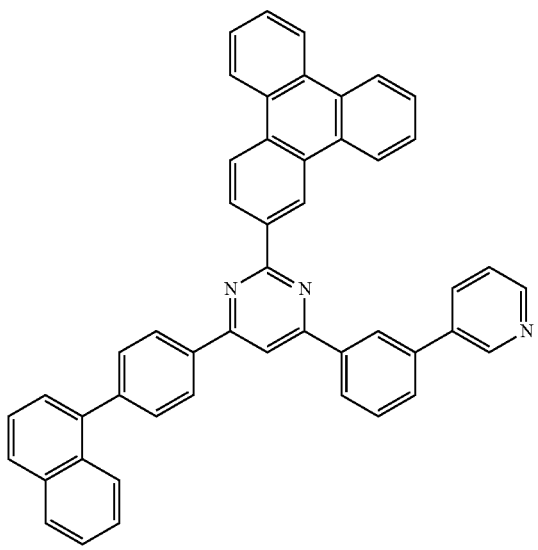
[Chemical Formula 96]
(2-20)
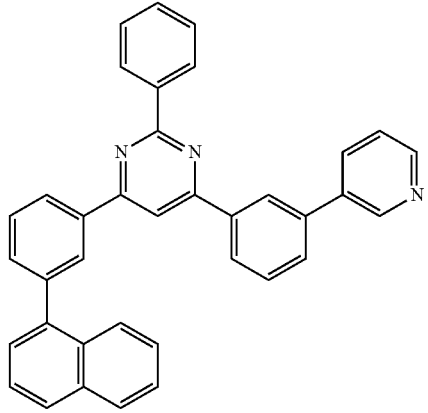
[Chemical Formula 97]
(2-21)
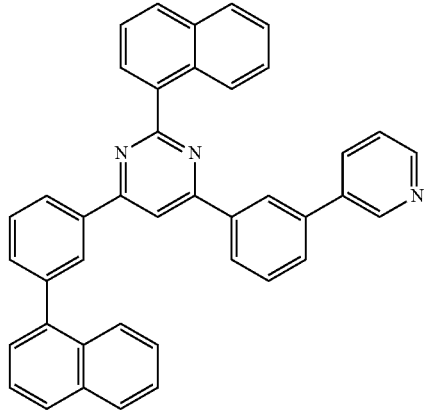

[Chemical Formula 98]
(2-22)
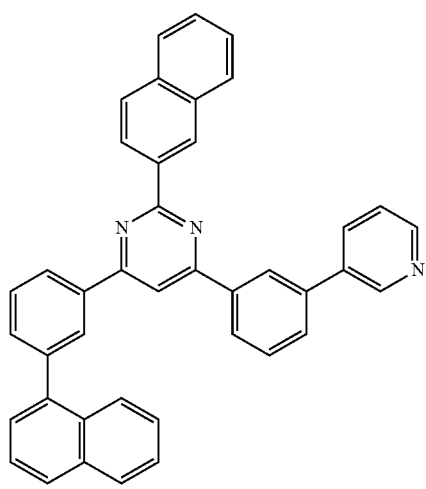
[Chemical Formula 99]
(2-23)
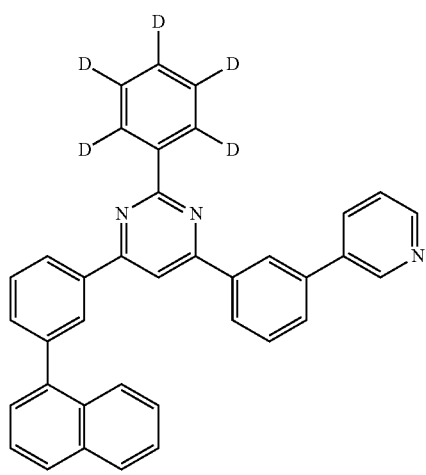
[Chemical Formula 100]
(2-24)
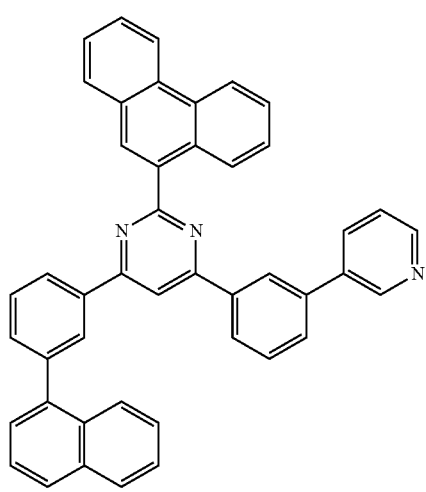
[Chemical Formula 101]
(2-25)
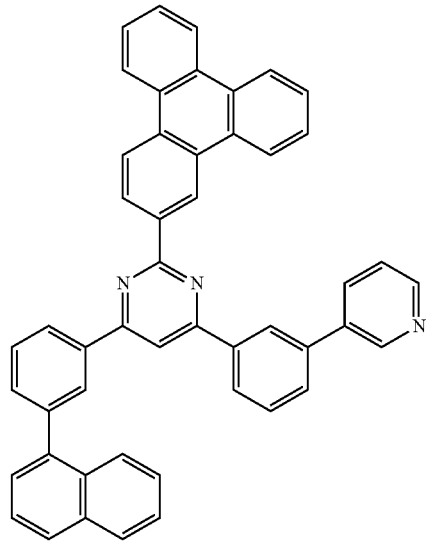
[Chemical Formula 102]
(2-26)
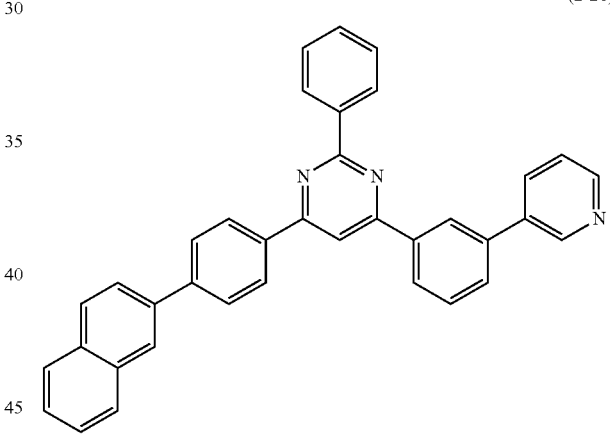
[Chemical Formula 103]
(2-27)
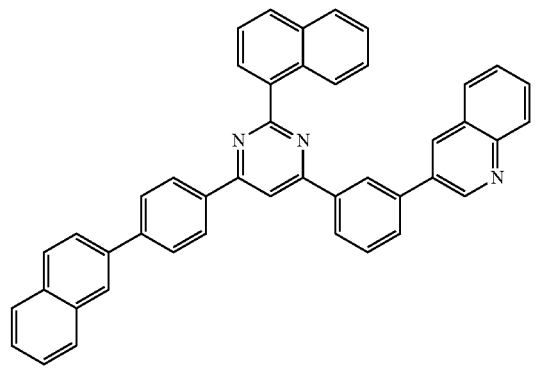

[Chemical Formula 104]
(2-28)
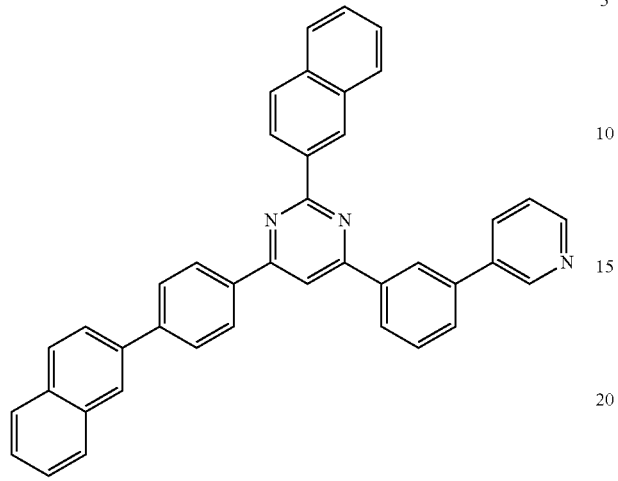
[Chemical Formula 105]
(2-29)
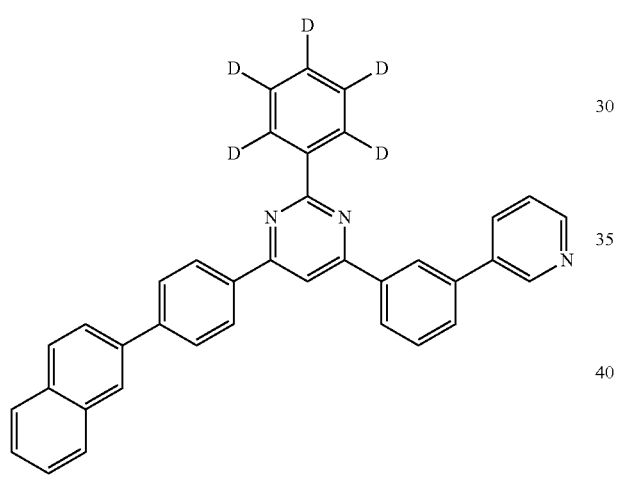
[Chemical Formula 106]
(2-30)
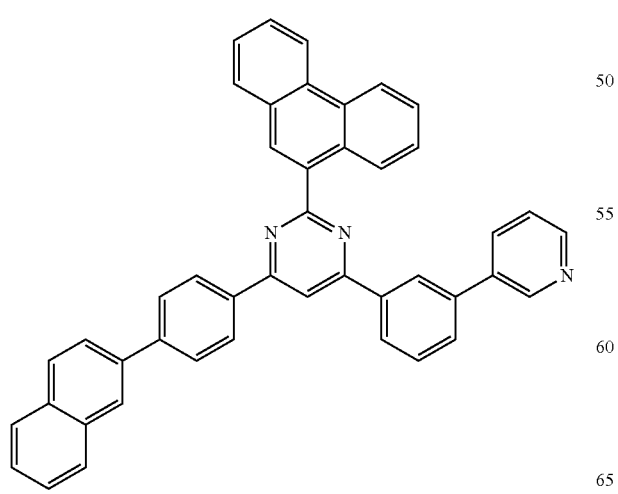
[Chemical Formula 107]
(2-31)
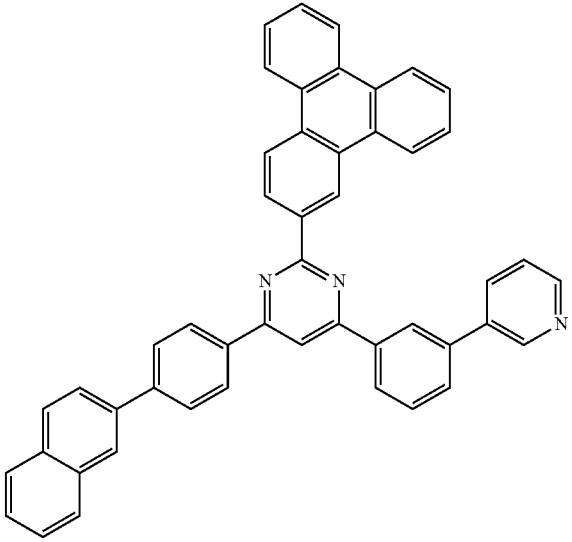
[Chemical Formula 108]
(2-32)
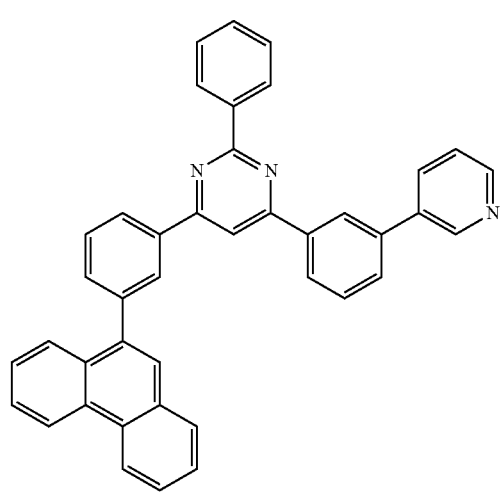

[Chemical Formula 109]
(2-33)
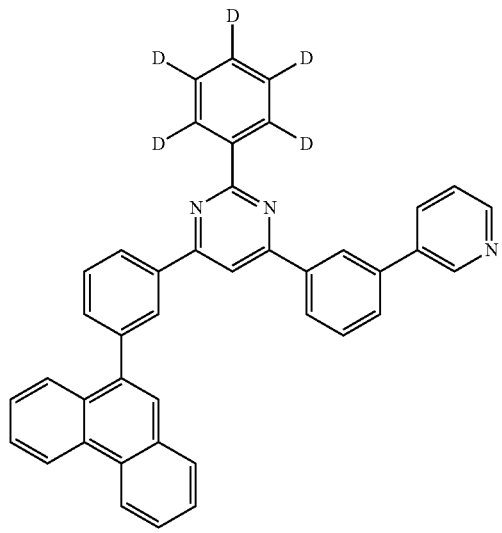
[Chemical Formula 110]
(2-34)
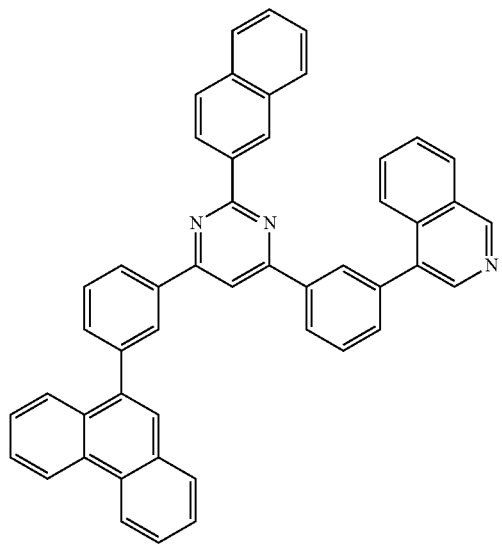
[Chemical Formula 111]
(2-35)
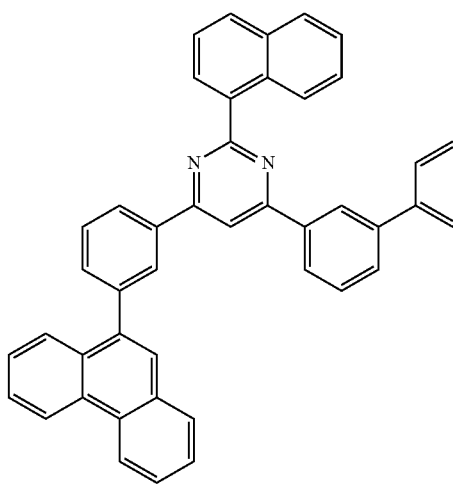
[Chemical Formula 112]
(2-36)
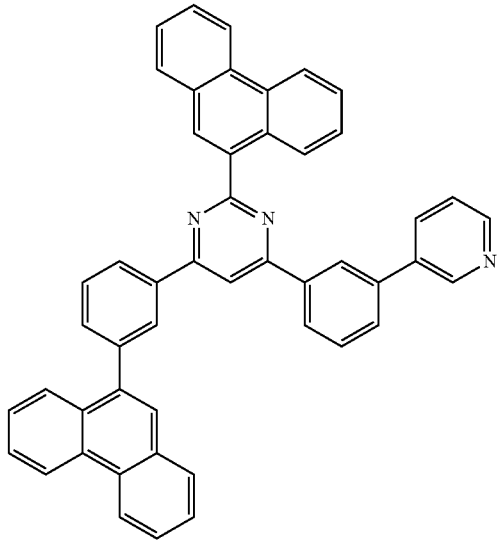

[Chemical Formula 113]
(2-37)
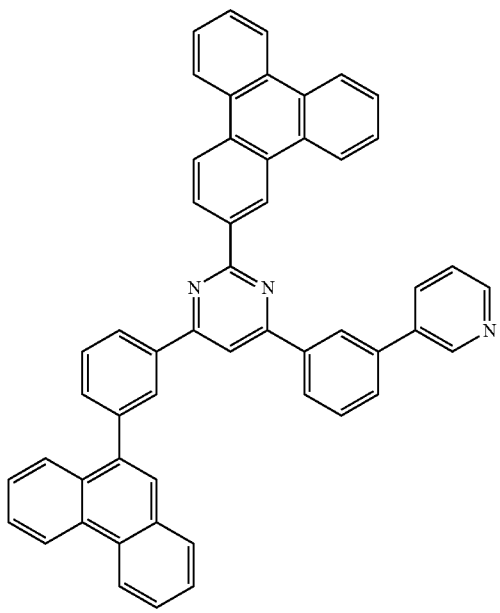
[Chemical Formula 114]
(2-38)
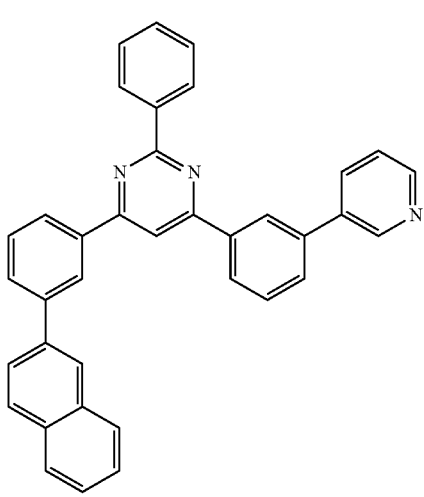
[Chemical Formula 115]
(2-39)
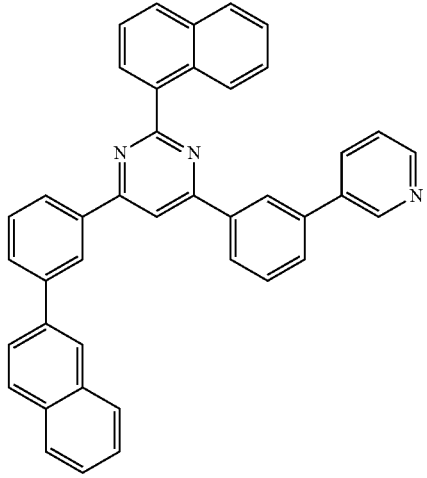
[Chemical Formula 116]
(2-40)
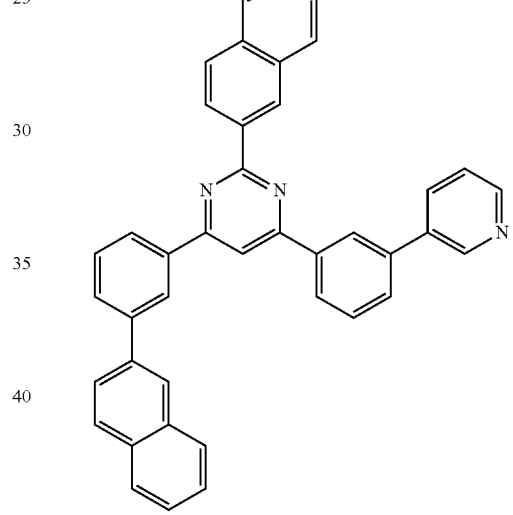
[Chemical Formula 117]
(2-41)
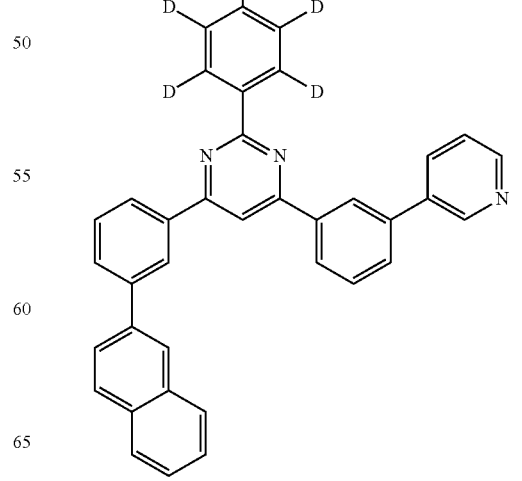

[Chemical Formula 118]
(2-42)
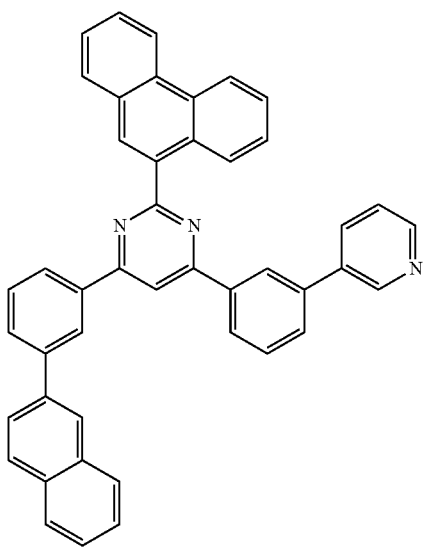
[Chemical Formula 119]
(2-43)
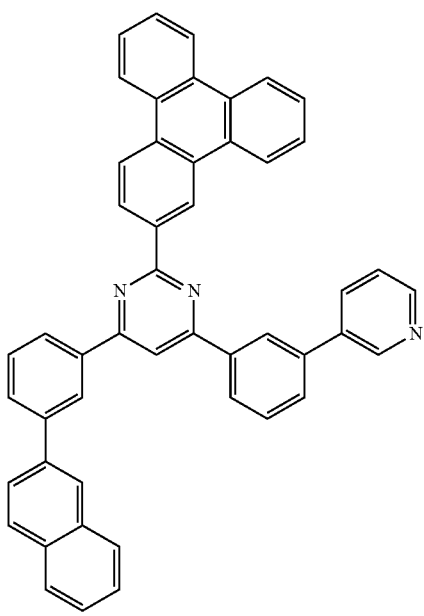
[Chemical Formula 120]
(2-44)
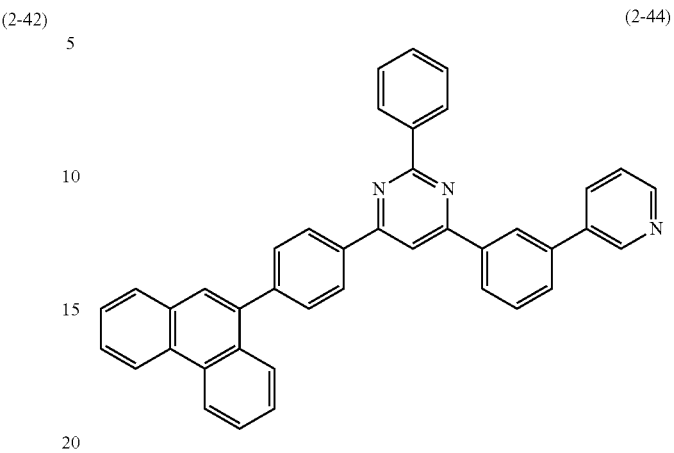
[Chemical Formula 121]
(2-45)
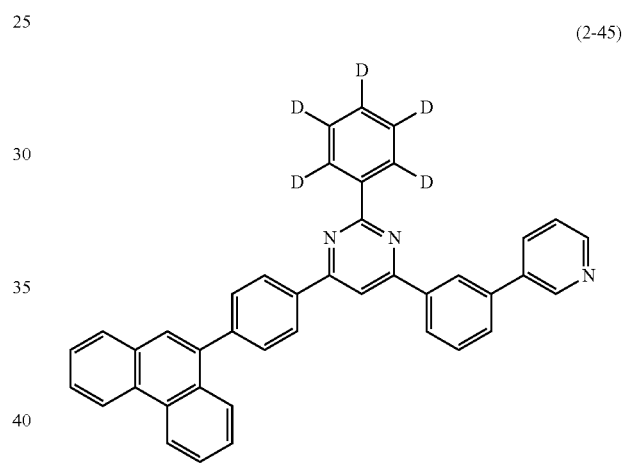
[Chemical Formula 122]
(2-46)
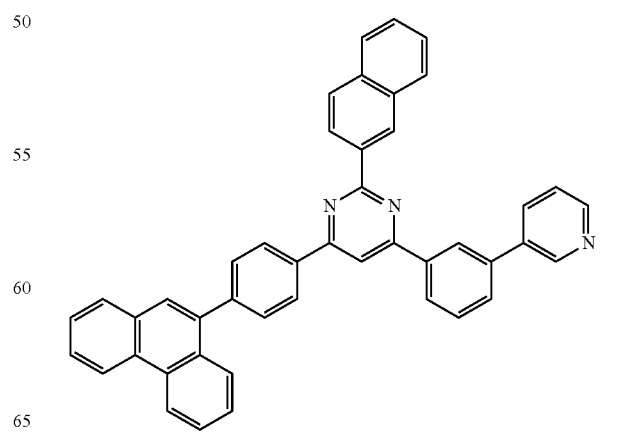

-continued
[Chemical Formula 123]
(2-47)
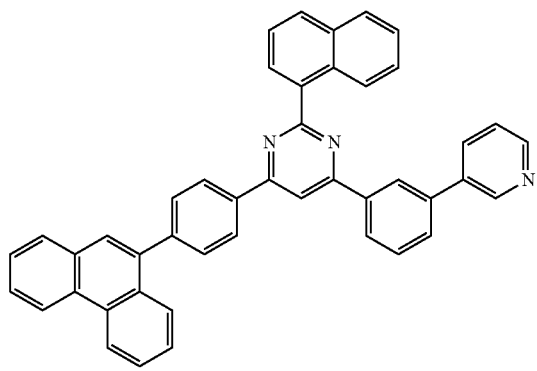
[Chemical Formula 124]
(2-48)
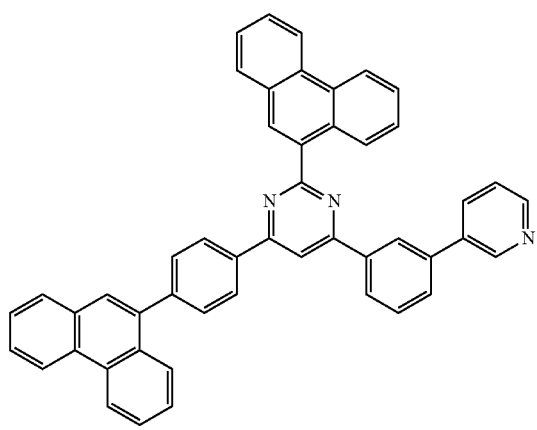
[Chemical Formula 125]
(2-49)
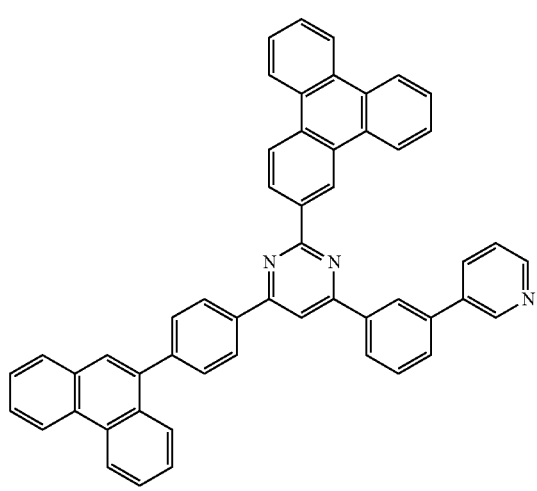
-continued
[Chemical Formula 126]
(2-50)
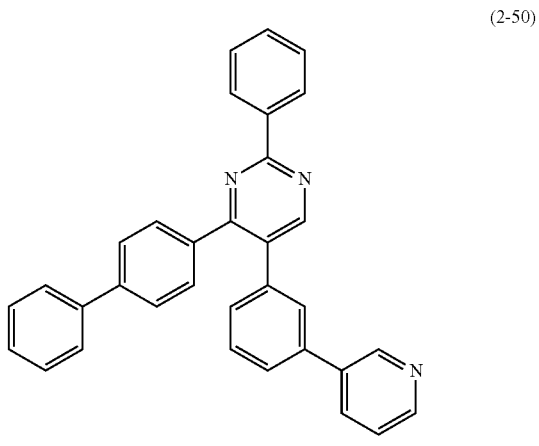
[Chemical Formula 127]
(2-51)
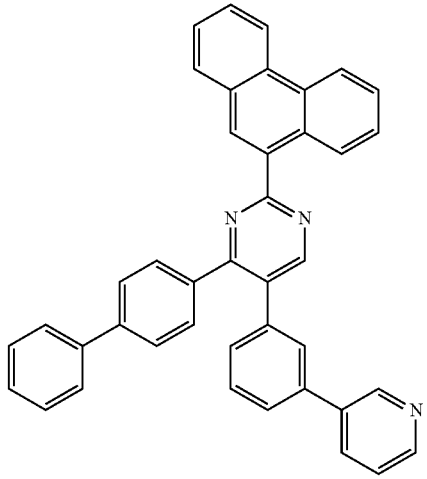
[Chemical Formula 128]
(2-52)
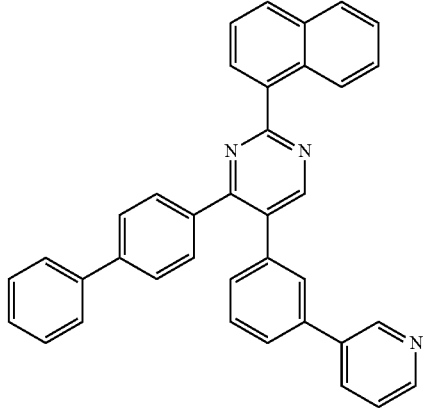

[Chemical Formula 129]
(2-53)
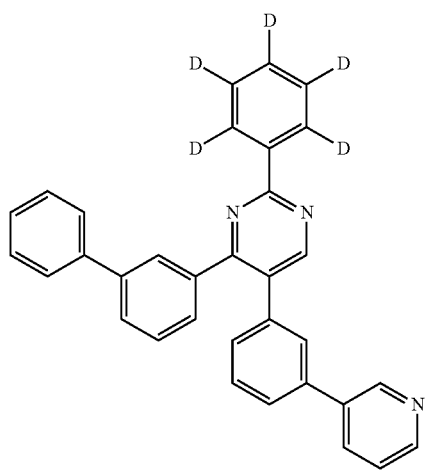
[Chemical Formula 130]
(2-54)
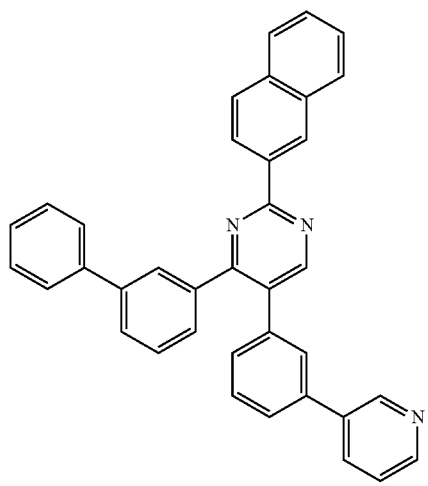
[Chemical Formula 131]
(2-55)
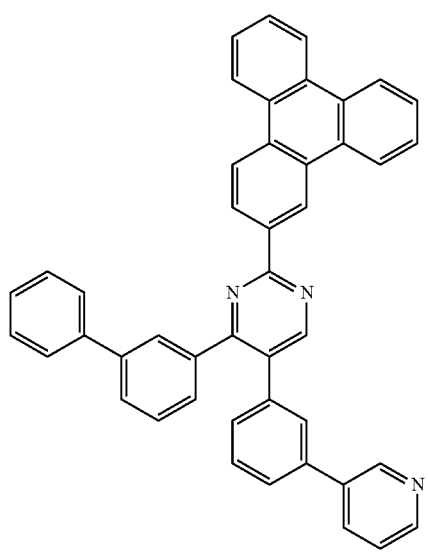
[Chemical Formula 132]
(2-56)
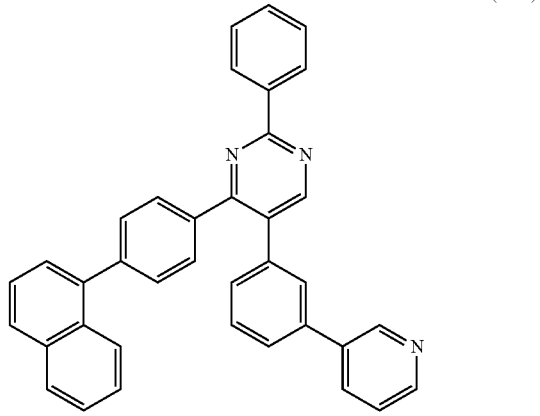
[Chemical Formula 133]
(2-57)
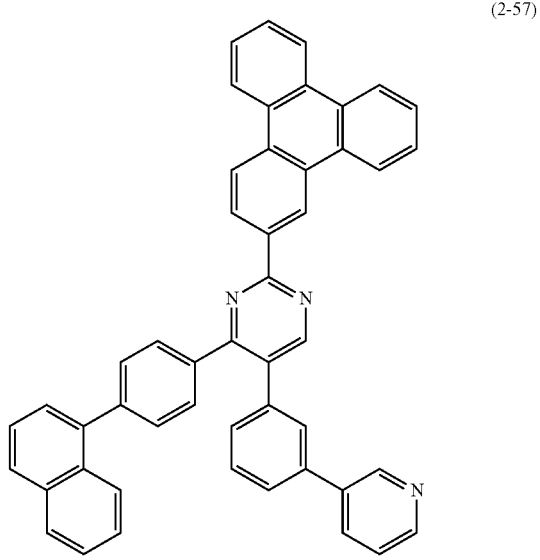
[Chemical Formula 134]
(2-58)
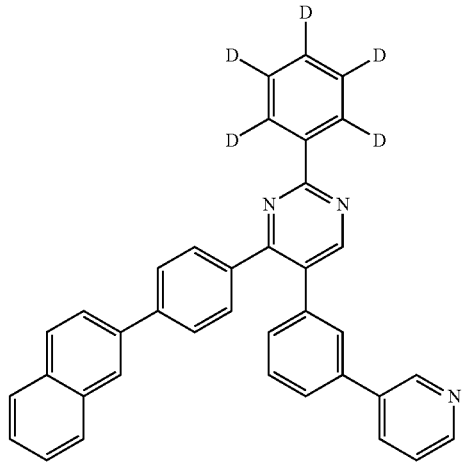

[Chemical Formula 135]
(2-59)
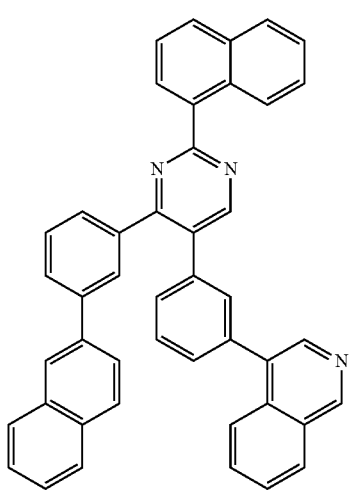
[Chemical Formula 136]
(2-60)
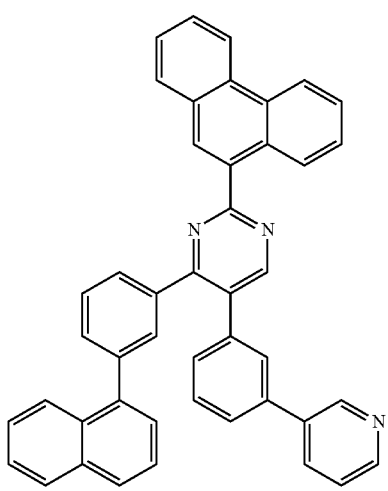
[Chemical Formula 137]
(2-61)
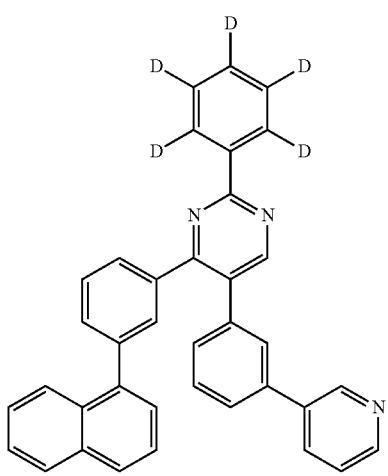
[Chemical Formula 138]
(2-62)
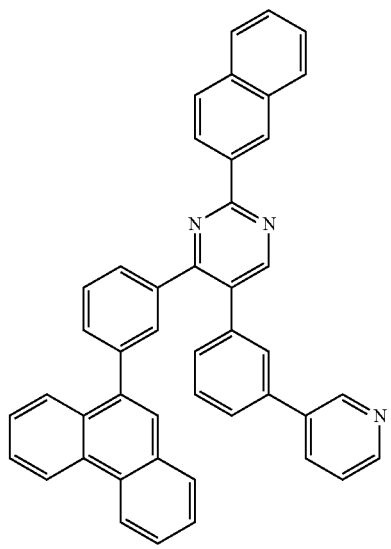
[Chemical Formula 139]
(2-63)

-continued
[Chemical Formula 140]
(2-64)
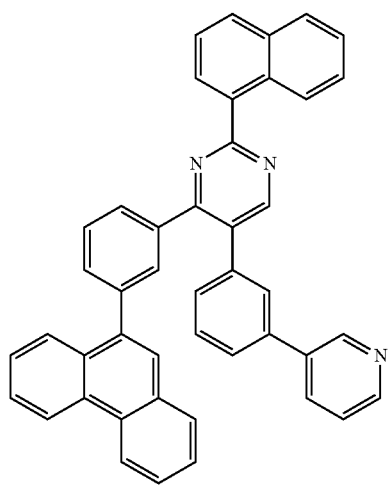
[Chemical Formula 141]
(2-65)
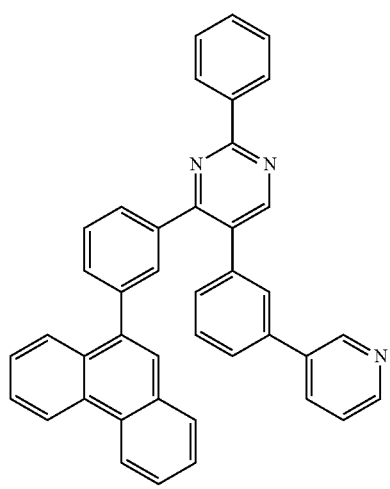
[Chemical Formula 142]
(2-66)
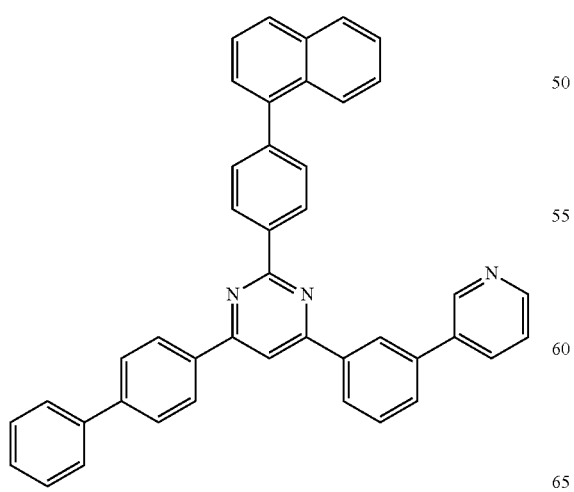
-continued
[Chemical Formula 143]
(2-67)
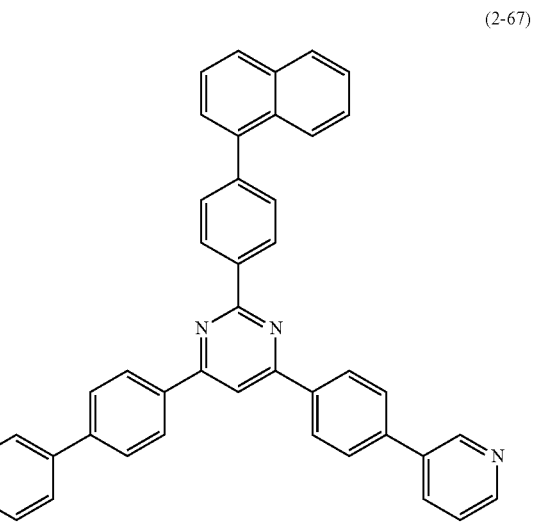
[Chemical Formula 144]
(2-68)
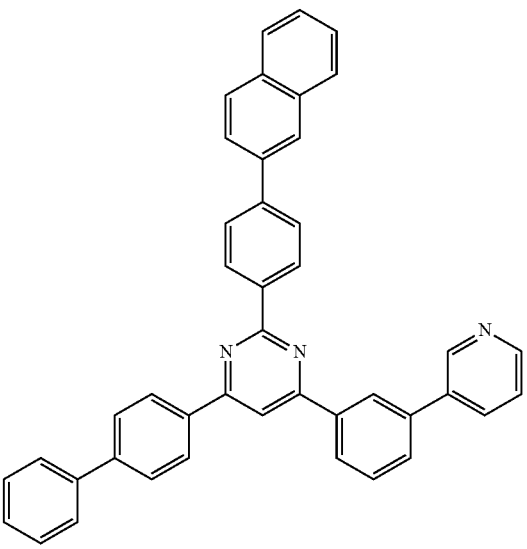

[Chemical Formula 145]
(2-69)
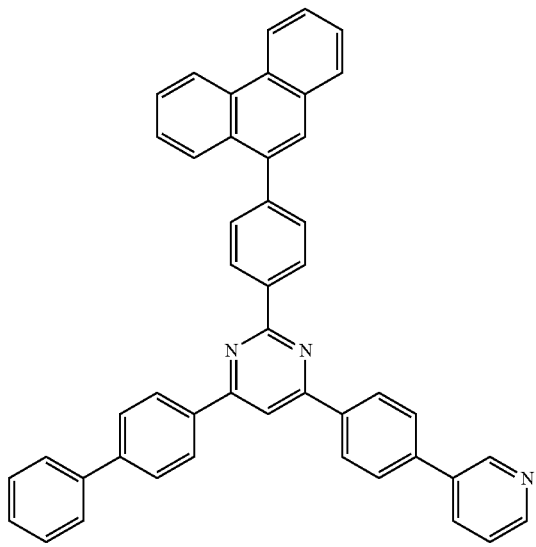
[Chemical Formula 146]
(2-70)
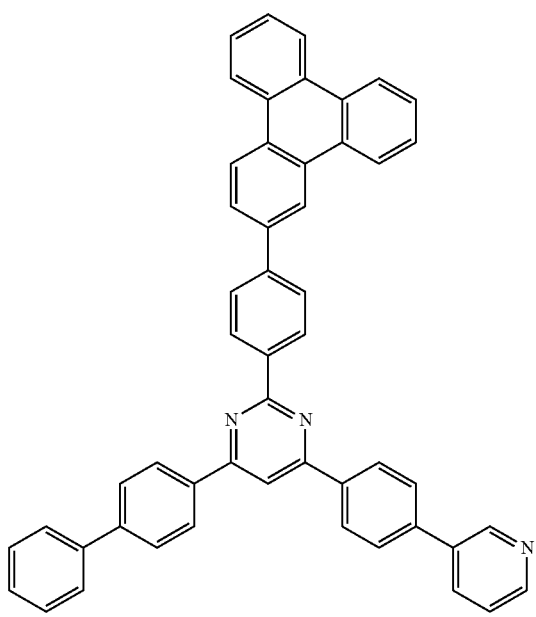
[Chemical Formula 147]
(2-71)
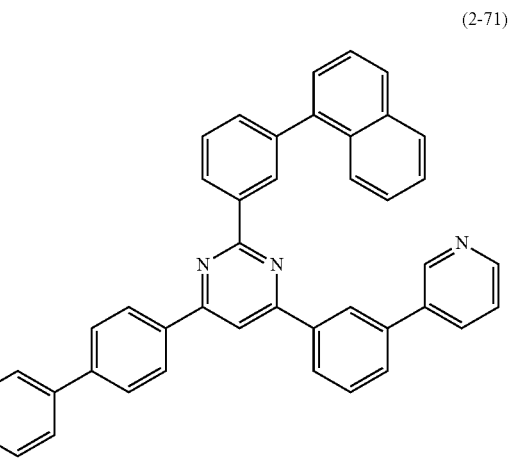
[Chemical Formula 148]
(2-72)
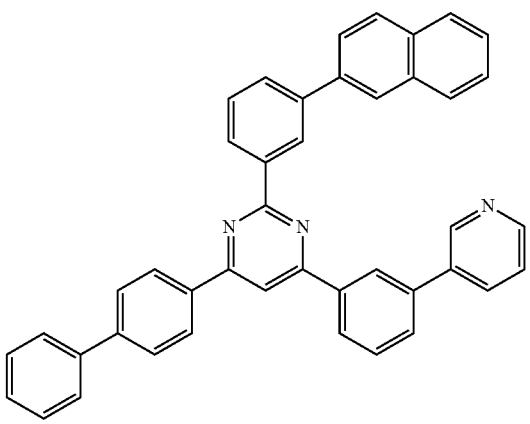
[Chemical Formula 149]
(2-73)
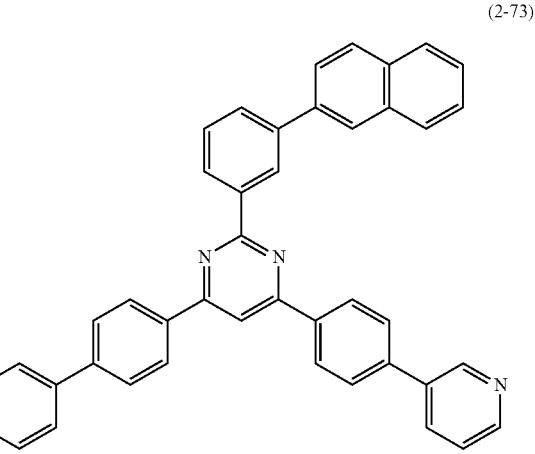

[Chemical Formula 150]
(2-74)
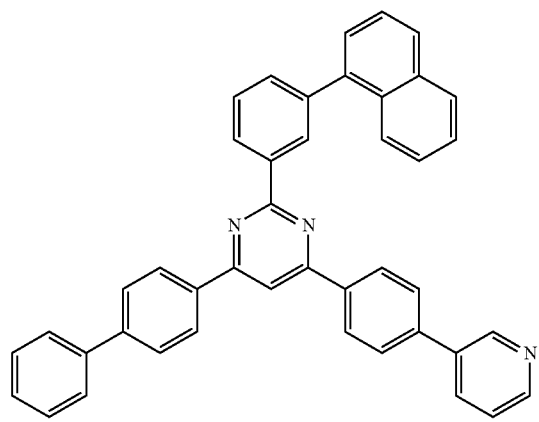
[Chemical Formula 152]
(2-76)
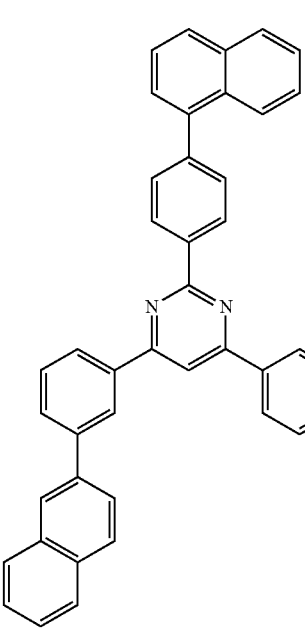
[Chemical Formula 151]
(2-75)
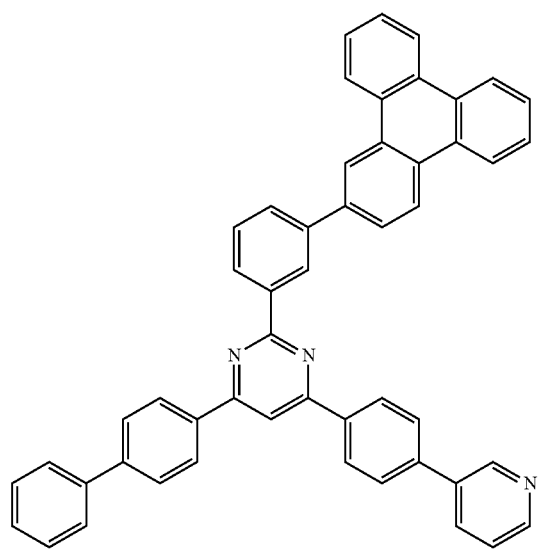
[Chemical Formula 153]
(2-77)
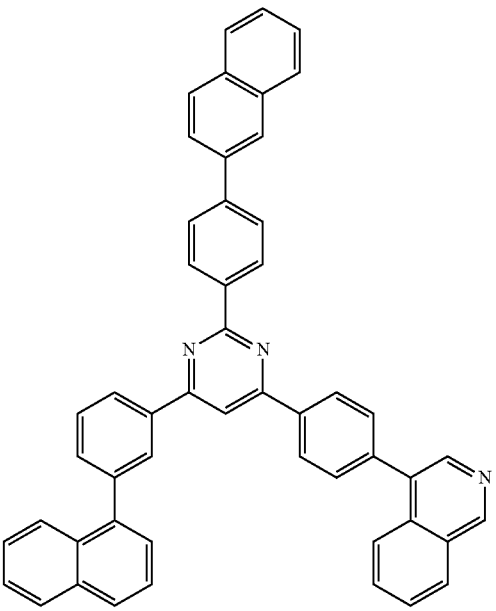

[Chemical Formula 154]
(2-78)
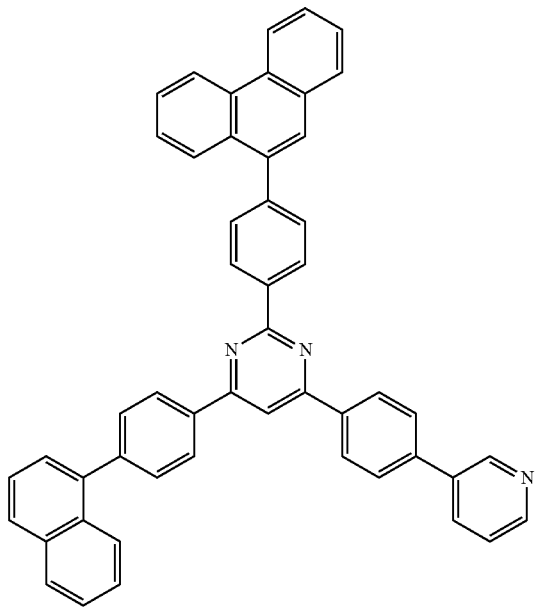
[Chemical Formula 155]]
(2-79)
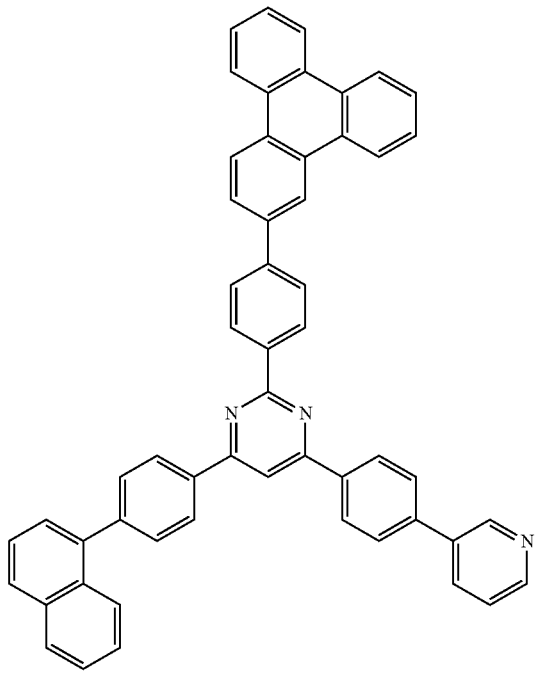
[Chemical Formula 156]
(2-80)
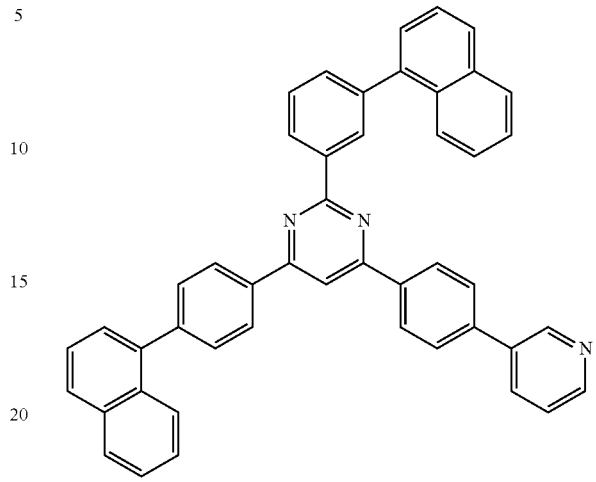
[Chemical Formula 157]
(2-81)
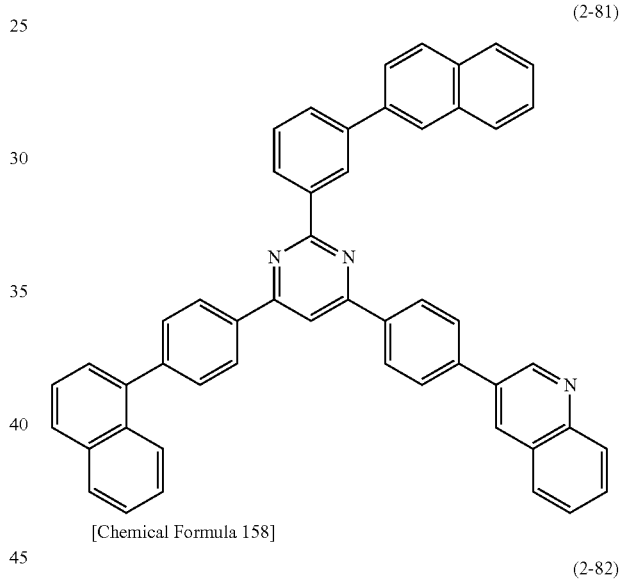
[Chemical Formula 158]
(2-82)
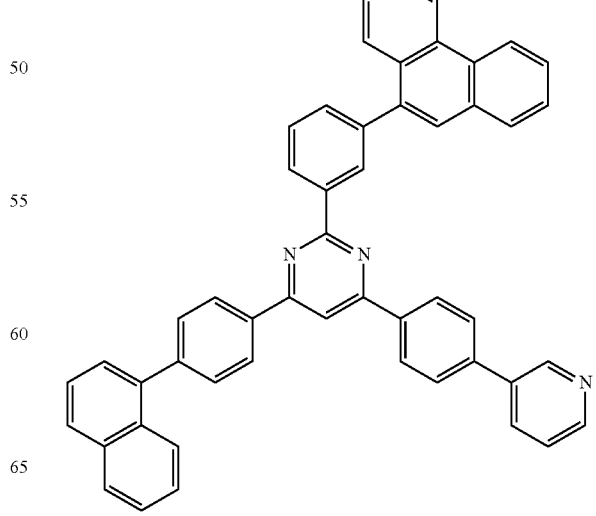

[Chemical Formula 159]
(2-83)
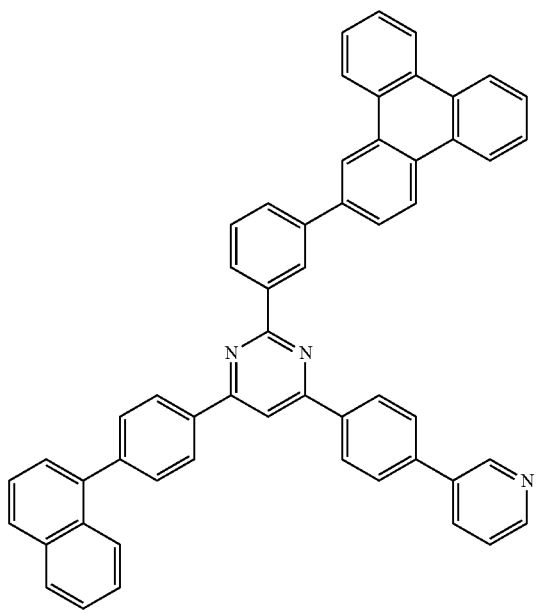
[Chemical Formula 160]
(2-84)
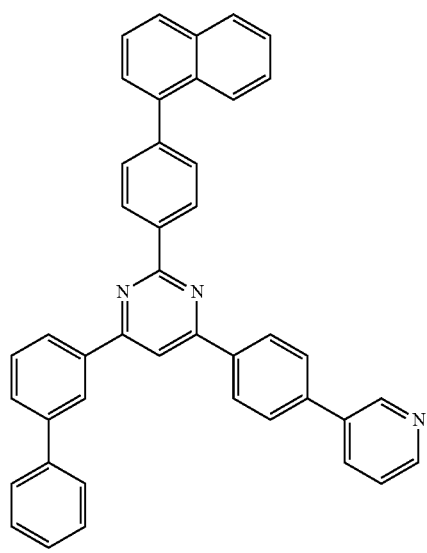
[Chemical Formula 161]
(2-85)
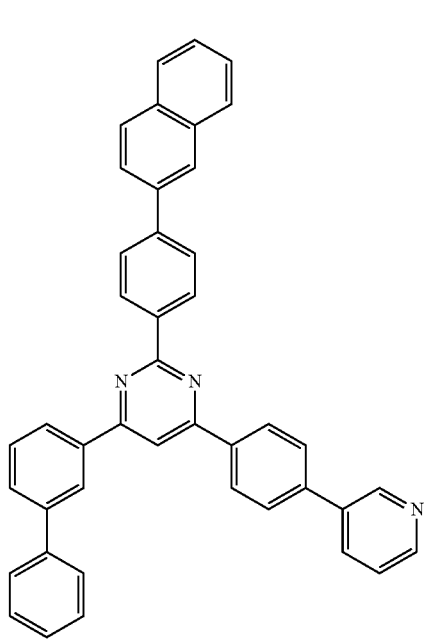
[Chemical Formula 162]
(2-86)
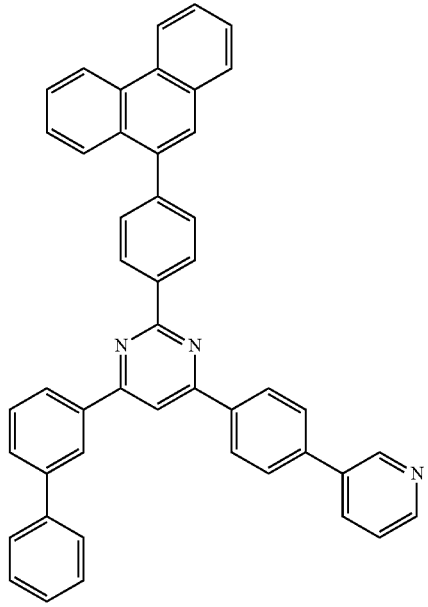

[Chemical Formula 163]
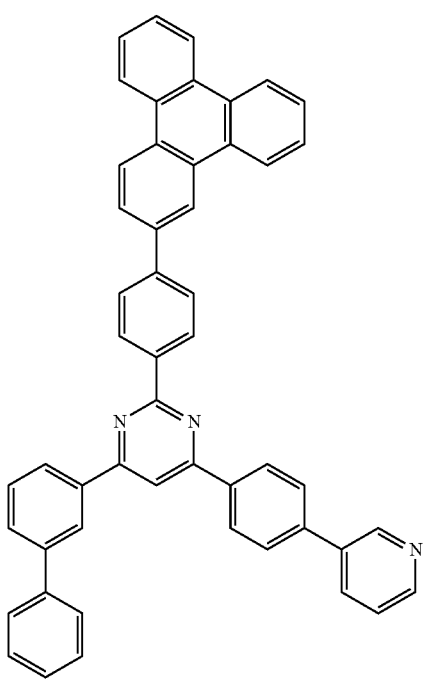
(2-87)
[Chemical Formula 164]
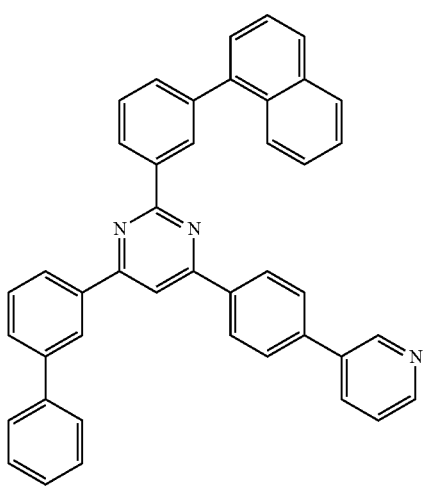
(2-88)
[Chemical Formula 165]
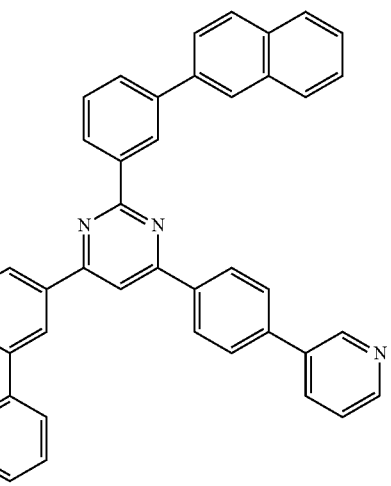
(2-89)
[Chemical Formula 166]
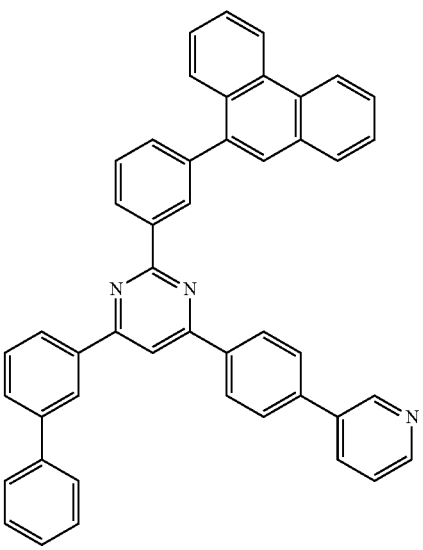
(2-90)

[Chemical Formula 167]
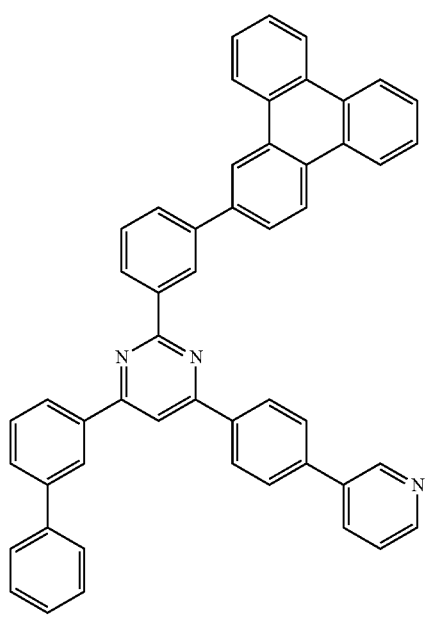
(2-91)
[Chemical Formula 168]
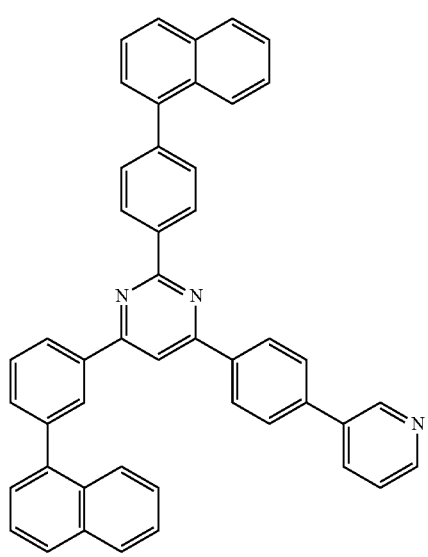
(2-92)
[Chemical Formula 169]
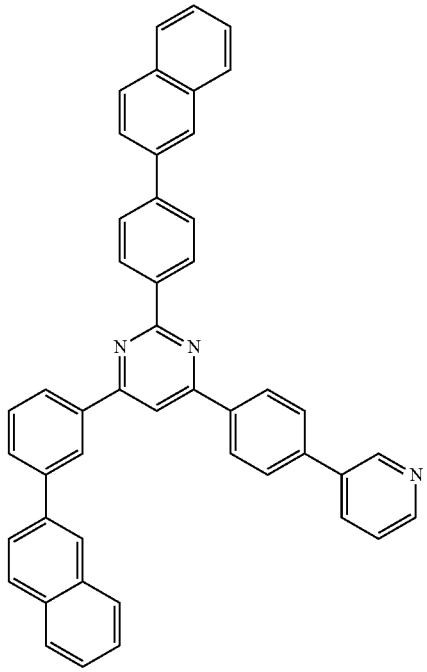
(2-93)
[Chemical Formula 170]
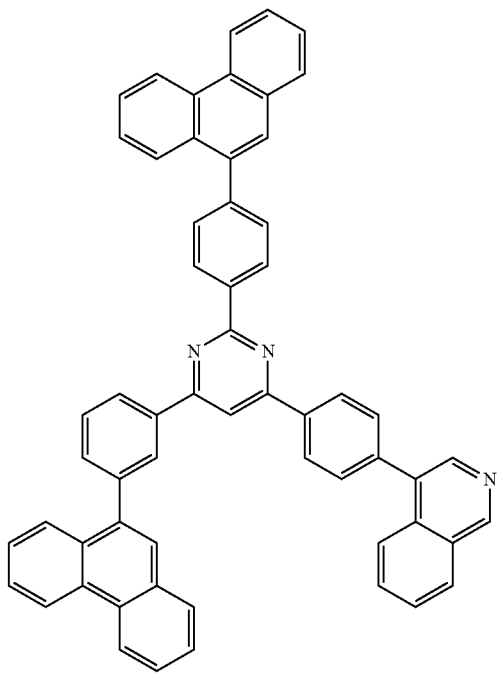
(2-94)

[Chemical Formula 171]
(2-95)
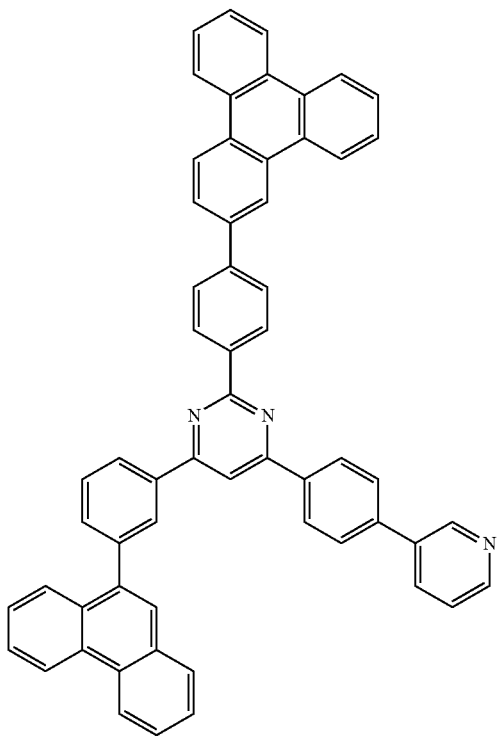
[Chemical Formula 173]
(2-97)
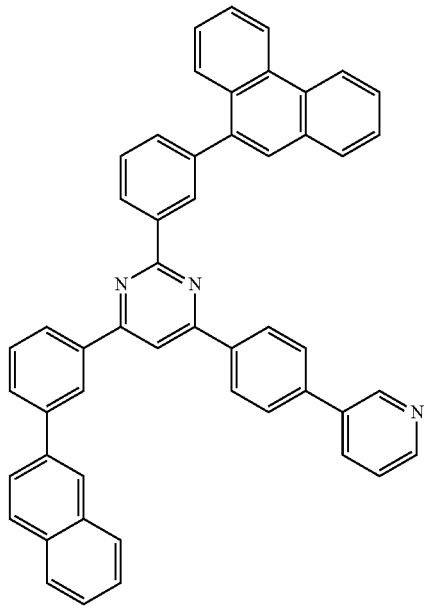
[Chemical Formula 172]
(2-96)
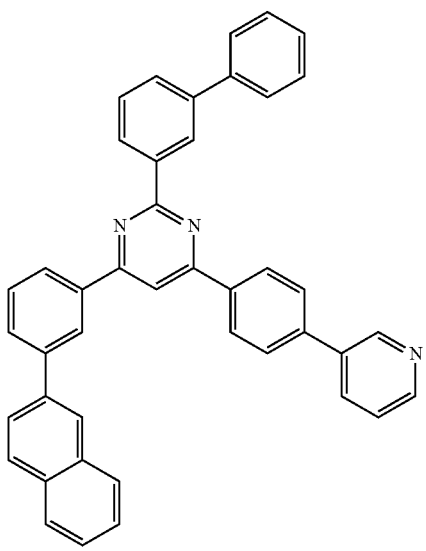
[Chemical Formula 174]
(2-98)

[Chemical Formula 175]
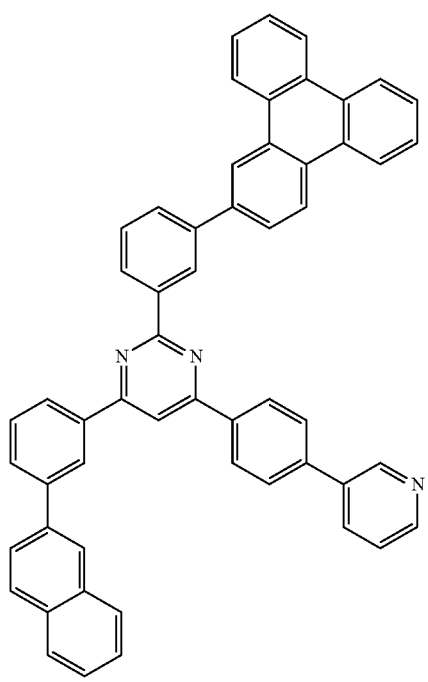
(2-99)
[Chemical Formula 176]
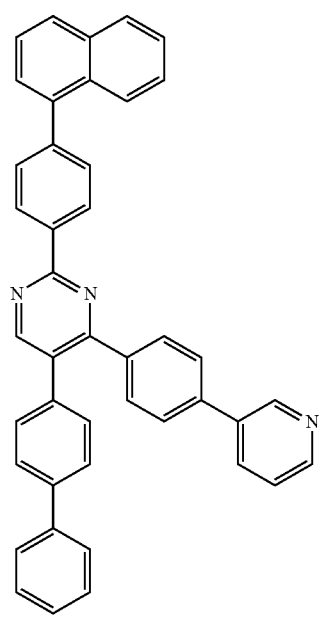
(2-100)
[Chemical Formula 177]
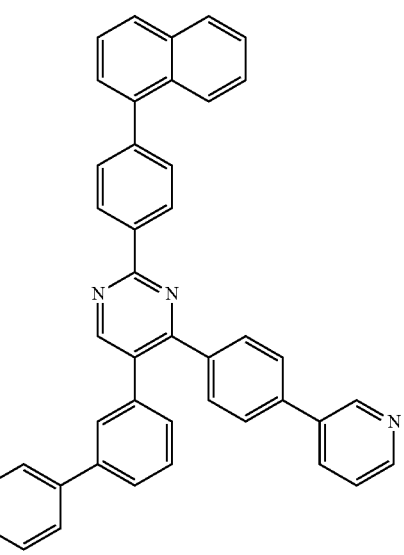
(2-101)
[Chemical Formula 178]
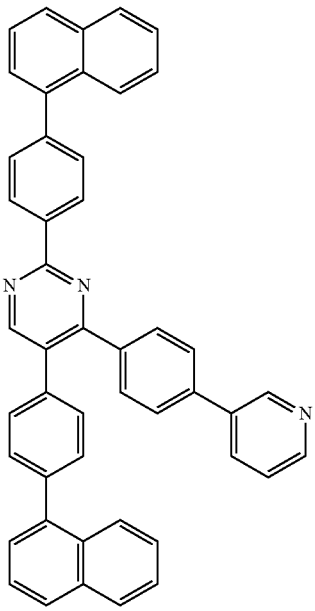
(2-102)

[Chemical Formula 179]
(2-103)
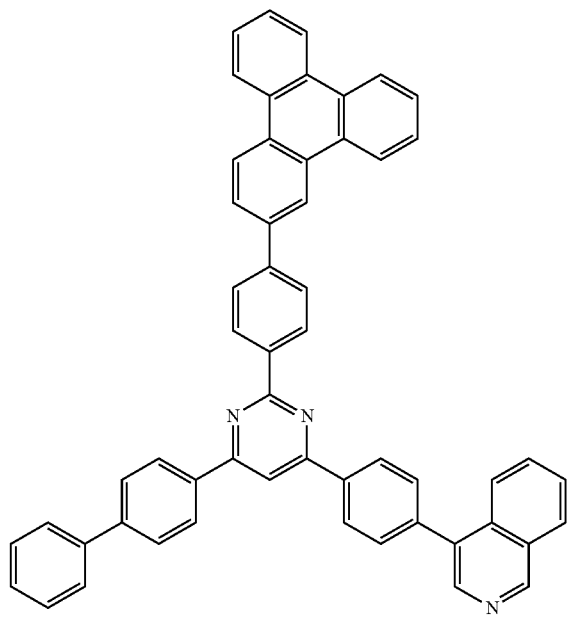
[Chemical Formula 180]
(2-104)
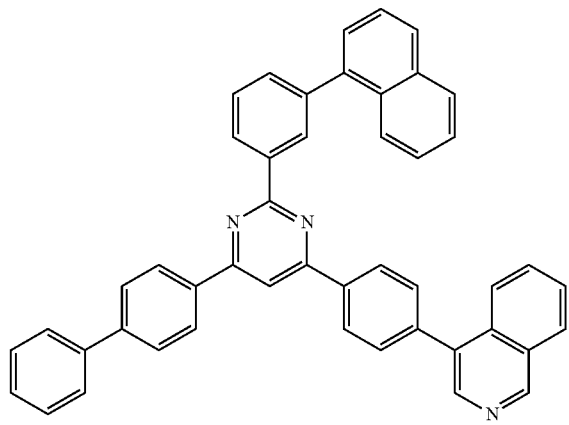
[Chemical Formula 181]
(2-105)
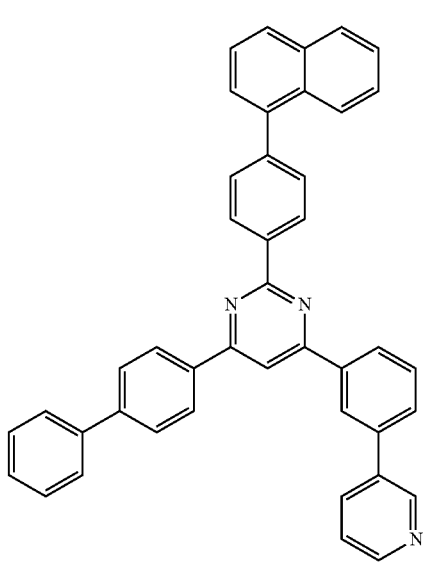
[Chemical Formula 182]
(2-106)
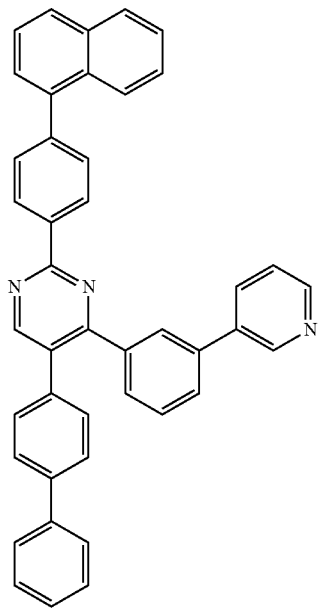

[Chemical Formula 183]
(2-107)
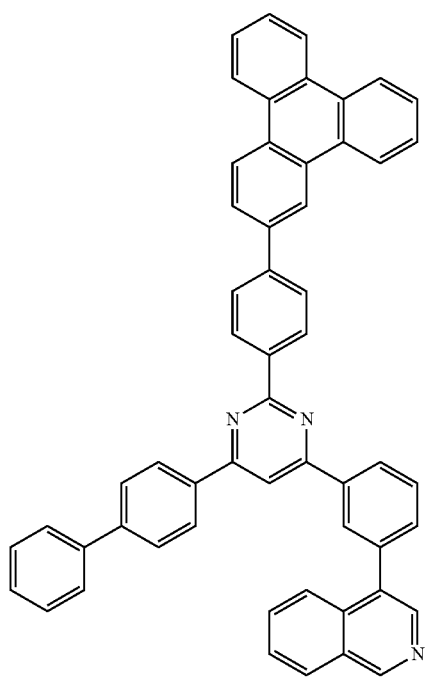
[Chemical Formula 184]
(2-108)
[Chemical Formula 185]
(2-109)
[Chemical Formula 186]
(2-110)
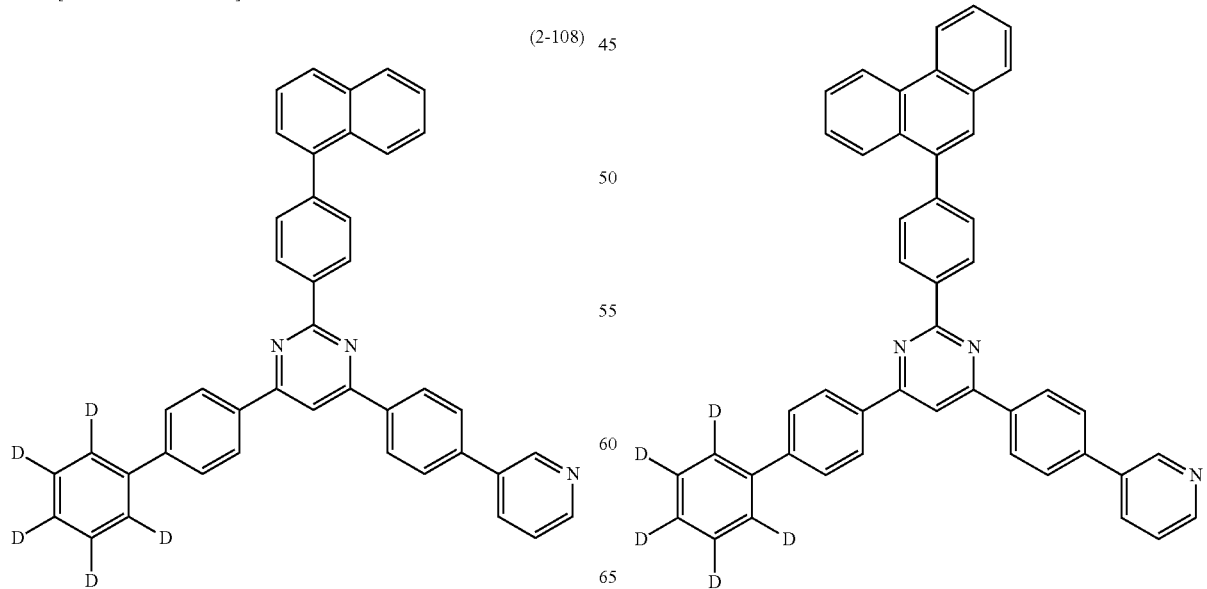

[Chemical Formula 187]
(2-111)
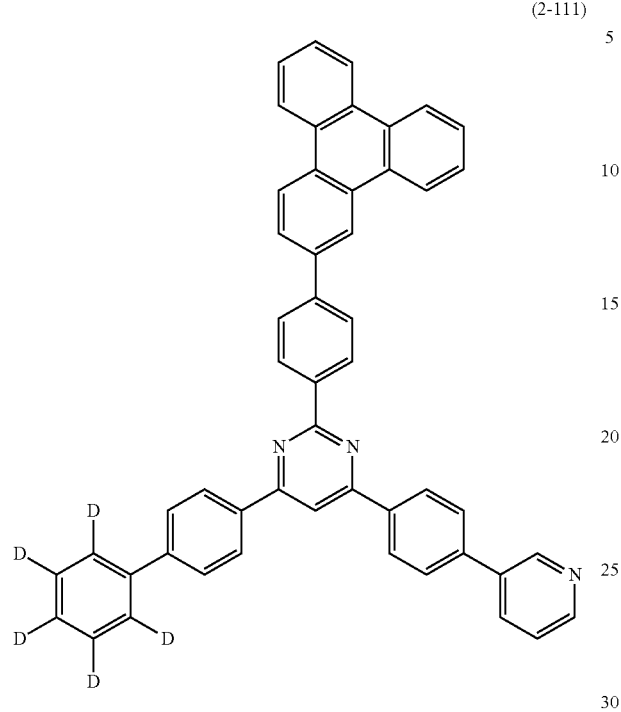
[Chemical Formula 188]
(2-112)
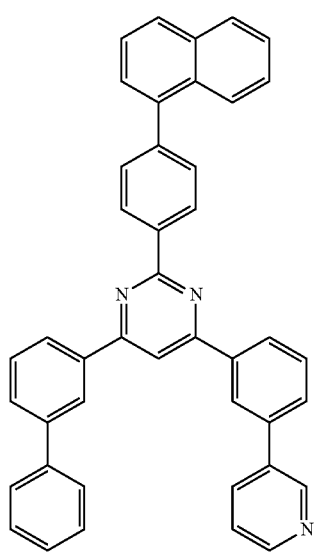
[Chemical Formula 189]
(2-113)
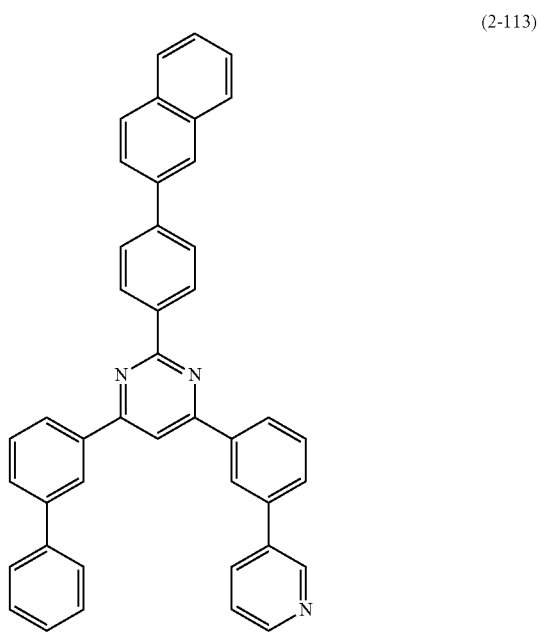
[Chemical Formula 190]
(2-114)
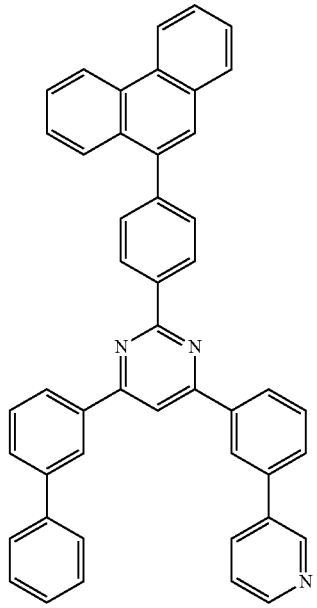

[Chemical Formula 191]
(2-115)
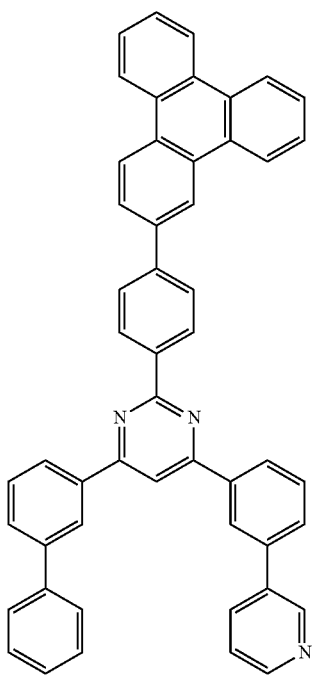
[Chemical Formula 192]
(2-116)
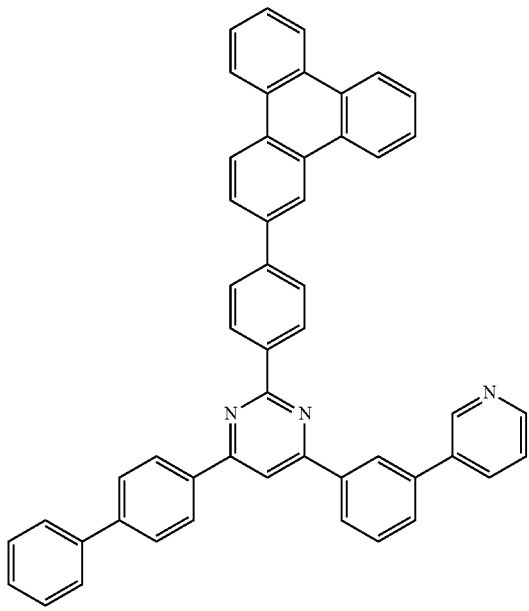
[Chemical Formula 193]
(2-117)
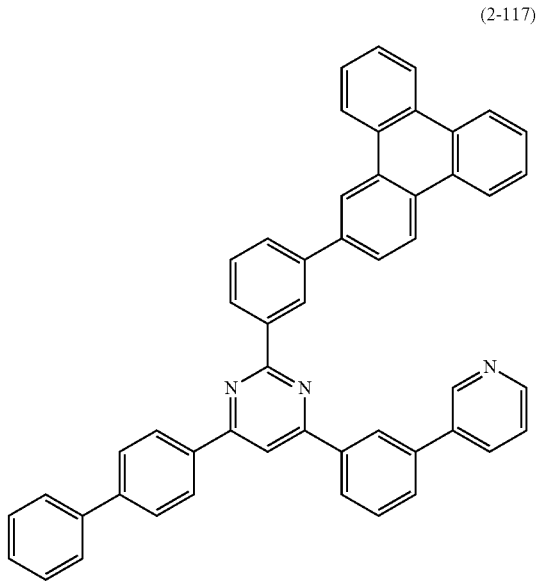
[Chemical Formula 194]
(2-118)
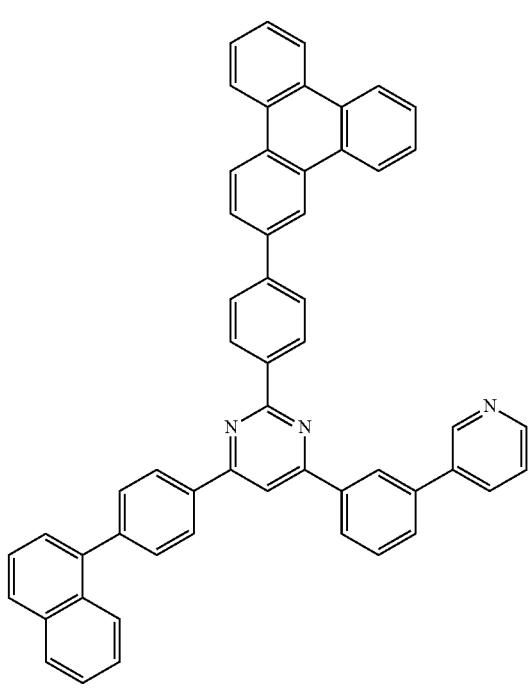

[Chemical Formula 195]
(2-119)
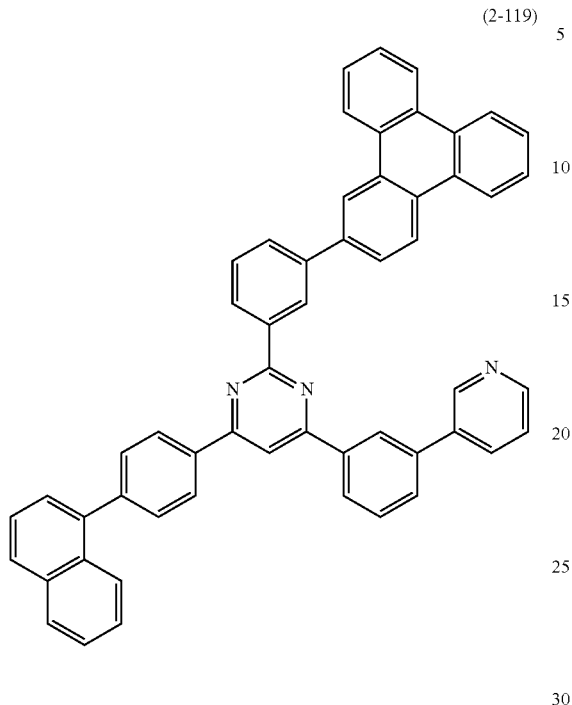
[Chemical Formula 196]
(2-120)
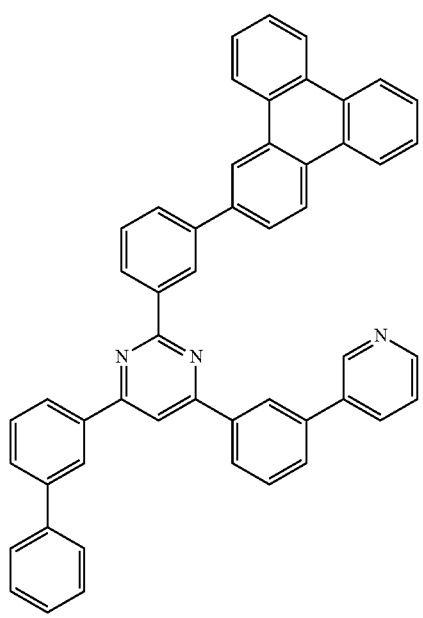
[Chemical Formula 197]
(2-121)
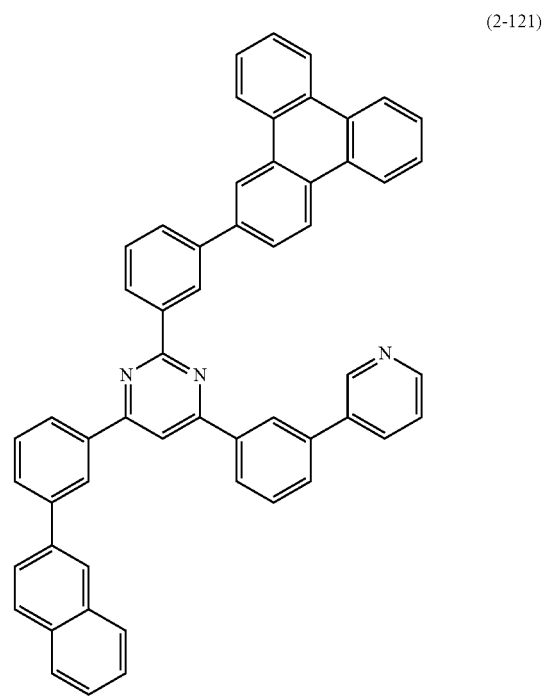
[Chemical Formula 198]
(2-122)
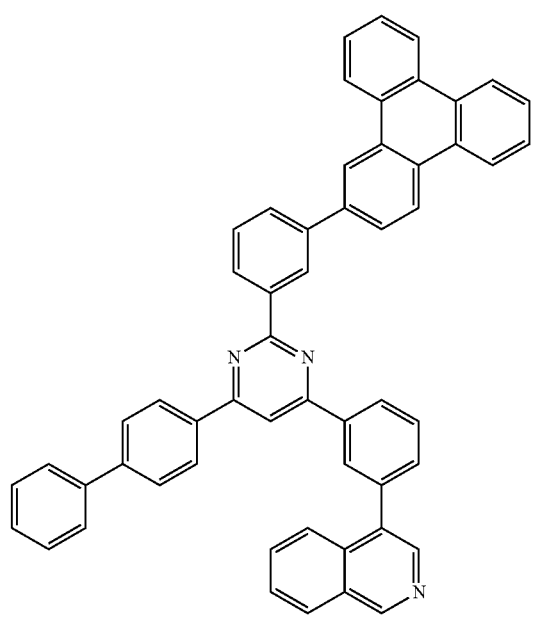

[Chemical Formula 199]

(2-123)

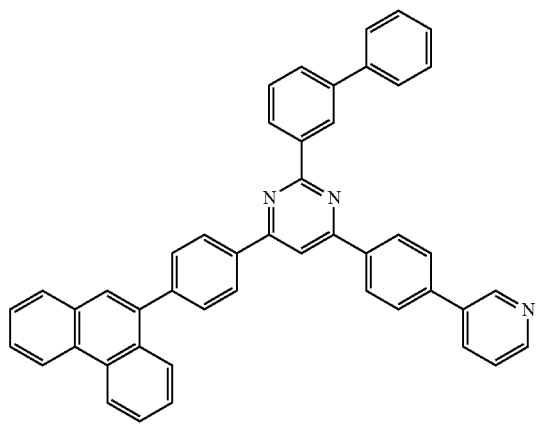

[Chemical Formula 200]

(2-124)

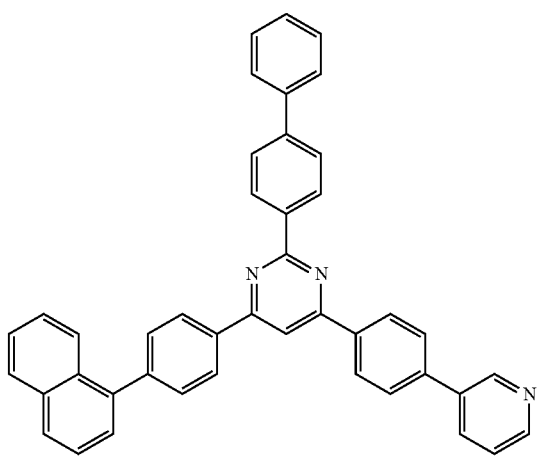

[Chemical Formula 201]

(2-125)

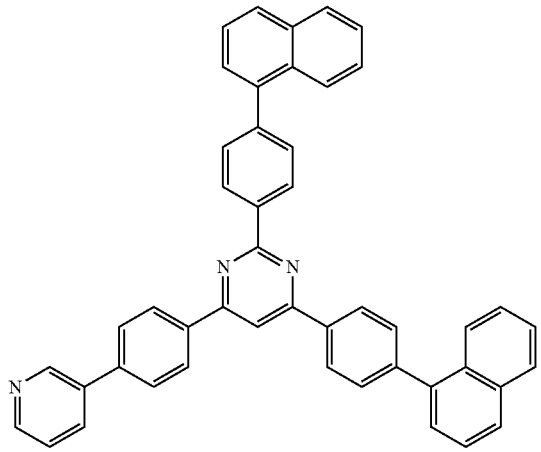

[Chemical Formula 202]

(2-126)

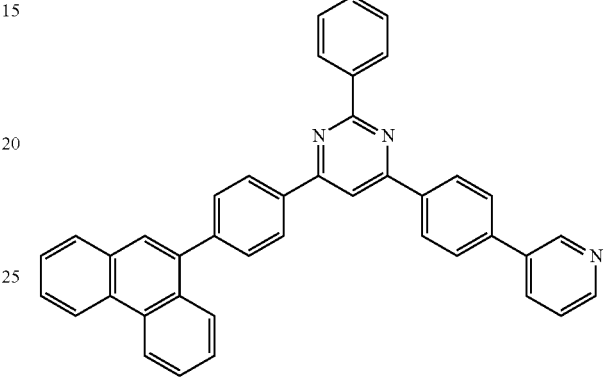

The compounds having a pyrimidine ring structure described above can be synthesized by a known method (refer to PTLs 6 to 7, for example).

In the organic EL device of the present invention, the following presents specific examples of preferred compounds among the triphenylamine derivatives of the general formula (3) having two triphenylamine skeletons as a whole molecule and preferably used in the first hole transport layer in the case where the hole transport layer has a two-layer structure of the first hole transport layer and the second hole transport layer. The present invention, however, is not restricted to these compounds.

[Chemical Formula 203]

(3-1)

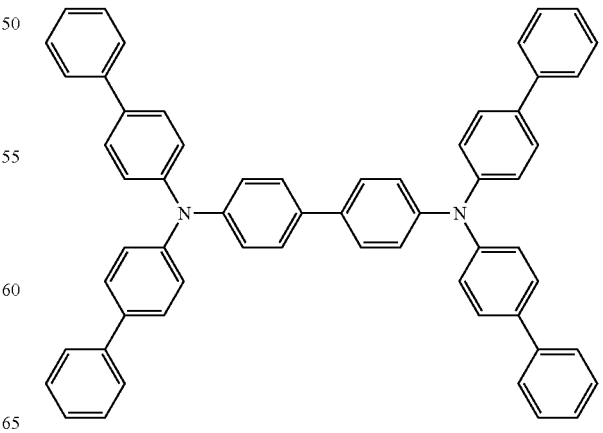

[Chemical Formula 204]
(3-2)
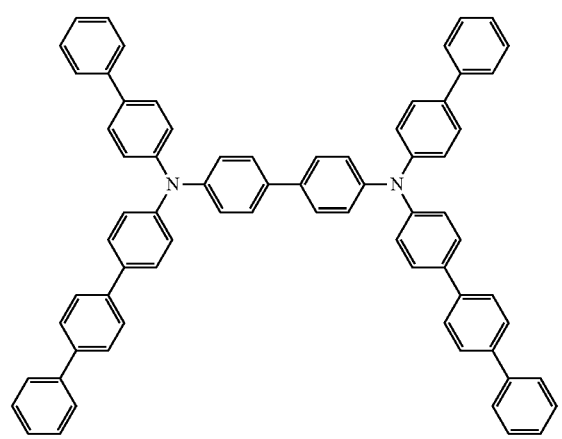
[Chemical Formula 205]
(3-3)
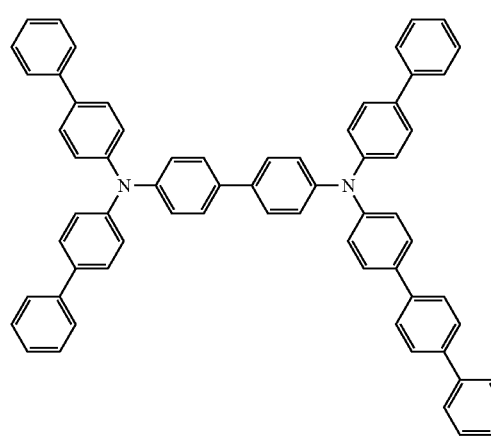
[Chemical Formula 206]
(3-4)
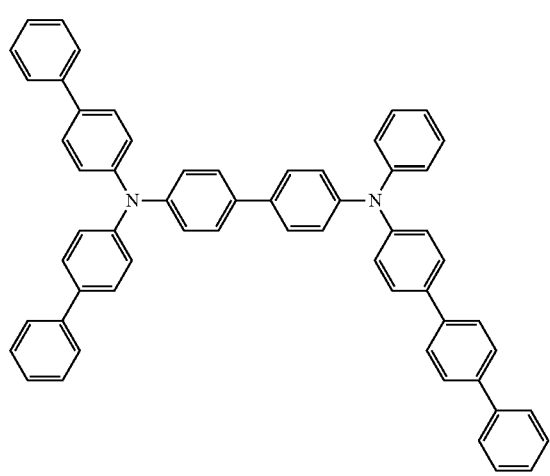
[Chemical Formula 207]
(3-5)
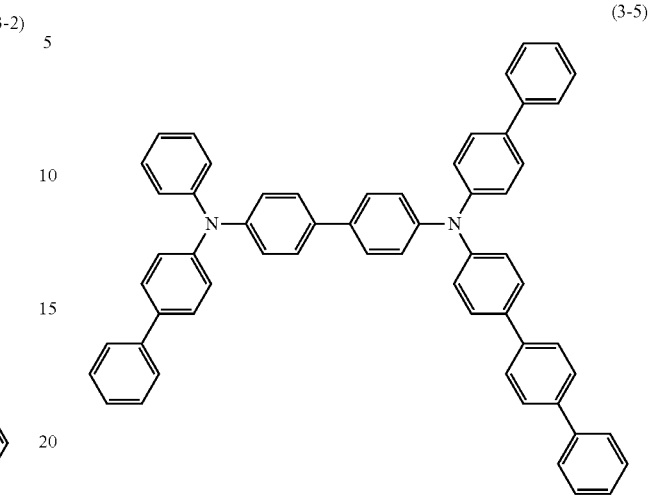
[Chemical Formula 208]
(3-6)
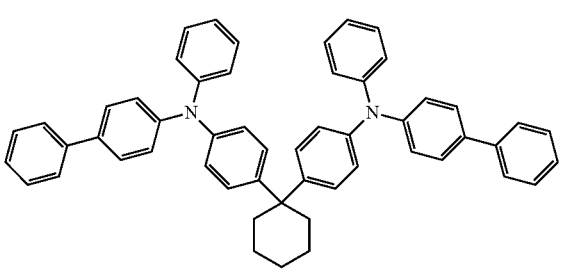
[Chemical Formula 209]
(3-7)
[Chemical Formula 210]
(3-8)

[Chemical Formula 211]
(3-9)
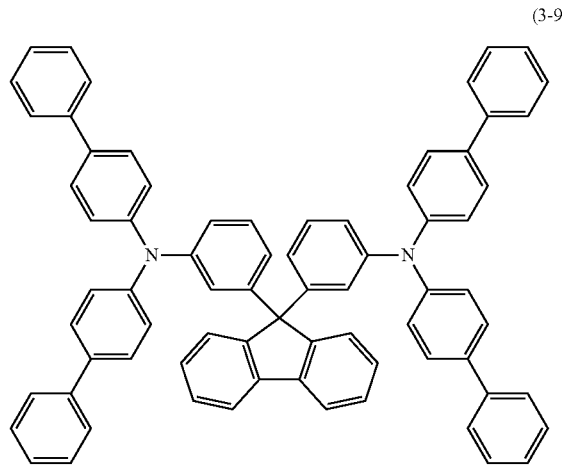
[Chemical Formula 212]
(3-10)
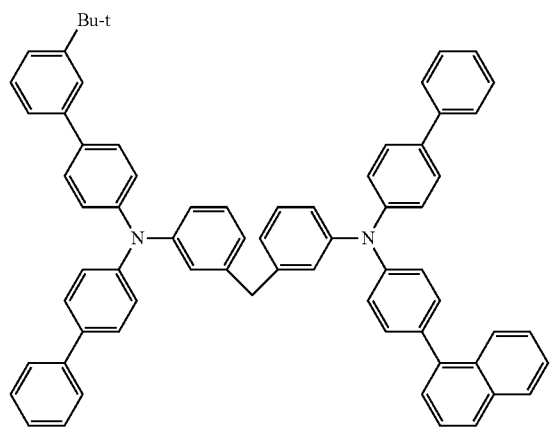
[Chemical Formula 213]
(3-11)
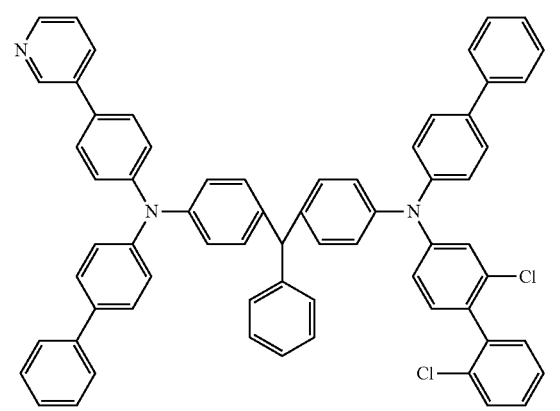
[Chemical Formula 214]
(3-12)
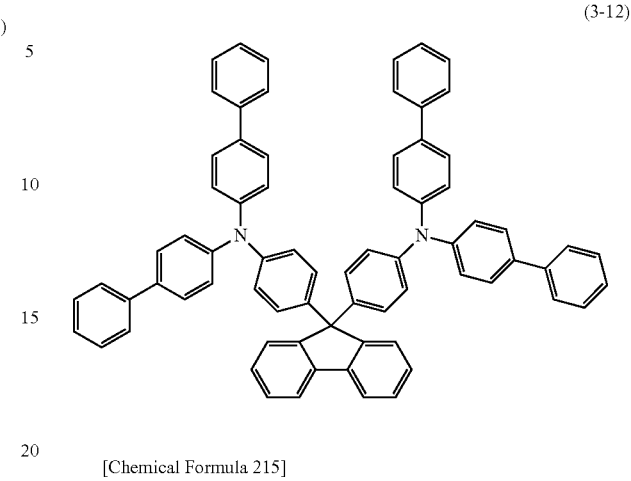
[Chemical Formula 215]
(3-13)
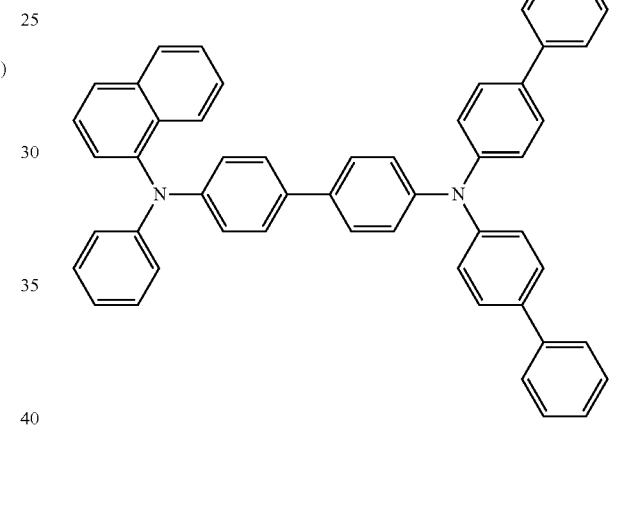
[Chemical Formula 216]
(3-14)
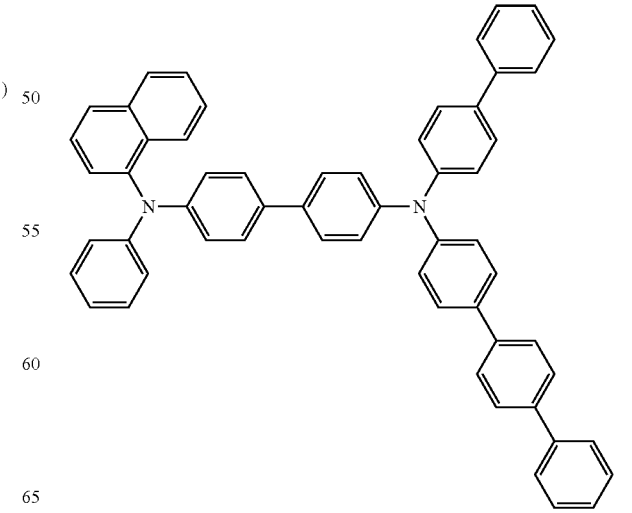

-continued
[Chemical Formula 217]
(3-15)
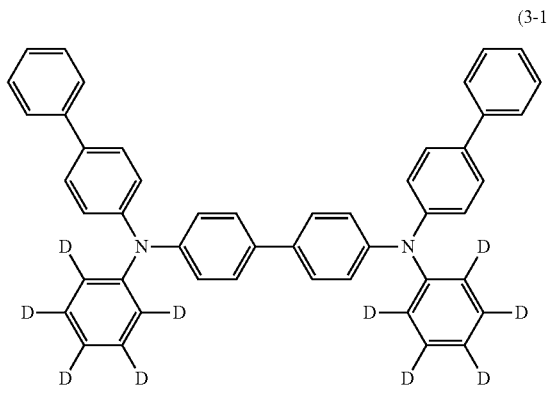
[Chemical Formula 218]
(3-16)
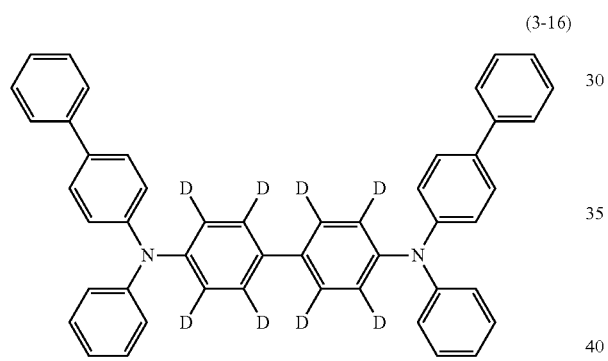
[Chemical Formula 219]
(3-17)
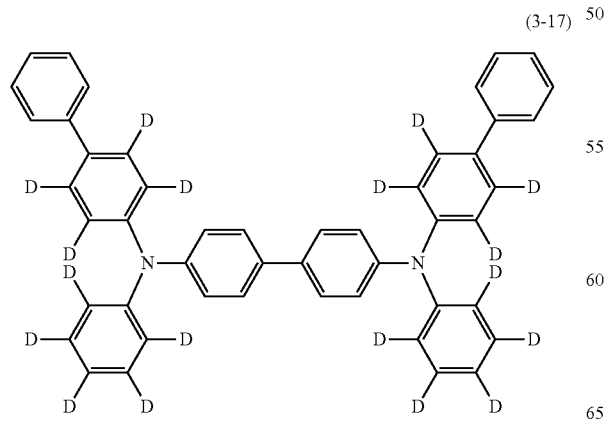
-continued
[Chemical Formula 220]
(3-18)
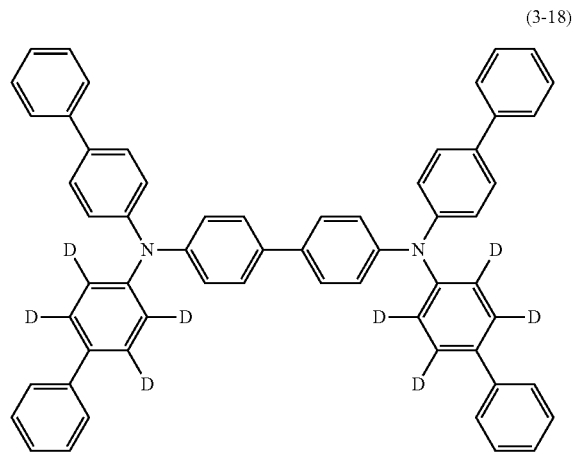
[Chemical Formula 221]
(3-19)
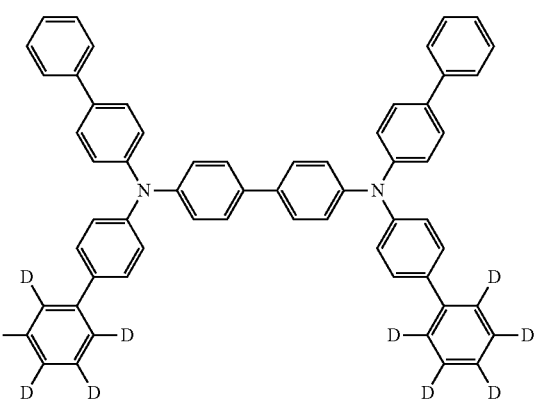
[Chemical Formula 222]
(3-20)
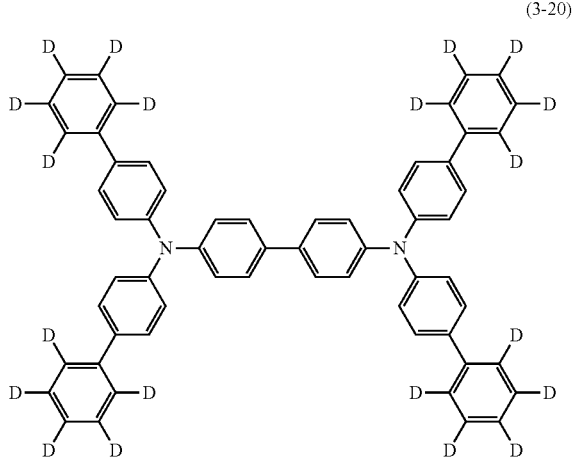

[Chemical Formula 223]

(3-21)

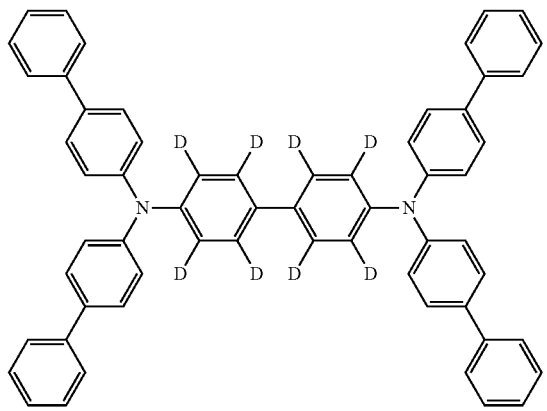

[Chemical Formula 224]

(3-22)

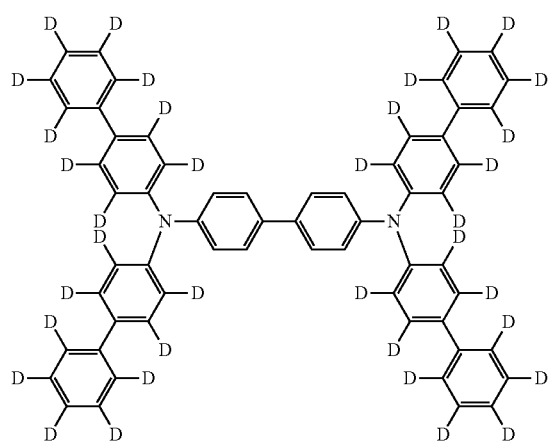

[Chemical Formula 225]

(3-23)

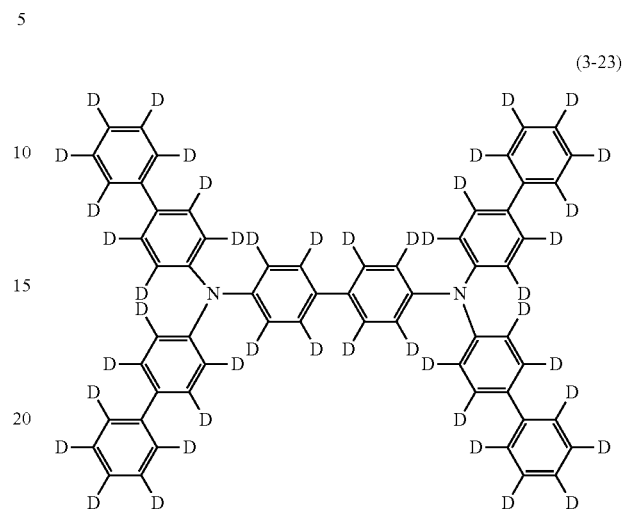

In the organic EL device of the present invention, the following presents specific examples of preferred compounds among the triphenylamine derivatives of the general formula (4) having four triphenylamine skeletons as a whole molecule and preferably used in the first hole transport layer in the case where the hole transport layer has a two-layer structure of the first hole transport layer and the second hole transport layer. The present invention, however, is not restricted to these compounds.

[Chemical Formula 226]

(4-1)

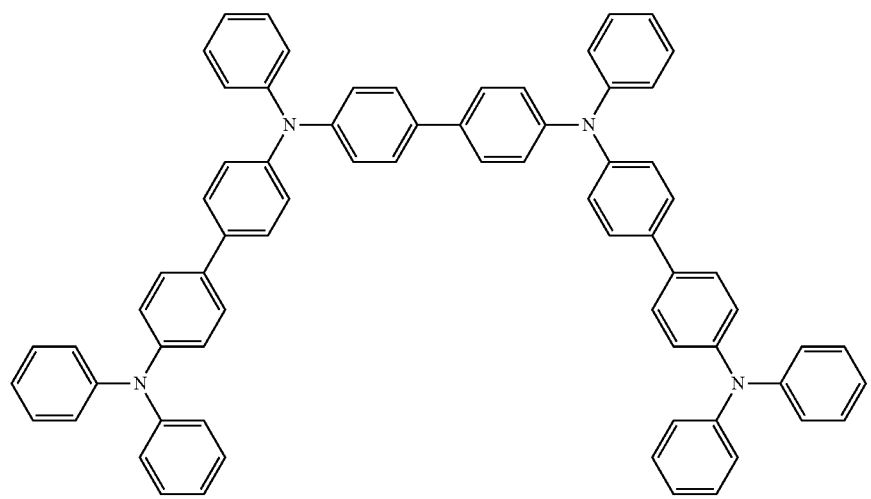

-continued
[Chemical Formula 227]
(4-2)
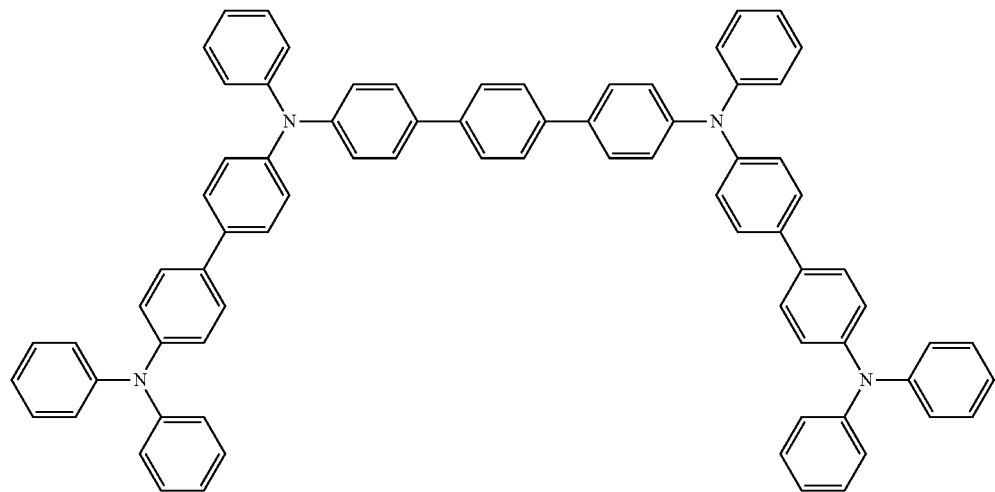
[Chemical Formula 228]
(4-3)
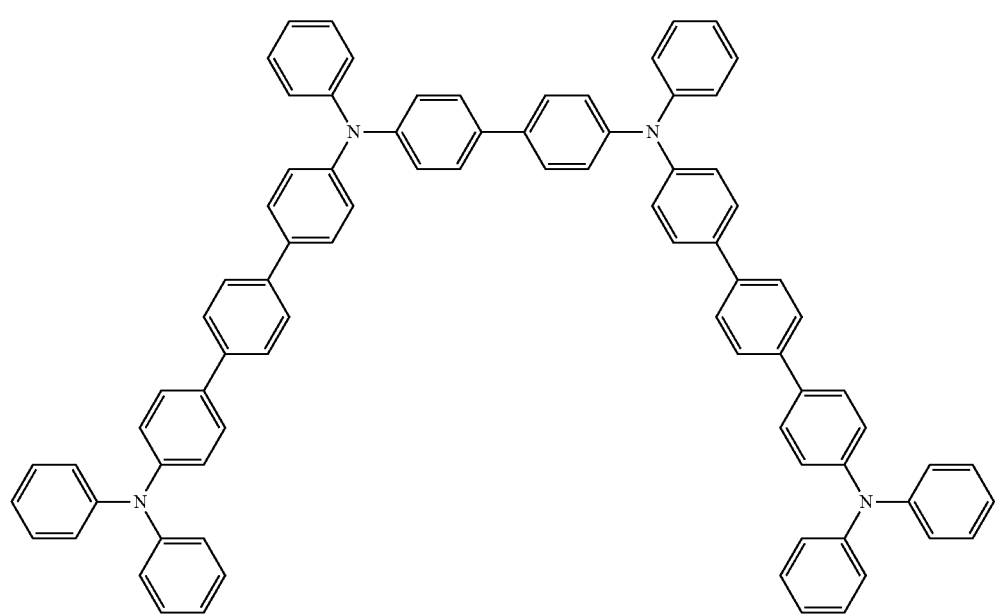

[Chemical Formula 229]
(4-4)
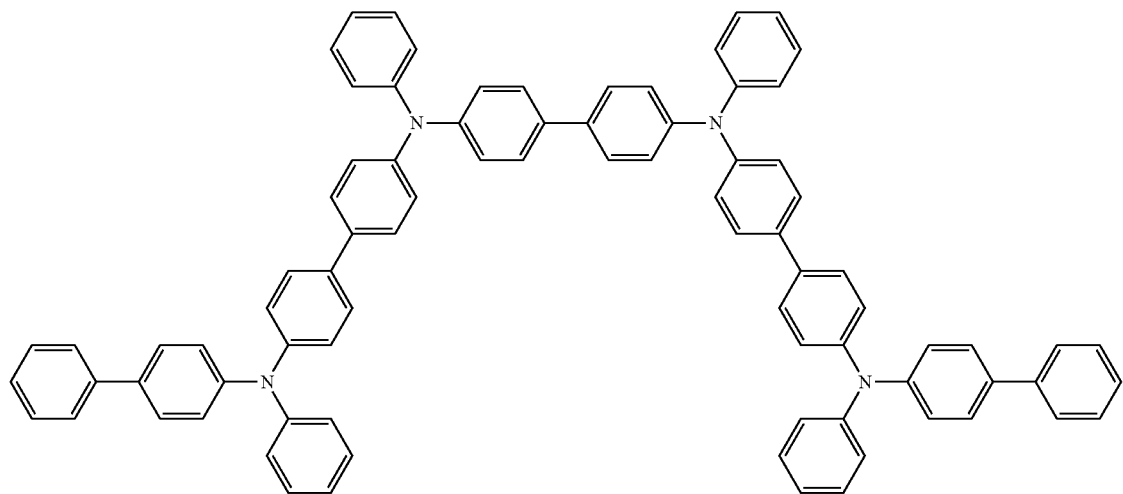
[Chemical Formula 230]
(4-5)
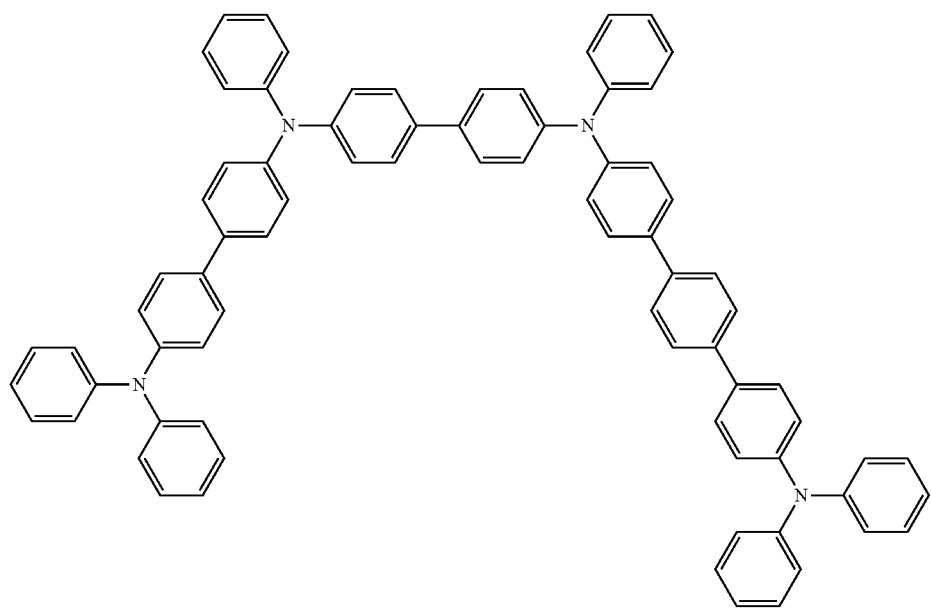

[Chemical Formula 231]
(4-6)
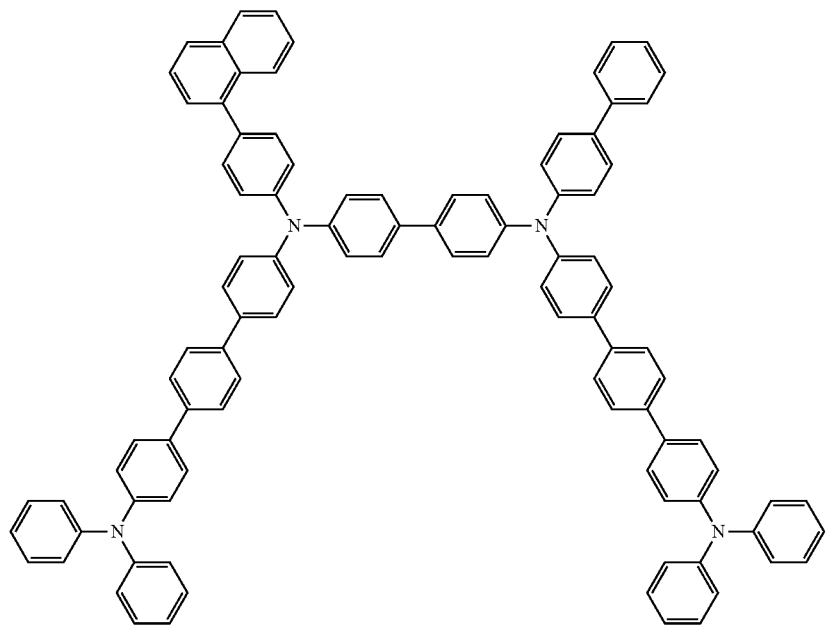
[Chemical Formula 232]
(4-7)
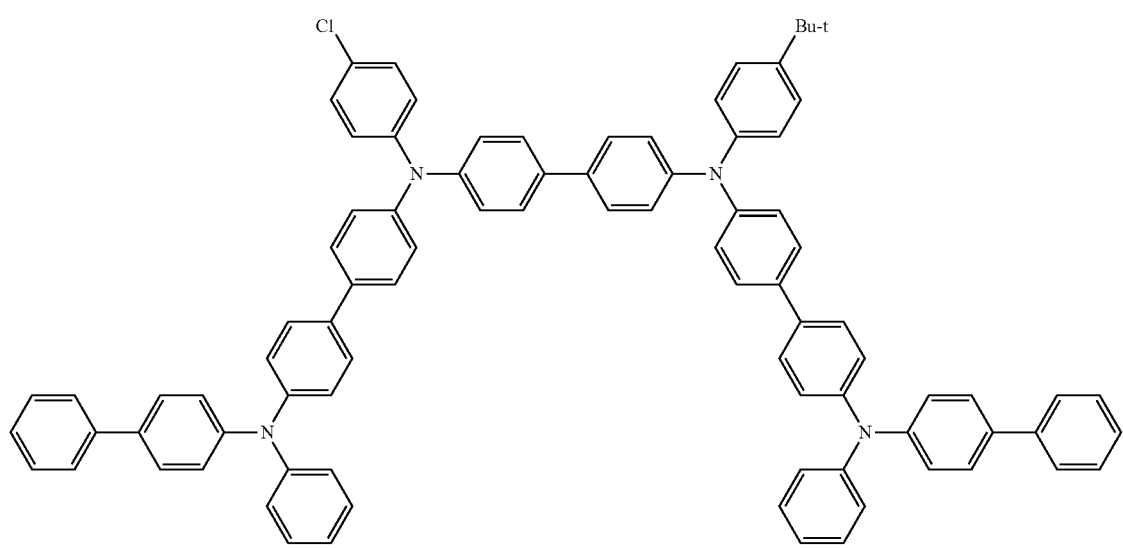

[Chemical Formula 233]
(4-8)
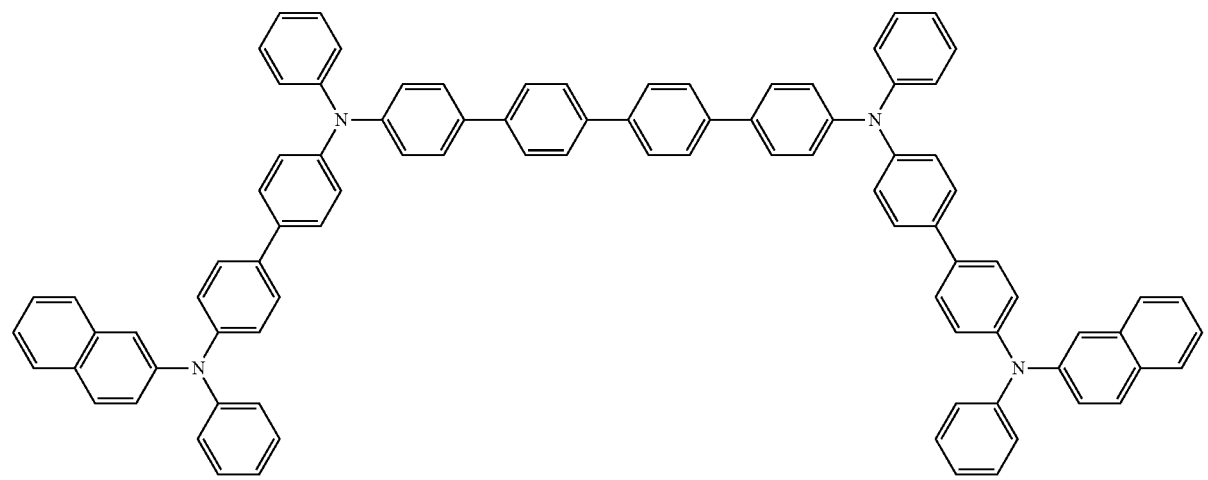
[Chemical Formula 234]
(4-9)
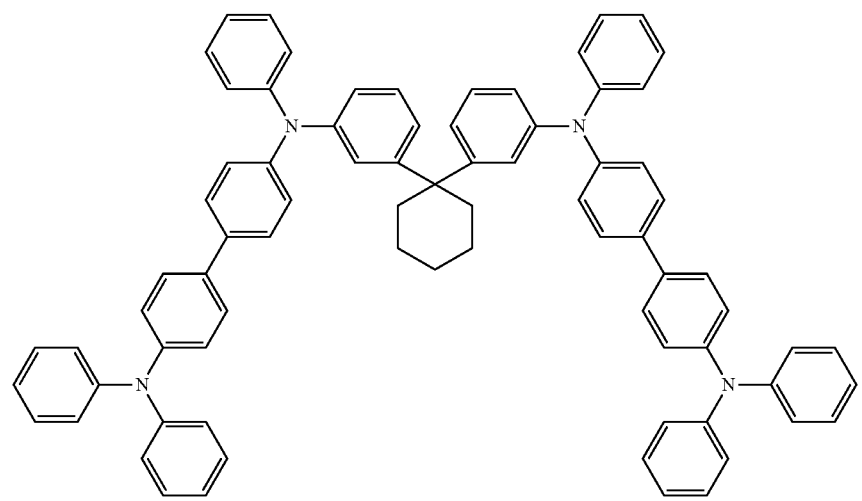
[Chemical Formula 235]
(4-10)
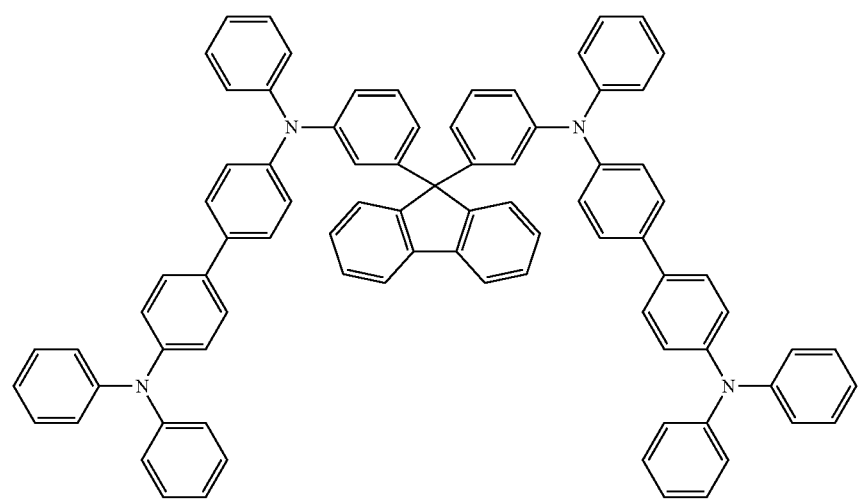

[Chemical Formula 236]
(4-11)
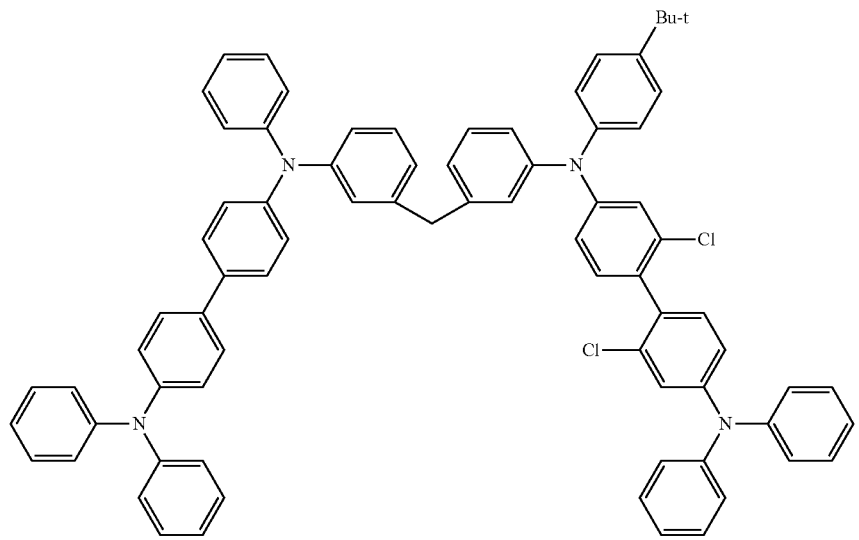
[Chemical Formula 237]
(4-12)
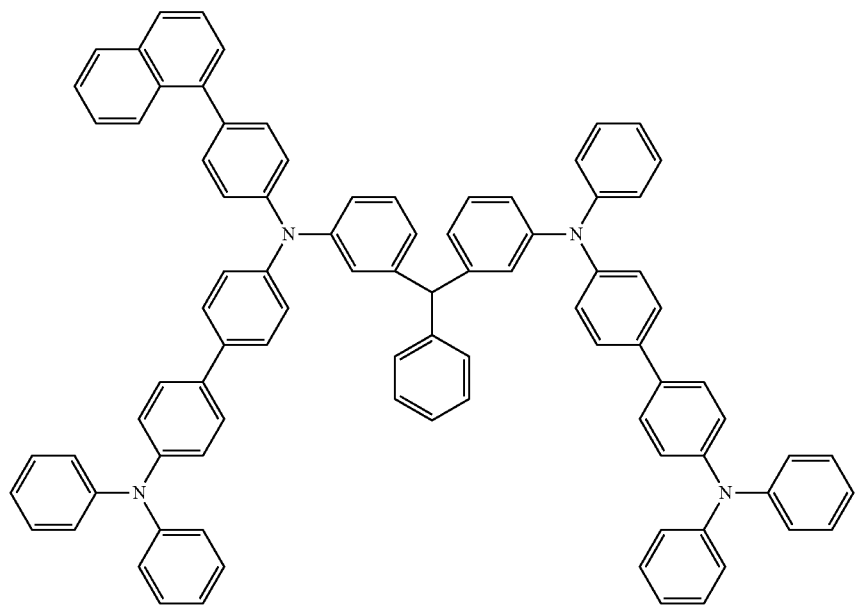

[Chemical Formula 238]
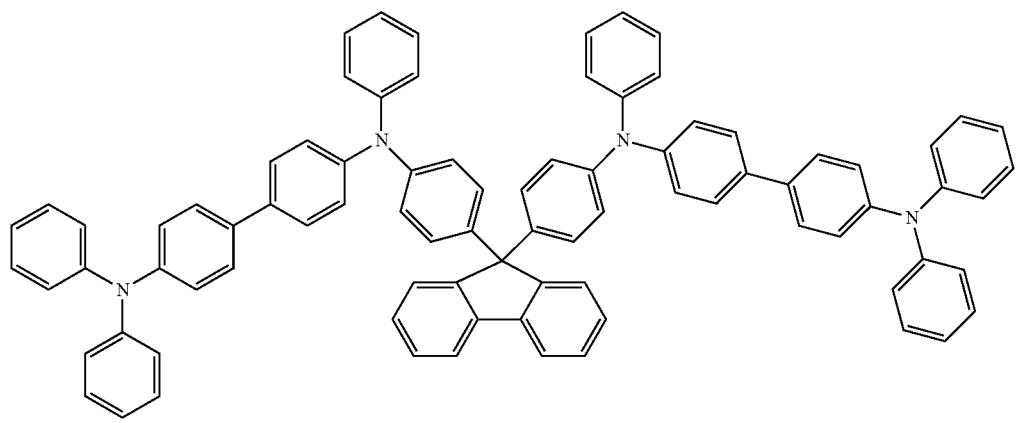
(4-13)
[Chemical Formula 239]
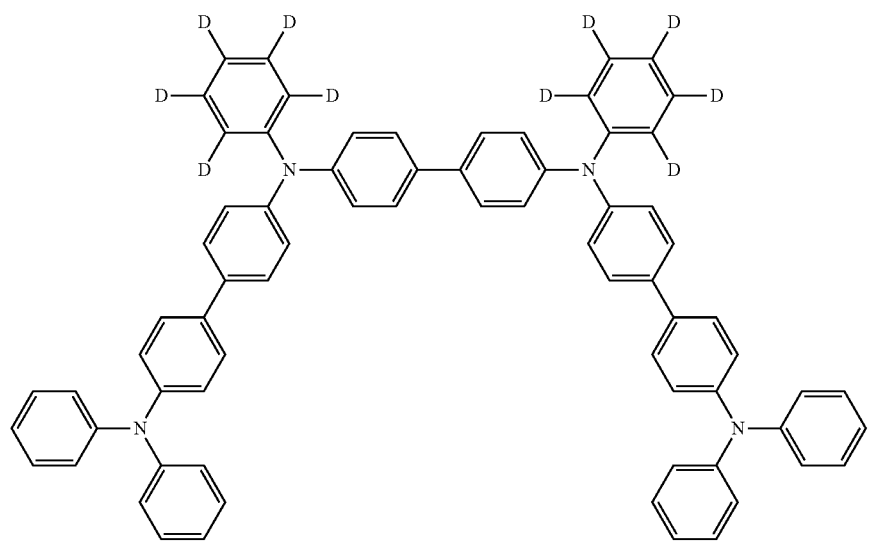
(4-14)

[Chemical Formula 240]
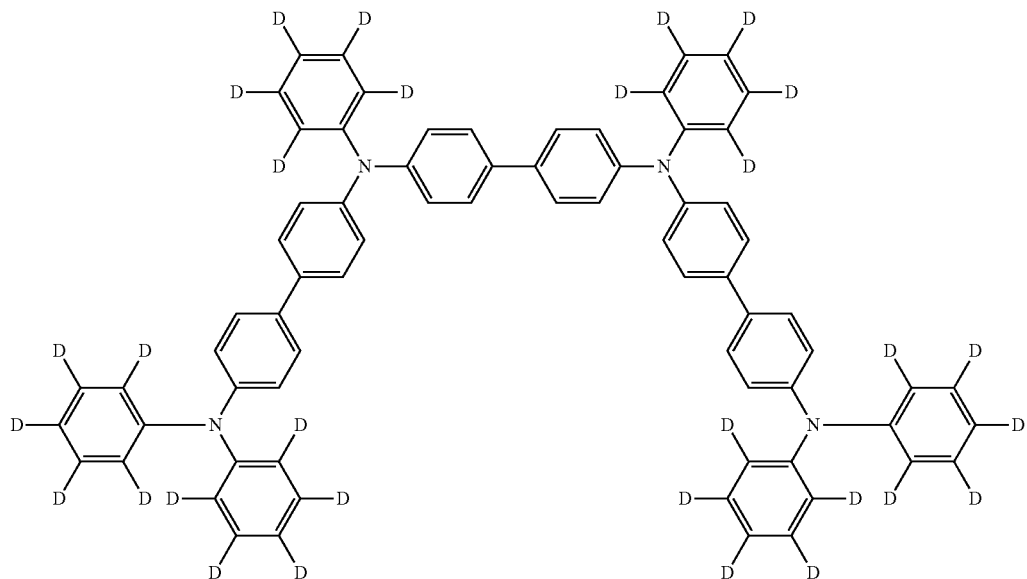
(4-15)
[Chemical Formula 241]
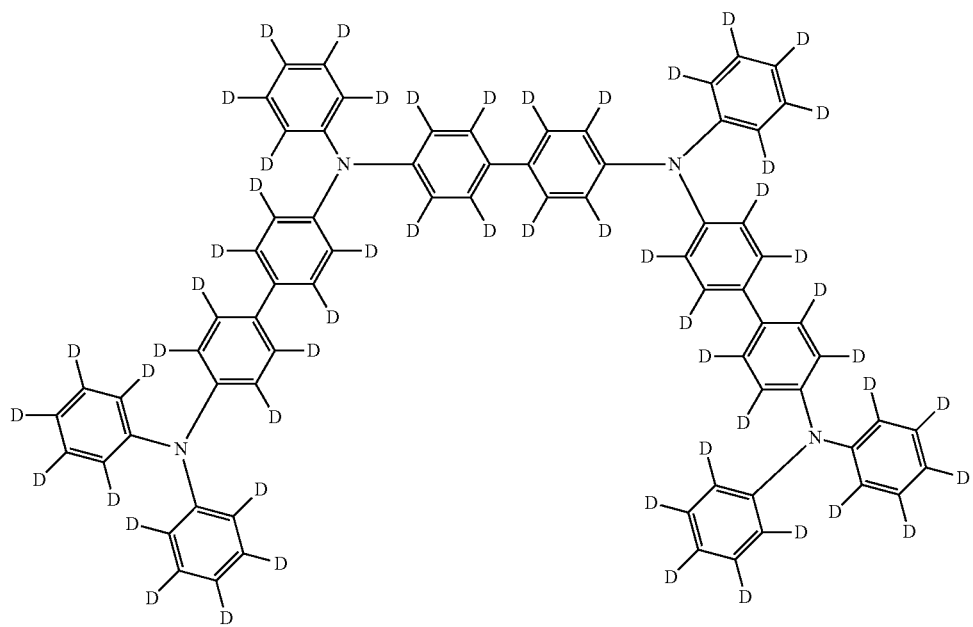
(4-16)

[Chemical Formula 242]

(4-17)

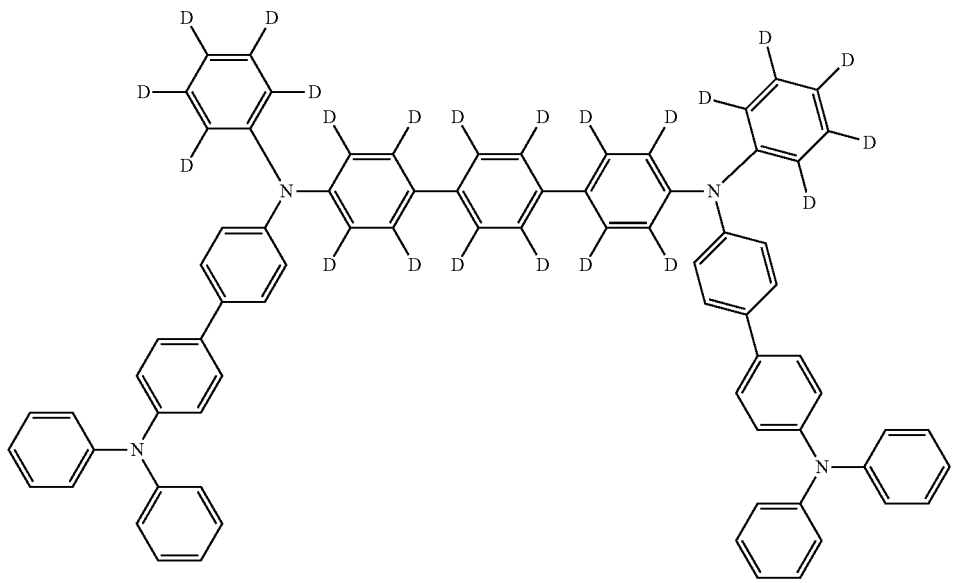

The triphenylamine derivatives of the general formula (3) having two triphenylamine skeletons as a whole molecule, and the triphenylamine derivatives of the general formula (4) having four triphenylamine skeletons as a whole molecule can be synthesized by a known method (refer to PTLs 1 and 8 to 9, for example).

The arylamine compounds of the general formula (1) and the general formula (1a) were purified by methods such as column chromatography, adsorption using, for example, a silica gel, activated carbon, or activated clay, recrystallization or crystallization using a solvent, and a sublimation purification method. The compounds were identified by an NMR analysis. A melting point, a glass transition point (Tg), and a work function were measured as material property values. The melting point can be used as an index of vapor deposition, the glass transition point (Tg) as an index of stability in a thin-film state, and the work function as an index of hole transportability and hole blocking performance.

Other compounds used for the organic EL device of the present invention were purified by methods such as column chromatography, adsorption using, for example, a silica gel, activated carbon, or activated clay, recrystallization or crystallization using a solvent, and a sublimation purification method, and finally purified by a sublimation purification method.

The melting point and the glass transition point (Tg) were measured by a high-sensitive differential scanning calorimeter (DSC3100SA produced by Bruker AXS) using powder.

For the measurement of the work function, a 100 nm-thick thin film was fabricated on an ITO substrate, and an ionization potential measuring device (PYS-202 produced by Sumitomo Heavy Industries, Ltd.) was used.

The organic EL device of the present invention may have a structure including an anode, a hole injection layer, a hole transport layer, a light emitting layer, an electron transport layer, and a cathode successively formed on a substrate, optionally with an electron blocking layer between the hole transport layer and the light emitting layer, a hole blocking layer between the light emitting layer and the electron transport layer, and an electron injection layer between the electron transport layer and the cathode. Some of the organic layers in the multilayer structure may be omitted, or may serve more than one function. For example, a single organic layer may serve as the hole injection layer and the hole transport layer, or as the electron injection layer and the electron transport layer, and so on. Further, any of the layers may be configured to laminate two or more organic layers having the same function, and the hole transport layer may have a two-layer laminated structure, the light emitting layer may have a two-layer laminated structure, the electron transport layer may have a two-layer laminated structure, and so on. The organic EL device of the present invention is preferably configured such that the hole transport layer has a two-layer laminated structure of a first hole transport layer and a second hole transport layer.

Electrode materials with high work functions such as ITO and gold are used as the anode of the organic EL device of the present invention. The hole injection layer of the organic EL device of the present invention may be made of, for example, material such as starburst-type triphenylamine derivatives and various triphenylamine tetramers; porphyrin compounds as represented by copper phthalocyanine; accepting heterocyclic compounds such as hexacyano azatriphenylene; and coating-type polymer materials, in addition to the arylamine compounds of the general formula (1). These materials may be formed into a thin film by a vapor deposition method or other known methods such as a spin coating method and an inkjet method.

The arylamine compounds of the general formula (1) are used as the hole transport layer of the organic EL device of the present invention. These may be individually deposited for film forming, may be used as a single layer deposited mixed with other hole transporting materials, or may be formed as a laminate of individually deposited layers, a laminate of mixedly deposited layers, or a laminate of the individually deposited layer and the mixedly deposited layer. These materials may be formed into a thin-film by a vapor deposition method or other known methods such as a spin coating method and an inkjet method.

Examples of a hole transporting material that can be mixed or can be used at the same time with the arylamine compounds of the general formula (1) can be benzidine derivatives such as N,N'-diphenyl-N,N'-di(m-tolyl)benzidine (TPD), N,N'-diphenyl-N,N'-di(α-naphthyl)benzidine (NPD), and N,N,N',N'-tetrabiphenylylbenzidine; 1,1-bis[4-(di-4-tolylamino)phenyl]cyclohexane (TAPC); triphenylamine derivatives of the general formula (3) having two triphenylamine skeletons as a whole molecule; triphenylamine derivatives of the general formula (4) having four triphenylamine skeletons as a whole molecule; and various triphenylamine derivatives having three triphenylamine skeletons as a whole molecule.

The material used for the hole injection layer or the hole transport layer may be obtained by p-doping materials such as trisbromophenylamine hexachloroantimony, and radialene derivatives (refer to WO2014/009310, for example) into a material commonly used for these layers, or may be, for example, polymer compounds each having, as a part of the compound structure, a structure of a benzidine derivative such as TPD.

In the case where the hole transport layer of the organic EL device of the present invention has a two-layer structure, examples of material used for the first hole transport layer on the anode side can be preferably triphenylamine derivatives of the general formula (3) having two triphenylamine skeletons as a whole molecule and triphenylamine derivatives of the general formula (4) having four triphenylamine skeletons as a whole molecule. Other examples of material used for the first hole transport layer on the anode side can be the above hole transporting materials.

Further, examples of material used for the second hole transport layer can be preferably the arylamine compounds of the general formula (1). Other examples of material used for the second hole transport layer can be the above hole transporting materials.

Examples of material used for the electron blocking layer of the organic EL device of the present invention can be compounds having an electron blocking effect, including, for example, carbazole derivatives such as 4,4',4"-tri(N-carbazolyl)triphenylamine (TCTA), 9,9-bis[4-(carbazol-9-yl)phenyl]fluorene, 1,3-bis(carbazol-9-yl)benzene (mCP), and 2,2-bis(4-carbazol-9-ylphenyl)adamantane (Ad-Cz); and compounds having a triphenylsilyl group and a triarylamine structure, as represented by 9-[4-(carbazol-9-yl)phenyl]-9-[4-(triphenylsilyl)phenyl]-9H-fluorene, in addition to the arylamine compounds of the general formula (1). These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the light emitting layer of the organic EL device of the present invention can be various metal complexes, anthracene derivatives, bis(styryl)benzene derivatives, pyrene derivatives, oxazole derivatives, and polyparaphenylene vinylene derivatives, in addition to quinolinol derivative metal complexes such as Alq3. Further, the light emitting layer may be made of a host material and a dopant material. Examples of the host material can be preferably anthracene derivatives. Other examples of the host material can be heterocyclic compounds having indole ring as a part of a condensed ring, heterocyclic compounds having carbazole ring as a part of a condensed ring, carbazole derivatives, thiazole derivatives, benzimidazole derivatives, and polydialkyl fluorene derivatives, in addition to the above light-emitting materials. Examples of the dopant material can be preferably pyrene derivatives. Other examples of the dopant material can be amine derivatives having fluorene ring as a part of a condensed ring, quinacridone, coumarin, rubrene, perylene, pyrene, derivatives thereof, benzopyran derivatives, indenophenanthrene derivatives, rhodamine derivatives, and aminostyryl derivatives. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer.

Further, the light-emitting material may be a phosphorescent material. Phosphorescent materials as metal complexes of metals such as iridium and platinum may be used. Examples of the phosphorescent materials include green phosphorescent materials such as $Ir(ppy)_3$, blue phosphorescent materials such as Flrpic and FIr6, and red phosphorescent materials such as $Btp_2Ir(acac)$. Here, carbazole derivatives such as 4,4'-di(N-carbazolyl)biphenyl (CBP), TCTA, and mCP may be used as the hole injecting and transporting host material. Compounds such as p-bis(triphenylsilyl)benzene (UGH2) and 2,2',2"-(1,3,5-phenylene)-tris(1-phenyl-1H-benzimidazole) (TPBI) may be used as the electron transporting host material. In this way, a high-performance organic EL device can be produced.

In order to avoid concentration quenching, the doping of the host material with the phosphorescent light-emitting material should preferably be made by co-evaporation in a range of 1 to 30 weight percent with respect to the whole light emitting layer.

Further, Examples of the light-emitting material may be delayed fluorescent-emitting material such as a CDCB derivative of PIC-TRZ, CC2TA, PXZ-TRZ, 4CzIPN or the like (refer to NPL 3, for example).

These materials may be formed into a thin-film by using a vapor deposition method or other known methods such as a spin coating method and an inkjet method.

The hole blocking layer of the organic EL device of the present invention may be formed by using hole blocking compounds such as various rare earth complexes, triazole derivatives, triazine derivatives, and oxadiazole derivatives, in addition to the metal complexes of phenanthroline derivatives such as bathocuproin (BCP), and the metal complexes of quinolinol derivatives such as aluminum(III) bis(2-methyl-8-quinolinate)-4-phenylphenolate (hereinafter referred to as BAlq). These materials may also serve as the material of the electron transport layer. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

A material preferably used for the electron transport layer of the organic EL device of the present invention can be the compounds of the general formula (2) having a pyrimidine ring structure. These may be individually deposited for film forming, may be used as a single layer deposited mixed with other electron transporting materials, or may be formed as a laminate of individually deposited layers, a laminate of mixedly deposited layers, or a laminate of the individually deposited layer and the mixedly deposited layer. These materials may be formed into a thin film by a vapor deposition method or other known methods such as a spin coating method and an inkjet method.

Examples of the electron transporting material that can be mixed or can be used at the same time with the compound represented by the general formula (2) having a pyrimidine ring structure can be metal complexes of quinolinol derivatives such as $Alq_3$ and BAlq, various metal complexes, triazole derivatives, triazine derivatives, oxadiazole derivatives, pyridine derivatives, pyrimidine derivatives, benzimidazole derivatives, thiadiazole derivatives, anthracene derivatives, carbodiimide derivatives, quinoxaline derivatives, pyridoindole derivatives, phenanthroline derivatives, and silole derivatives.

Examples of material used for the electron injection layer of the organic EL device of the present invention can be alkali metal salts such as lithium fluoride and cesium fluoride; alkaline earth metal salts such as magnesium fluoride; and metal oxides such as aluminum oxide. However, the electron injection layer may be omitted in the preferred selection of the electron transport layer and the cathode.

The cathode of the organic EL device of the present invention may be made of an electrode material with a low work function such as aluminum, or an alloy of an electrode material with an even lower work function such as a magnesium-silver alloy, a magnesium-indium alloy, or an aluminum-magnesium alloy.

The following describes an embodiment of the present invention in more detail based on Examples. The present invention, however, is not restricted to the following Examples.

Example 1

Synthesis of 4,4"-bis{(biphenyl-4-yl)-phenylamino}-3-phenyl-1,1':3',1"-terphenyl (Compound 1-12)

4-{(biphenyl-4-yl)-phenylamino}-4"-{(biphenyl-4-yl)-amino}-3-phenyl-1,1':3',1"-terphenyl (17.0 g), bromobenzene (4.12 g), palladium acetate (0.13 g), a toluene solution (0.33 mL) containing 50% (w/v) tri-tert-butylphosphine, sodium tert-butoxide (2.73 g), and toluene (190 mL) were added into a nitrogen-substituted reaction vessel. The mixture was heated and stirred at 80° C. for 3 hours. After cooling, the insoluble matter was removed by filtration, and the filtrate was concentrated. The crude product was purified by column chromatography (support: silica gel, eluent: toluene/n-hexane), a solid precipitated by adding acetone was collected, whereby a white powder of 4,4"-bis{(biphenyl-4-yl)-phenylamino}-3-phenyl-1,1':3',1"-terphenyl (Compound 1-12; 13.29 g; yield: 71%) was obtained.

The structure of the obtained white powder was identified by NMR.

$^1$H-NMR (CDCl$_3$) detected 44 hydrogen signals, as follows.

δ (ppm)=7.62-7.58 (4H), 7.55-7.49 (4H), 7.48-7.38 (6H), 7.37-7.05 (30H).

[Chemical Formula 243]

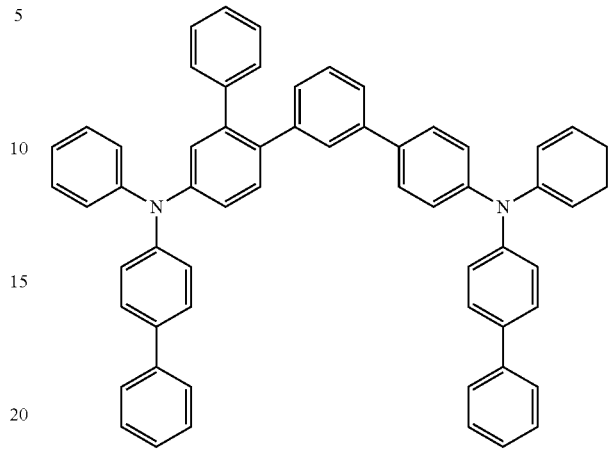

(1-12)

Example 2

Synthesis of 4,4"-bis{(biphenyl-4-yl)-phenylamino}-3,3"-diphenyl-1,1':4',1"-terphenyl (Compound 1-9)

4,4"-bis{(biphenyl-4-yl)-amino}-3,3"-diphenyl-1,1':4', 1"-terphenyl (16.3 g), iodobenzene (18.6 g), copper powder (0.29 g), potassium carbonate (9.61 g), 3,5-di-tert-butylsalicylicacid (1.85 g), sodium hydrogensulfite (0.47 g), dodecylbenzene (20 mL) were added into a nitrogen-substituted reaction vessel. The mixture was heated and stirred at 190 to 200° C. for 17 hours. The mixture was cooled, toluene (1500 mL), a silica gel (40 g), and activated clay (20 g) was added thereto, and stirred. After the insoluble matter was removed by filtration, the filtrate was concentrated. The crude product was purified by recrystallization with chlorobenzene, the recrystallization procedure was repeated to obtain a white powder of 4,4"-bis{(biphenyl-4-yl)-phenylamino}-3,3"-diphenyl-1,1':4',1"-terphenyl (Compound 1-9; 9.65 g; yield 49%).

The structure of the obtained white powder was identified by NMR.

$^1$H-NMR (CDCl$_3$) detected 48 hydrogen signals, as follows.

δ (ppm)=7.62 (4H), 7.52 (4H), 7.45 (4H), 7.36-7.04 (32H), 6.99 (4H).

[Chemical Formula 244]

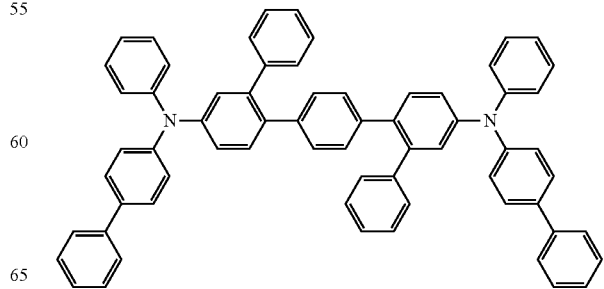

(1-9)

Example 3

Synthesis of 4-bis(biphenyl-4-yl)amino-4'-{(biphenyl-4-yl)-phenylamino}-2,6-diphenyl-biphenyl (Compound 1-23)

4-bis(biphenyl-4-yl)amino-2,6-diphenyl-bromobenzene (16.0 g), 4-{N-(biphenyl-4-yl)-N-phenylamino} phenylboronicacid (10.2 g), tetrakistriphenylphosphine palladium (0.60 g), potassium carbonate (4.62 g), water (60 mL), toluene (320 mL), and ethanol (60 mL) were added into a nitrogen-substituted reaction vessel. The mixture was heated, and stirred for 18 hours under reflux. After cooling, water (200 mL) was added thereto, and then an organic layer was collected by liquid separation. The organic layer was dried over anhydrous magnesium sulfate and purified by adsorption with a silica gel (40 g). The organic layer was then concentrated and dispersed and washed using methanol to obtain a crude product.

The crude product was purified by recrystallization with a toluene/ethanol mixed solvent, and then with ethyl acetate. The recrystallization procedure was repeated to obtain a white powder of 4-bis(biphenyl-4-yl)amino-4'-{(biphenyl-4-yl)-phenylamino}-2,6-diphenyl-biphenyl (Compound 1-23; 12.7 g; yield 57%).

The structure of the obtained white powder was identified by NMR.

$^1$H-NMR (CDCl$_3$) detected 48 hydrogen signals, as follows.

δ (ppm)=7.65-7.53 (8H), 7.48-6.97 (36H), 6.79-6.73 (4H).

[Chemical Formula 245]

(1-23)

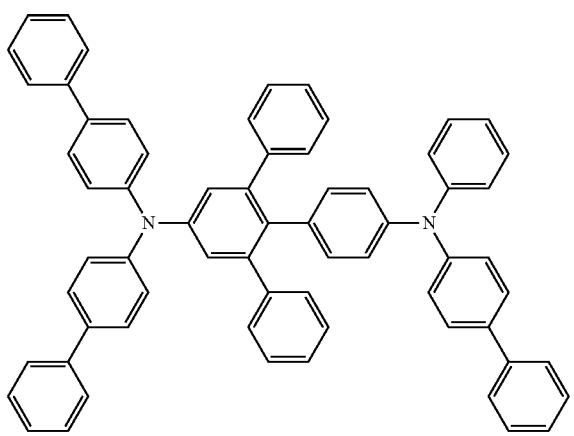

Example 4

Synthesis of 4,4"-bis{(biphenyl-4-yl)-phenylamino}-2-phenyl-1,1':4',1"-terphenyl (Compound 1-1)

(6-bromo-1,1'-biphenyl-3-yl)-(1,1'-biphenyl-4-yl)phenylamine (18.0 g), 4-{N-(biphenyl-4-yl)-N-phenylamino} phenylboronicacid (10.2 g), (1,1'-biphenyl-4-yl)phenylamino(1,1'-biphenyl-4'-yl)boronic acid pinacolato ester (21.8 g), tetrakistriphenylphosphine palladium (0.87 g), potassium carbonate (6.3 g), water (46 mL), toluene (144 mL), and ethanol (36 mL) were added into a nitrogen-substituted reaction vessel. The mixture was heated, and stirred for 18 hours under reflux. After cooling, water (100 mL) was added thereto, and then an organic layer was collected by liquid separation. The organic layer was dried over anhydrous magnesium sulfate, and then concentrated. The residue was purified by column chromatography to obtain a white powder of 4,4"-bis{(biphenyl-4-yl)-phenylamino}-2-phenyl-1,1':4',1"-terphenyl (Compound 1-1; 12.9 g; yield 43%).

The structure of the obtained white powder was identified by NMR.

$^1$H-NMR (CDCl$_3$) detected 44 hydrogen signals, as follows.

δ (ppm)=7.65-7.61 (4H), 7.57-7.07 (40H).

[Chemical Formula 246]

(1-1)

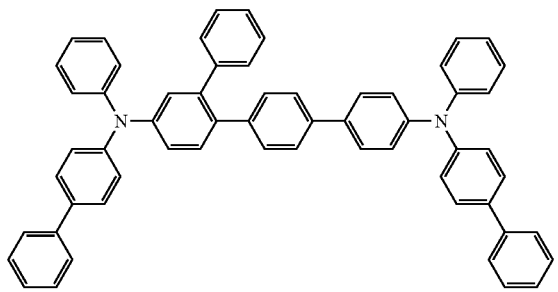

Example 5

Synthesis of 4-bis(biphenyl-4-yl)amino-4'-{(biphenyl-4-yl)-phenylamino}-2-phenyl-1,1'-biphenyl (Compound 1-24)

(6-bromo-1,1'-biphenyl-3-yl)-bis(biphenyl-4-yl)amine (10.0 g), 4-{N-(biphenyl-4-yl)-N-phenylamino} phenylboronicacid (7.9 g), tetrakistriphenylphosphine palladium (0.60 g), potassium carbonate (5.0 g), water (30 mL), toluene (80 mL), and ethanol (40 mL) were added into a nitrogen-substituted reaction vessel. The mixture was heated, and stirred for 16 hours under reflux. After cooling, water (100 mL) was added thereto, and then an organic layer was collected by liquid separation. The organic layer was dried over anhydrous magnesium sulfate, and then concentrated. The residue was purified by column chromatography to obtain a white powder of 4-bis(biphenyl-4-yl)amino-4'-{(biphenyl-4-yl)-phenylamino}-2-phenyl-1,1'-biphenyl (Compound 1-24; 5.3 g; yield 37%).

The structure of the obtained white powder was identified by NMR.

$^1$H-NMR (CDCl$_3$) detected 44 hydrogen signals, as follows.

δ (ppm)=7.65-7.56 (8H), 7.52-7.14 (28H), 7.08-6.99 (8H).

[Chemical Formula 247]

(1-24)

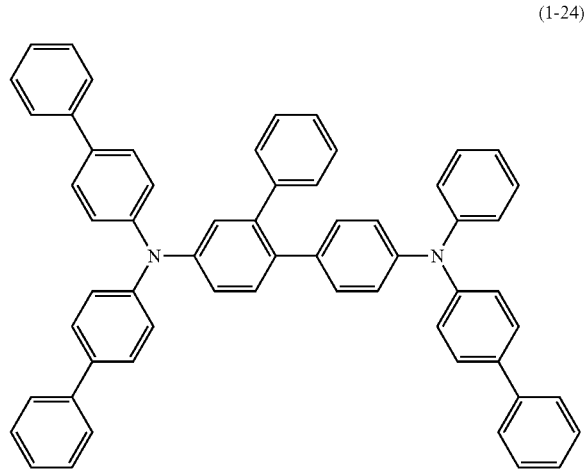

[Chemical Formula 248]

(1-26)

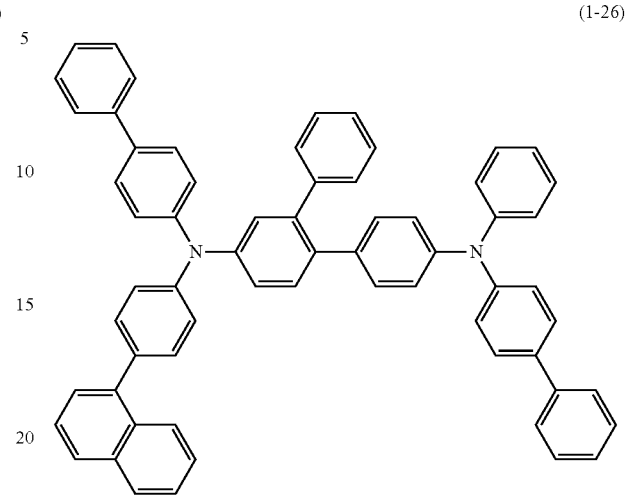

Example 6

Synthesis of 4-{(naphthalene-1-yl)phenyl-4-yl}(biphenyl-4-yl)amino-4'-{(biphenyl-4-yl)-phenylamino}-2-phenyl-1,1'-biphenyl (Compound 1-26)

(6-bromo-1,1'-biphenyl-3-yl)-{(naphthalene-1-yl)phenyl-4-yl}(biphenyl-4-yl)amine (10.0 g), 4-{N-(biphenyl-4-yl)-N-phenylamino} phenylboronicacid (7.3 g), tetrakistriphenylphosphine palladium (0.60 g), potassium carbonate (4.6 g), water (30 mL), toluene (80 mL), and ethanol (40 mL) were added into a nitrogen-substituted reaction vessel. The mixture was heated, and stirred for 16 hours under reflux. After cooling, water (100 mL) was added thereto, and then an organic layer was collected by liquid separation. The organic layer was dried over anhydrous magnesium sulfate, and then concentrated. The residue was purified by column chromatography to obtain a white powder of 4-{(naphthalene-1-yl)phenyl-4-yl}(biphenyl-4-yl)amino-4'-{(biphenyl-4-yl)-phenylamino}-2-phenyl-1,1'-biphenyl (Compound 1-26; 9.7 g; yield 69%).

The structure of the obtained white powder was identified by NMR.

$^1$H-NMR (CDCl$_3$) detected 46 hydrogen signals, as follows.

δ (ppm)=8.08-8.07 (1H), 7.95-7.87 (2H), 7.66-6.99 (43H).

Example 7

Synthesis of 4-{(naphthalene-2-yl)phenyl-4-yl}(biphenyl-4-yl)amino-4'-{(biphenyl-4-yl)-phenylamino}-2-phenyl-1,1'-biphenyl (Compound 1-27)

(6-bromo-1,1'-biphenyl-3-yl)-{(naphthalene-2-yl)phenyl-4-yl}(biphenyl-4-yl)amine (7.5 g), 4-{N-(biphenyl-4-yl)-N-phenylamino}phenylboronicacid (5.5 g), tetrakistriphenylphosphine palladium (0.40 g), potassium carbonate (3.4 g), water (23 mL), toluene (60 mL), and ethanol (30 mL) were added into a nitrogen-substituted reaction vessel. The mixture was heated, and stirred for 16 hours under reflux. After cooling, water (100 mL) was added thereto, and then an organic layer was collected by liquid separation. The organic layer was dried over anhydrous magnesium sulfate, and then concentrated. The residue was purified by column chromatography to obtain a white powder of 4-{(naphthalene-2-yl)phenyl-4-yl}(biphenyl-4-yl)amino-4'-{(biphenyl-4-yl)-phenylamino}-2-phenyl-1,1'-biphenyl (Compound 1-27; 6.1 g; yield 58%).

The structure of the obtained white powder was identified by NMR.

$^1$H-NMR (CDCl$_3$) detected 46 hydrogen signals, as follows.

δ (ppm)=8.07 (1H), 7.95-7.76 (4H), 7.68-6.98 (41H).

[Chemical Formula 249]

(1-27)

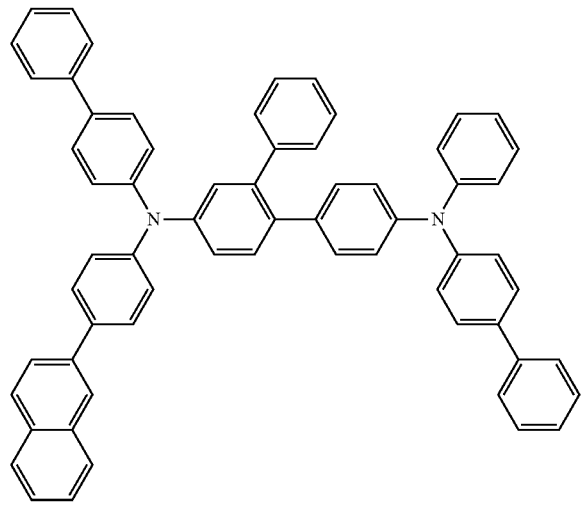

[Chemical Formula 250]

(1-29)

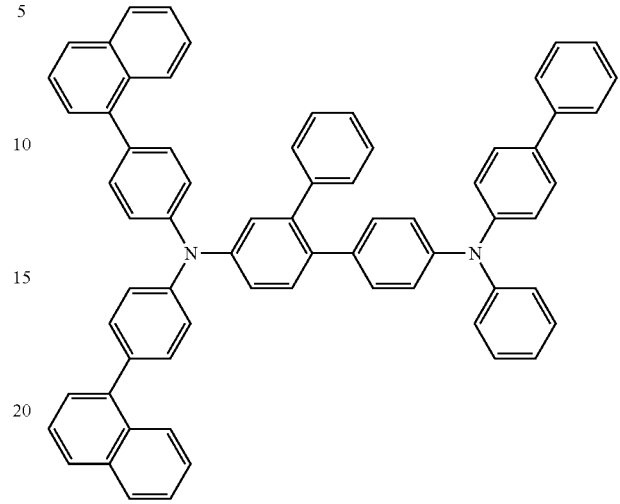

Example 8

Synthesis of 4-bis{(naphthalene-1-yl)phenyl-4-yl}amino-4'-{(biphenyl-4-yl)-phenylamino}-2-phenyl-biphenyl (Compound 1-29)

(6-bromo-1,1'-biphenyl-3-yl)-bis{(naphthalene-1-yl)phenyl-4-yl}amine (10.0 g), 4-{N-(biphenyl-4-yl)-N-phenylamino}phenylboronicacid (6.7 g), tetrakistriphenylphosphine palladium (0.50 g), potassium carbonate (4.2 g), water (30 mL), toluene (80 mL), and ethanol (40 mL) were added into a nitrogen-substituted reaction vessel. The mixture was heated, and stirred for 16 hours under reflux. After cooling, water (100 mL) was added thereto, and then an organic layer was collected by liquid separation. The organic layer was dried over anhydrous magnesium sulfate, and then concentrated. The residue was purified by column chromatography to obtain a white powder of 4-bis{(naphthalene-1-yl)phenyl-4-yl}amino-4'-{(biphenyl-4-yl)-phenylamino}-2-phenyl-biphenyl (Compound 1-29; 10 g; yield 73%).

The structure of the obtained white powder was identified by NMR.

$^1$H-NMR (CDCl$_3$) detected 48 hydrogen signals, as follows.

δ (ppm)=8.12-8.10 (2H), 7.97-7.88 (4H), 7.63-7.01 (42H).

Example 9

Synthesis of 4-{(9,9-dimethylfluorene-2-yl)phenyl-4-yl}(biphenyl-4-yl)amino-4'-{(biphenyl-4-yl)-phenylamino}-3-phenyl-1,1'-biphenyl (Compound 1-30)

(6-bromo-1,1'-biphenyl-3-yl)-{(9,9-dimethylfluorene-2-yl)phenyl-4-yl}(biphenyl-4-yl)amine (12.1 g), 4-{N-(biphenyl-4-yl)-N-phenylamino}phenylboronicacid (8.9 g), tetrakistriphenylphosphine palladium (0.70 g), potassium carbonate (5.6 g), water (40 mL), toluene (100 mL), and ethanol (50 mL) were added into a nitrogen-substituted reaction vessel. The mixture was heated, and stirred for 16 hours under reflux. After cooling, water (100 mL) was added thereto, and then an organic layer was collected by liquid separation. The organic layer was dried over anhydrous magnesium sulfate, and then concentrated. The residue was purified by column chromatography to obtain a white powder of 4-{(9,9-dimethylfluorene-2-yl)phenyl-4-yl}(biphenyl-4-yl)amino-4'-{(biphenyl-4-yl)-phenylamino}-3-phenyl-1,1'-biphenyl (Compound 1-30; 8.3 g; yield 49%).

The structure of the obtained white powder was identified by NMR.

$^1$H-NMR (CDCl$_3$) detected 48 hydrogen signals, as follows.

δ (ppm)=7.71-7.15 (34H), 7.09-6.99 (8H), 1.51 (6H).

[Chemical Formula 251]

(1-30)

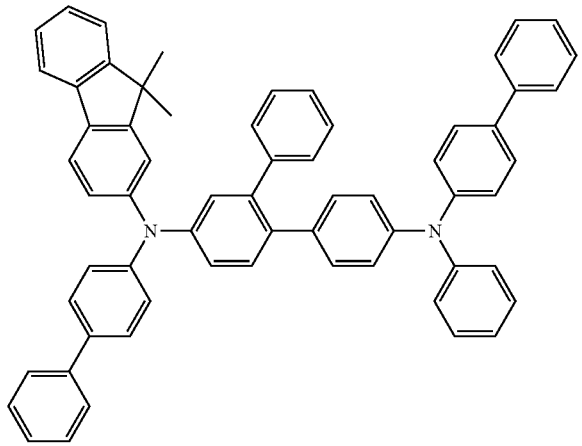

Example 10

The melting points and the glass transition points of the arylamine compounds of the general formula (1) were measured using a high-sensitive differential scanning calorimeter (DSC3100SA produced by Bruker AXS).

|  | Melting point | Glass transition point |
|---|---|---|
| Compound of Example 1 | No melting point observed | 116° C. |
| Compound of Example 2 | 263° C. | 124° C. |
| Compound of Example 3 | 238° C. | 126° C. |
| Compound of Example 4 | No melting point observed | 120° C. |
| Compound of Example 5 | No melting point observed | 118° C. |
| Compound of Example 6 | No melting point observed | 121° C. |
| Compound of Example 7 | No melting point observed | 121° C. |
| Compound of Example 8 | No melting point observed | 125° C. |
| Compound of Example 9 | No melting point observed | 125° C. |

The arylamine compounds of the general formula (1) have glass transition points of 100° C. or higher, demonstrating that the compounds have a stable thin-film state.

Example 11

A 100 nm-thick vapor-deposited film was fabricated on an ITO substrate using the arylamine compounds of the general formula (1), and a work function was measured using an ionization potential measuring device (PYS-202 produced by Sumitomo Heavy Industries, Ltd.).

|  | Work function |
|---|---|
| Compound of Example 1 | 5.79 eV |
| Compound of Example 2 | 5.74 eV |
| Compound of Example 3 | 5.67 eV |
| Compound of Example 4 | 5.70 eV |
| Compound of Example 5 | 5.62 eV |
| Compound of Example 6 | 5.60 eV |
| Compound of Example 7 | 5.65 eV |
| Compound of Example 8 | 5.63 eV |
| Compound of Example 9 | 5.57 eV |

As the results show, the arylamine compounds of the general formula (1) have desirable energy levels compared to the work function 5.4 eV of common hole transport materials such as NPD and TPD, and thus possess desirable hole transportability.

Example 12

The organic EL device, as shown in FIG. 1, was fabricated by vapor-depositing a hole injection layer 3, a first hole transport layer 4, a second hole transport layer 5, a light emitting layer 6, an electron transport layer 7, an electron injection layer 8, and a cathode (aluminum electrode) 9 in this order on a glass substrate 1 on which an ITO electrode was formed as a transparent anode 2 beforehand.

Specifically, the glass substrate 1 having ITO having a film thickness of 150 nm formed thereon was subjected to ultrasonic washing in isopropyl alcohol for 20 minutes and then dried for 10 minutes on a hot plate heated to 200° C. Thereafter, after performing a UV ozone treatment for 15 minutes, the glass substrate with ITO was installed in a vacuum vapor deposition apparatus, and the pressure was reduced to 0.001 Pa or lower. Subsequently, as the hole injection layer 3 covering the transparent anode 2, Compound (HIM-1) of the structural formula below were formed in a film thickness of 5 nm. As the first hole transport layer 4 on the hole injection layer 3, the triphenylamine derivative (3-1) having two triphenylamine skeletons as a whole molecule was formed in a film thickness of 60 nm. As the second hole transport layer 5 on the first hole transport layer 4, Compound (1-12) of Example 1 was formed in a film thickness of 5 nm. As the light emitting layer 6 on the second hole transport layer 5, the pyrene derivative (EMD-1) of the structural formula below and the anthracene derivative (EMH-1) were formed in a film thickness of 20 nm by dual vapor deposition at a vapor deposition rate that satisfies a vapor deposition rate ratio of EMD-1/EMH-1=5/95. As the electron transport layer 7 on the light emitting layer 6, Compound (2-125) having the pyrimidine ring structure of the structural formula below and Compound (ETM-1) of the structural formula below were formed in a film thickness of 30 nm by dual vapor deposition at a vapor deposition rate that satisfies a vapor deposition rate ratio of Compound (2-125)/ETM-1=50/50. As the electron injection layer 8 on the electron transport layer 7, lithium fluoride was formed in a film thickness of 1 nm. Finally, aluminum was vapor-deposited in a thickness of 100 nm to form the cathode 9. The characteristics of the organic EL device were measured in the atmosphere at ordinary temperature. Table 1 summarizes the results of measurement of emission characteristics when applying a DC voltage to the fabricated organic EL device.

[Chemical Formula 252]
(HIM-1)
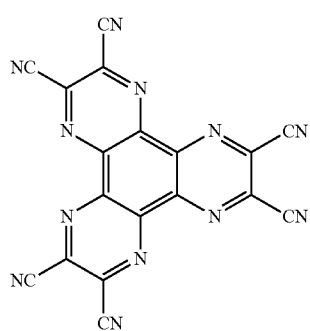
[Chemical Formula 253]
(3-1)
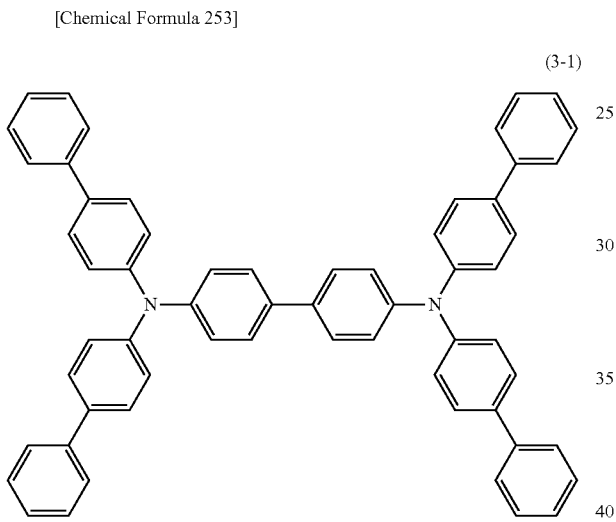
[Chemical Formula 254]
(1-12)
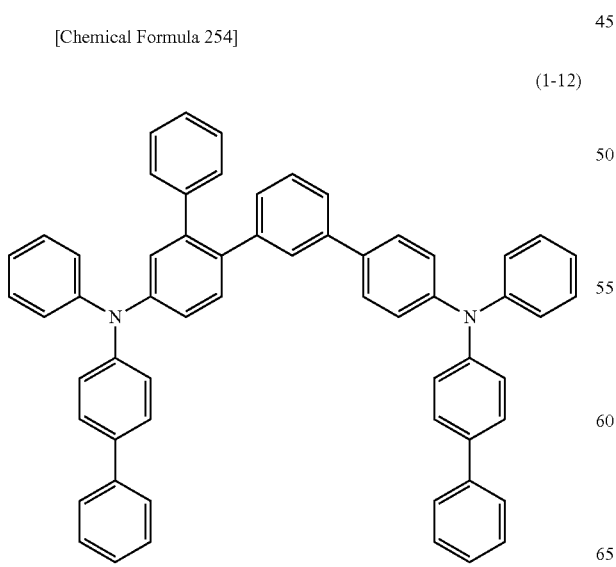
-continued
[Chemical Formula 255]
(EMD-1)
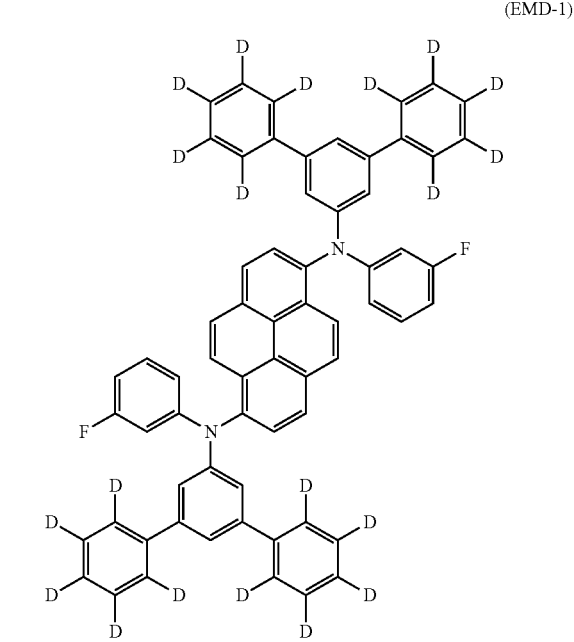
[Chemical Formula 256]
(EMH-1)
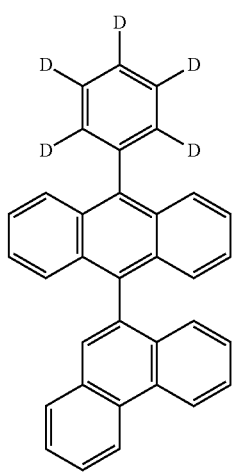

-continued

[Chemical Formula 257]

(2-125)

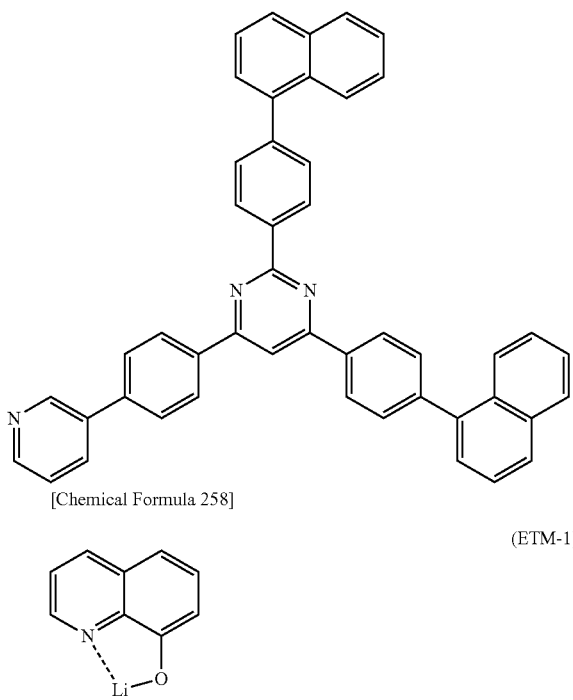

[Chemical Formula 258]

(ETM-1)

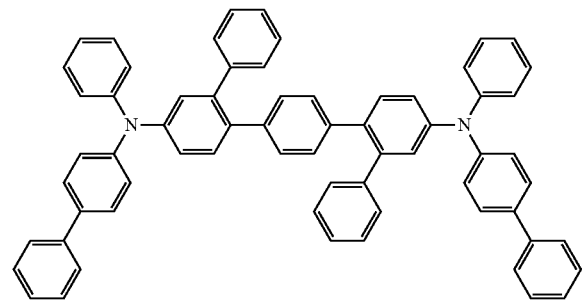

Example 13

An organic EL device was fabricated under the same conditions used in Example 12, except that the second hole transport layer 5 was formed by forming the compound (1-9) of Example 2 in a film thickness of 5 nm, instead of using the compound (1-12) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 259]

(1-9)

Example 14

An organic EL device was fabricated under the same conditions used in Example 10, except that the second hole transport layer 5 was formed by forming the compound (1-1) of Example 4 in a film thickness of 5 nm, instead of using the compound (1-12) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 260]

(1-1)

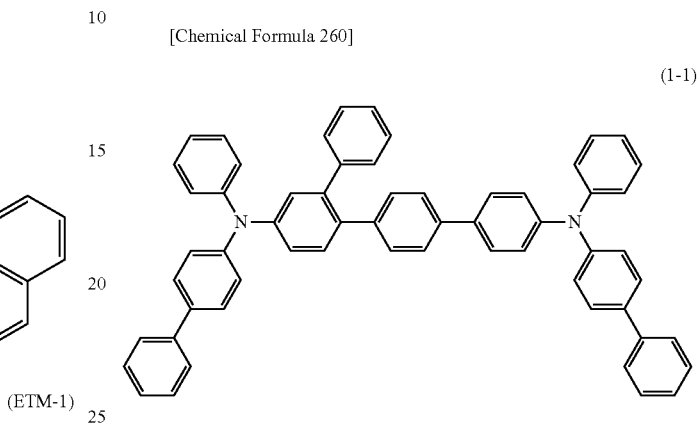

Example 15

An organic EL device was fabricated under the same conditions used in Example 12, except that the second hole transport layer 5 was formed by forming the compound (1-26) of Example 6 in a film thickness of 5 nm, instead of using the compound (1-12) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 261]

(1-26)

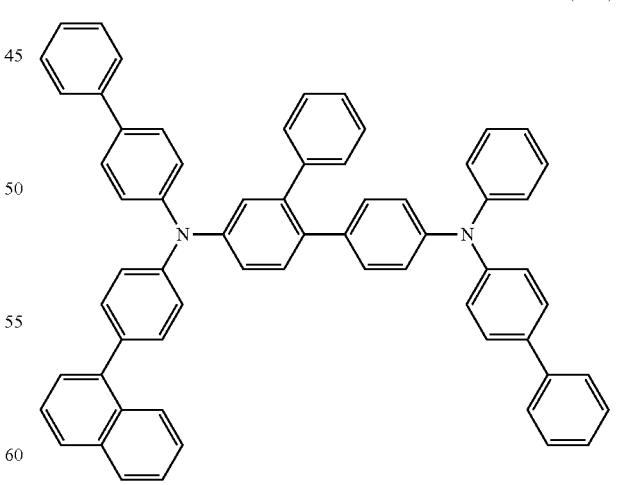

Example 16

An organic EL device was fabricated under the same conditions used in Example 12, except that the second hole transport layer 5 was formed by forming the compound (1-27) of Example 7 in a film thickness of 5 nm, instead of using the compound (1-12) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 262]

(1-27)

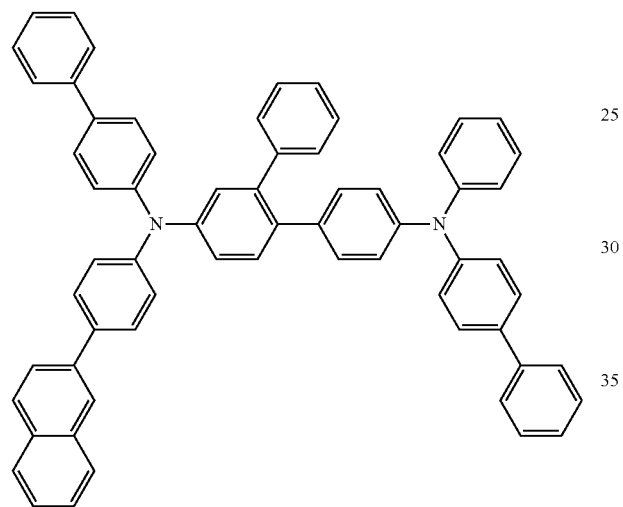

[Chemical Formula 263]

(1-29)

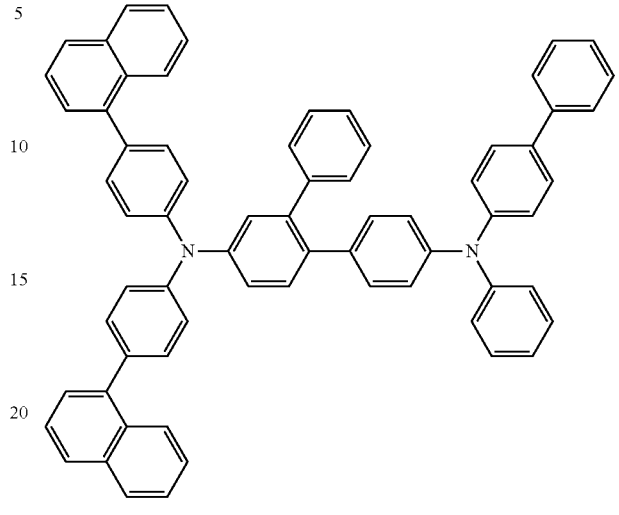

Example 17

An organic EL device was fabricated under the same conditions used in Example 12, except that the second hole transport layer 5 was formed by forming the compound (1-29) of Example 8 in a film thickness of 5 nm, instead of using the compound (1-12) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

Comparative Example 1

For comparison, an organic EL device was fabricated under the same conditions used in Example 12, except that the second hole transport layer 5 was formed by forming the triphenylamine derivative (3-1) of the structural formula having two triphenylamine skeletons as a whole molecule in a film thickness of 5 nm, instead of using the compound (1-12) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

Comparative Example 2

For comparison, an organic EL device was fabricated under the same conditions used in Example 12, except that the second hole transport layer 5 was formed by forming the arylamine compound (HTM-1) of the structural formula below in which the 3-position was unsubstituted with a phenyl group in the compound (1-12) of Example 1 in a film thickness of 5 nm, instead of using the compound (1-12) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 264]

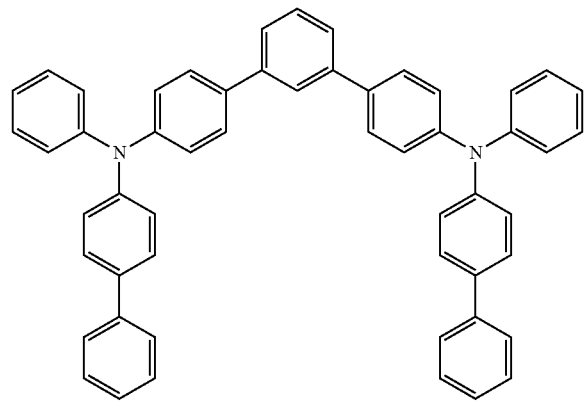

(HTM-1)

Table 1 summarizes the results of measurement of a device lifetime using the organic EL devices fabricated in Examples 12 to 17 and Comparative Examples 1 to 2. The device lifetime was measured as a time elapsed until the emission luminance of 2,000 cd/m² (initial luminance) at the start of emission was attenuated to 1,900 cd/m² (corresponding to 95% when taking the initial luminance as 100%: Attenuation to 95%) when carrying out constant current driving.

TABLE 1

| | First hole transport layer | Second hole transport layer | Electron transport layer | Voltage [V] (@10 mA/cm²) | Luminance [cd/m²] (@10 mA/cm²) | Luminous efficiency [cd/A] (@10 mA/cm²) | Power efficiency [lm/W] (@10 mA/cm²) | Lifetime of device, attenulation to 95% |
|---|---|---|---|---|---|---|---|---|
| Example 12 | 3-1 | 1-12 | 2-125/ETM-1 | 3.81 | 905 | 9.05 | 7.54 | 213 hours |
| Example 13 | 3-1 | 1-9 | 2-125/ETM-1 | 3.78 | 891 | 8.92 | 7.49 | 198 hours |
| Example 14 | 3-1 | 1-1 | 2-125/ETM-1 | 3.85 | 880 | 8.82 | 7.21 | 228 hours |
| Example 15 | 3-1 | 1-26 | 2-125/ETM-1 | 3.80 | 865 | 8.65 | 7.21 | 208 hours |
| Example 16 | 3-1 | 1-27 | 2-125/ETM-1 | 3.76 | 862 | 8.64 | 7.29 | 211 hours |
| Example 17 | 3-1 | 1-29 | 2-125/ETM-1 | 3.75 | 875 | 8.77 | 7.41 | 171 hours |
| Comparative Example 1 | 3-1 | 3-1 | 2-125/ETM-1 | 3.76 | 781 | 7.82 | 6.54 | 162 hours |
| Comparative Example 2 | 3-1 | HTM-1 | 2-125/ETM-1 | 3.83 | 868 | 8.69 | 7.13 | 136 hours |

As shown in Table 1, the luminous efficiency upon passing a current with a current density of 10 mA/cm² was 8.64 to 9.05 cd/A for the organic EL devices in Examples 12 to 17, which was higher than 7.82 to 8.69 cd/A for the organic EL devices in Comparative Examples 1 to 2. Further, the power efficiency was 7.21 to 7.54 lm/W for the organic EL devices in Examples 12 to 17, which was higher than 6.54 to 7.13 lm/W for the organic EL devices in Comparative Examples 1 to 2.

Table 1 also shows that the device lifetime (attenuation to 95%) was 171 to 228 hours for the organic EL devices in Examples 12 to 17, showing achievement of a far longer lifetime than 136 to 162 hours for the organic EL devices in Comparative Examples 1 to 2.

It was found that the organic EL device of the present invention can achieve an organic EL device having high luminous efficiency and a long lifetime compared to the conventional organic EL devices by combining the arylamine compounds in which a specific position was substituted with an aryl group in the hole transport layer so that carrier balance inside the organic EL device is improved.

INDUSTRIAL APPLICABILITY

The organic EL device of the present invention in which the hole transport layer combined the arylamine compounds in which a specific position was substituted with an aryl group improves the luminous efficiency, and also the durability of the organic EL device can be improved to attain potential applications for, for example, home electric appliances and illuminations.

1 Glass substrate
2 Transparent anode
3 Hole injection layer
4 First hole transport layer
5 Second hole transport layer
6 Light emitting layer
7 Electron transport layer
8 Electron injection layer
9 Cathode

The invention claimed is:

1. An organic electroluminescent device comprising at least an anode, a hole transport layer, a light emitting layer, an electron transport layer, and a cathode in this order, wherein the hole transport layer comprises an arylamine compound of the formula (1-1)

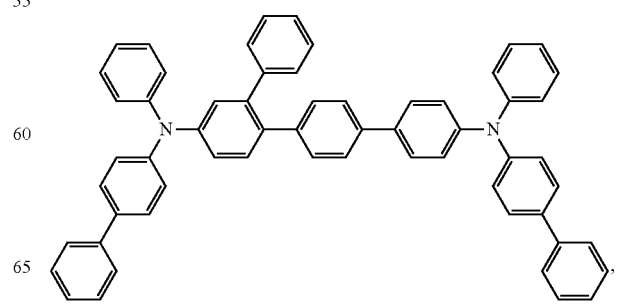

(1-2)
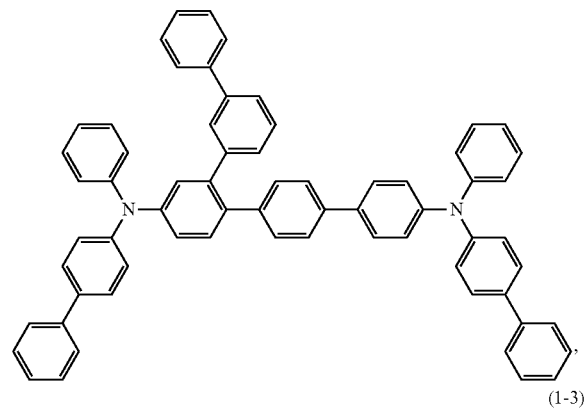
(1-7)
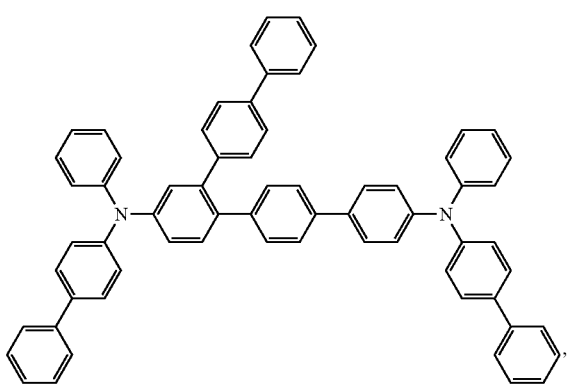
(1-3)
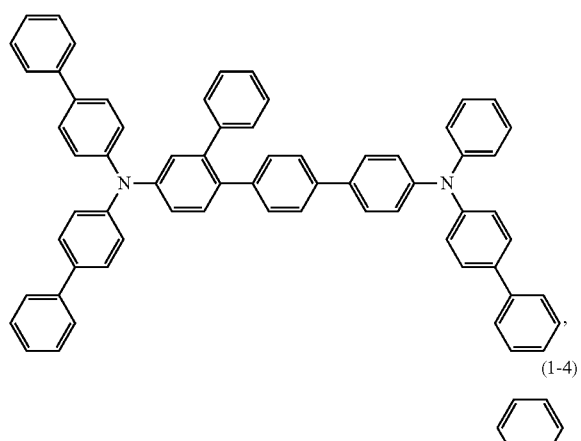
(1-8)
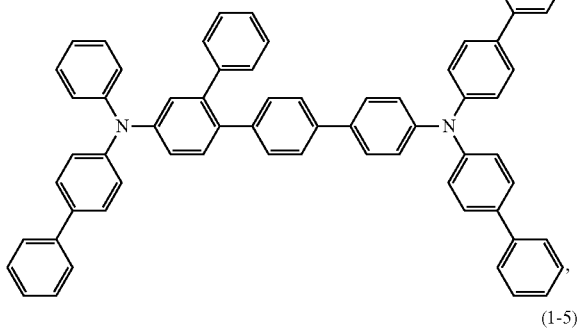
(1-4)
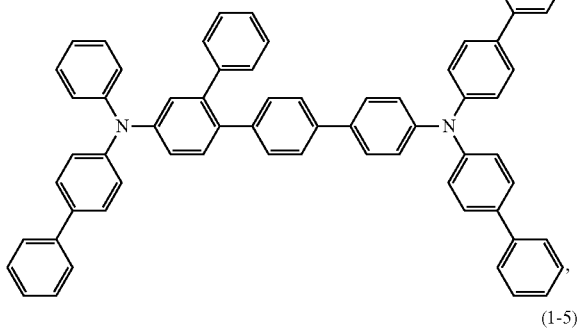
(1-5)
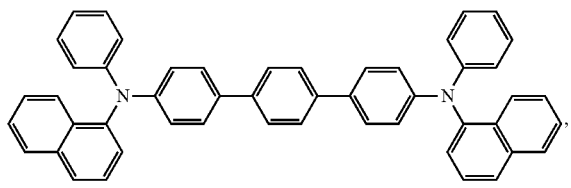
(1-9)
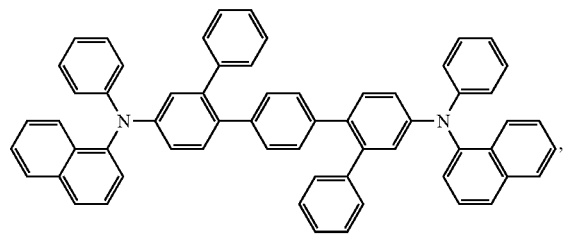
(1-6)
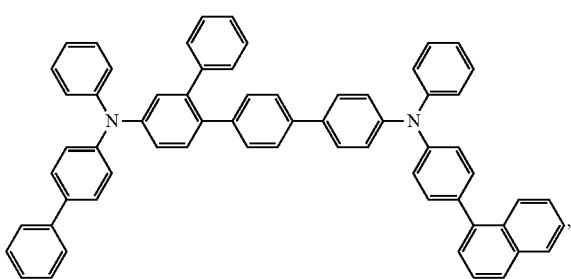
(1-10)
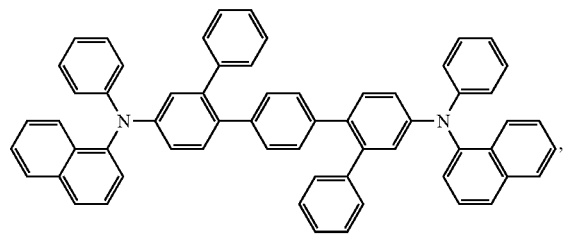

(1-11)
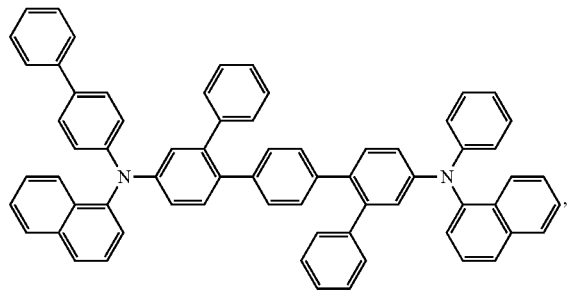
(1-12)
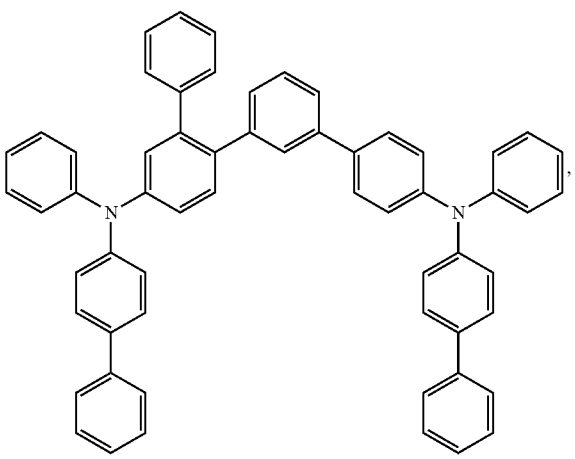
(1-13)
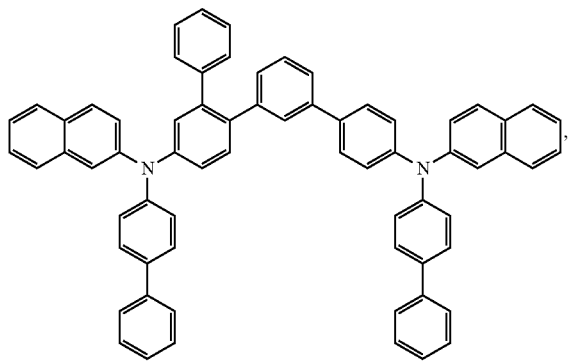
(1-14)
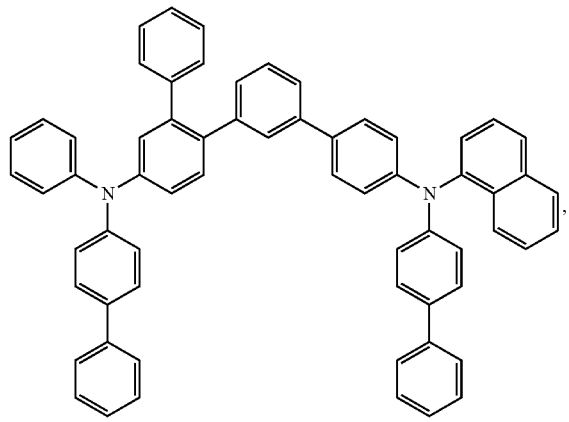
(1-15)
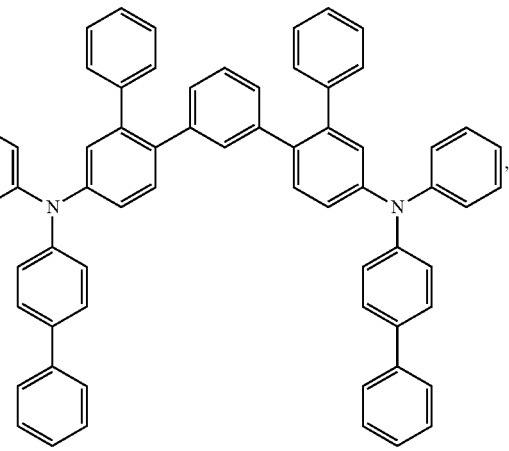
(1-16)
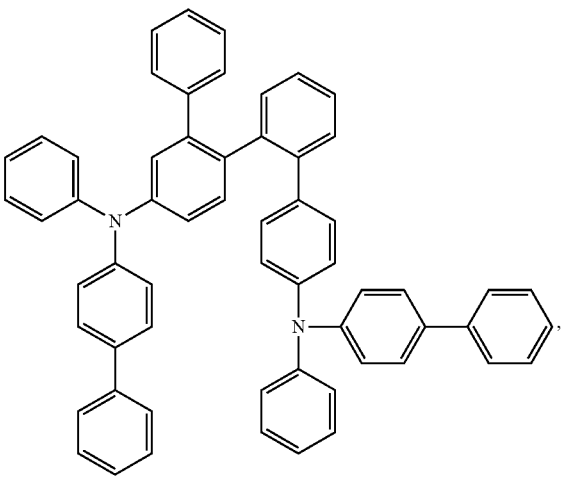
(1-17)
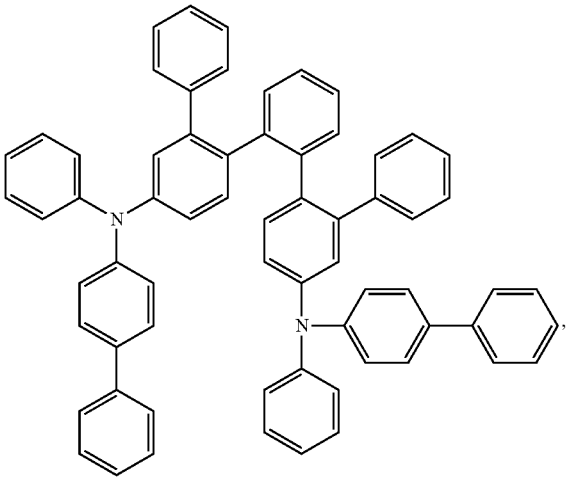

(1-18)
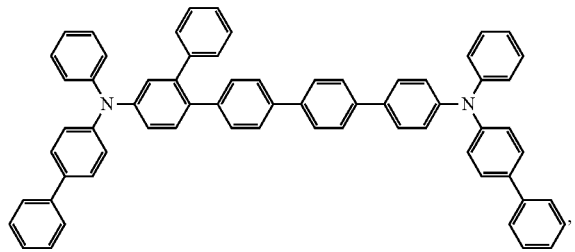
(1-19)
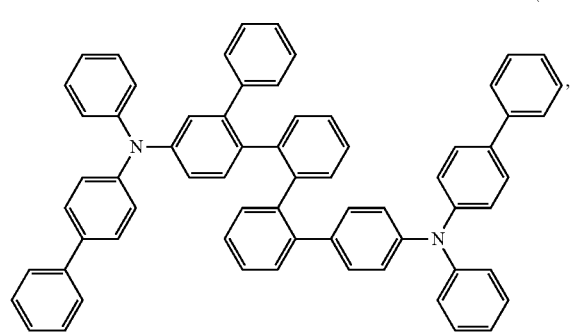
(1-20)
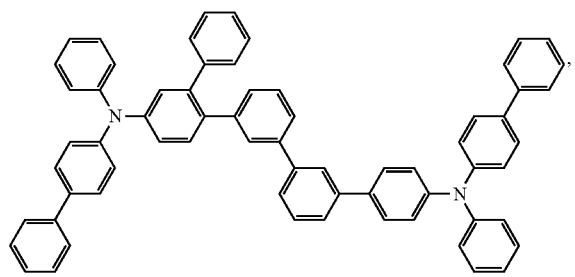
(1-21)
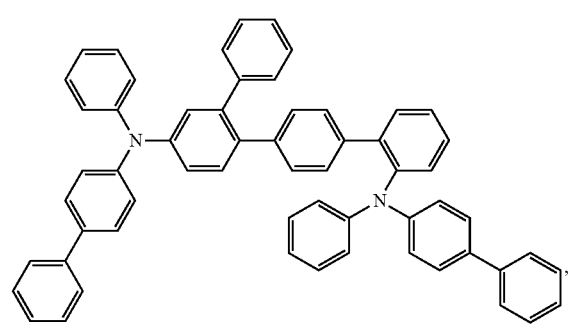
(1-22)
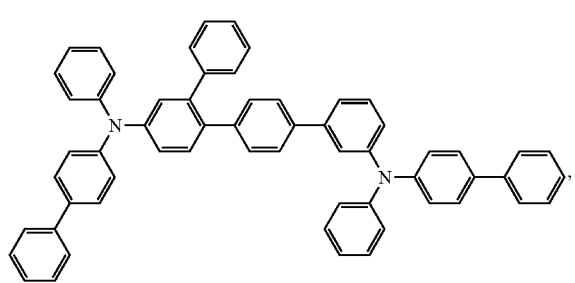
(1-23)
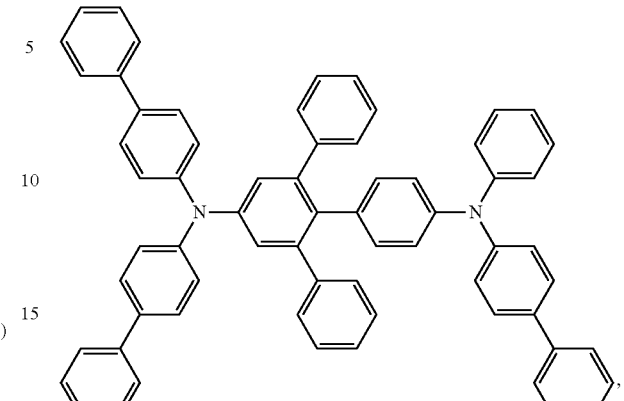
(1-24)
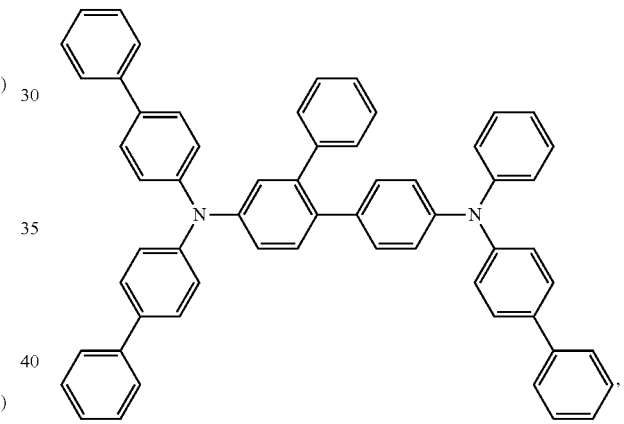
(1-25)
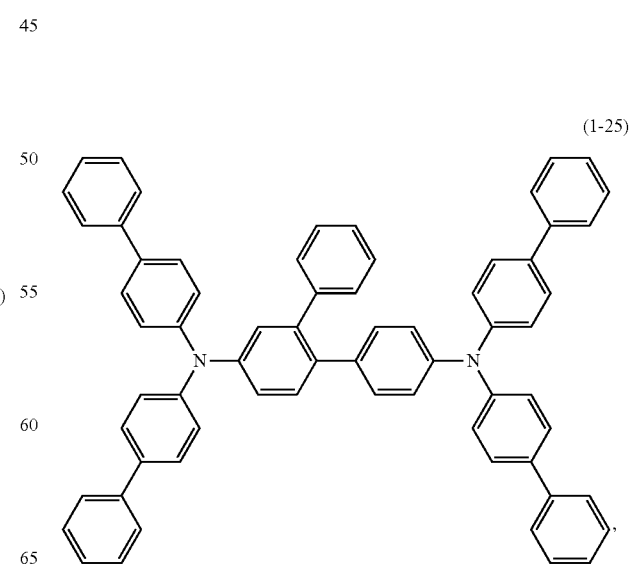

(1-26)
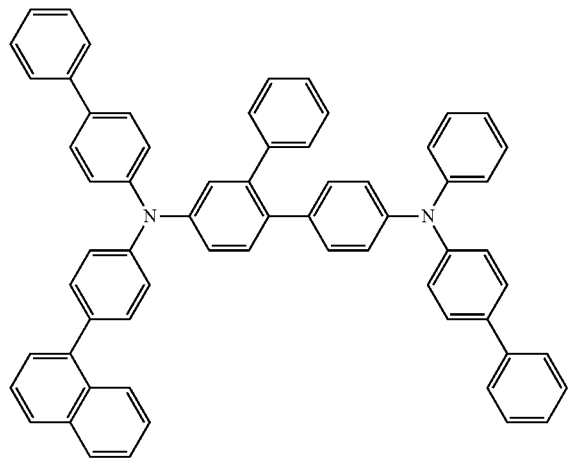
(1-27)
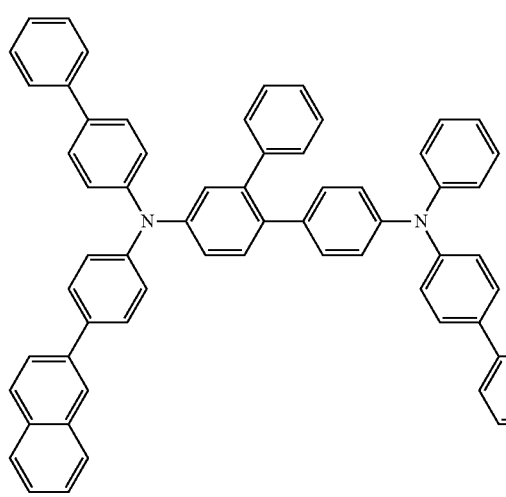
(1-28)
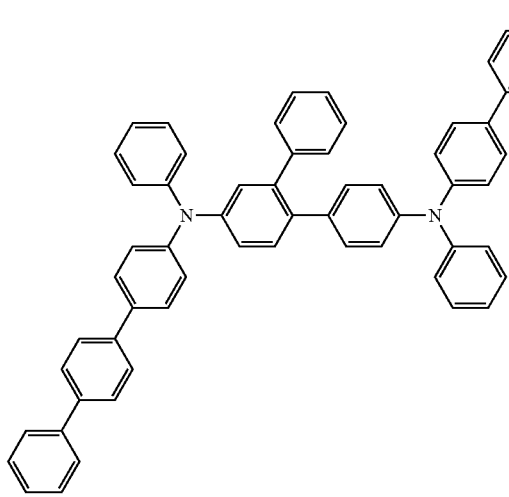
(1-29)
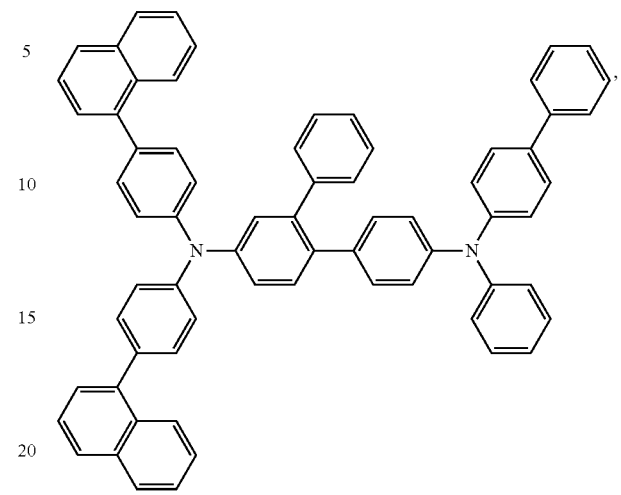
(1-30)
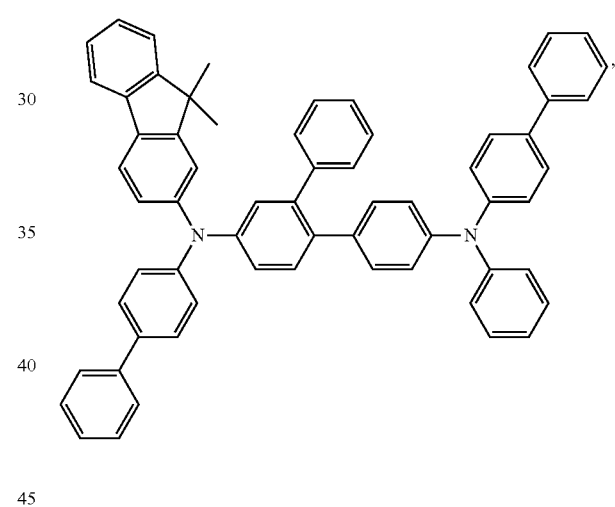
(1-31)
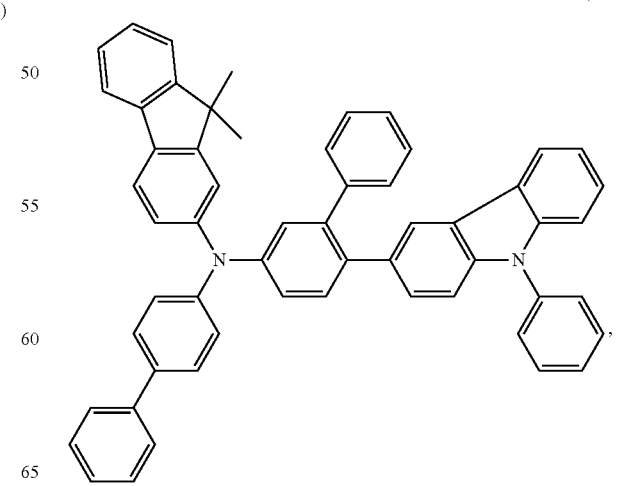

(1-32)
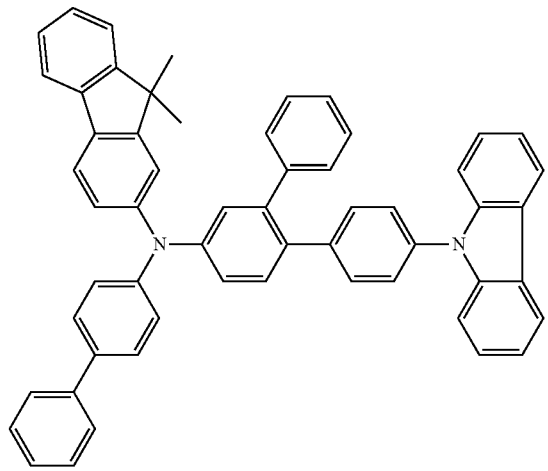
(1-33)
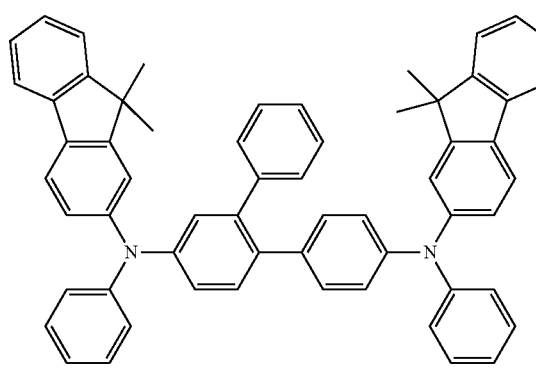
(1-34)
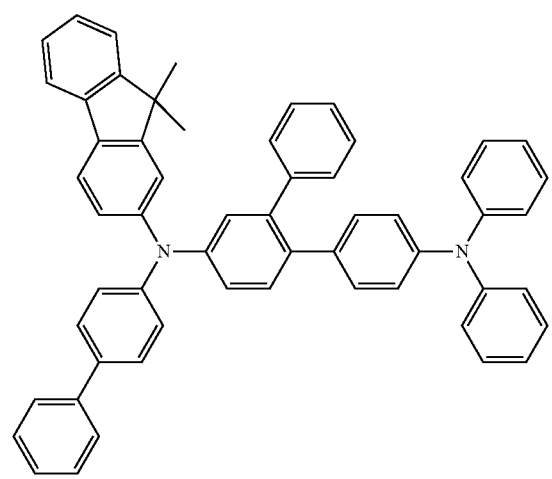
(1-35)
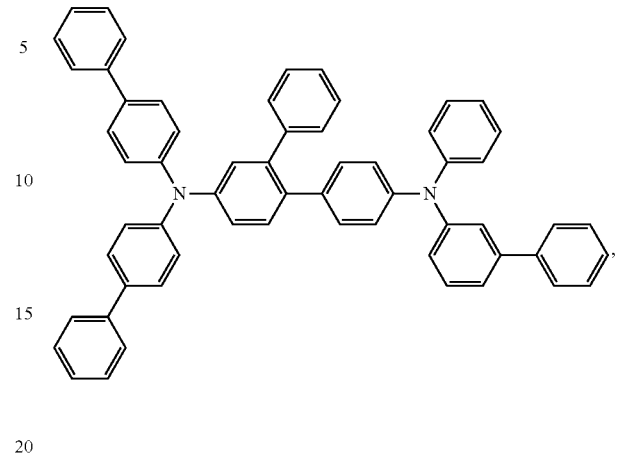
(1-36)
(1-37)
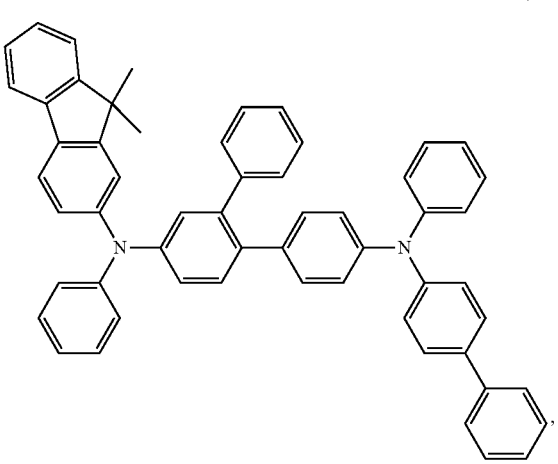

(1-38)

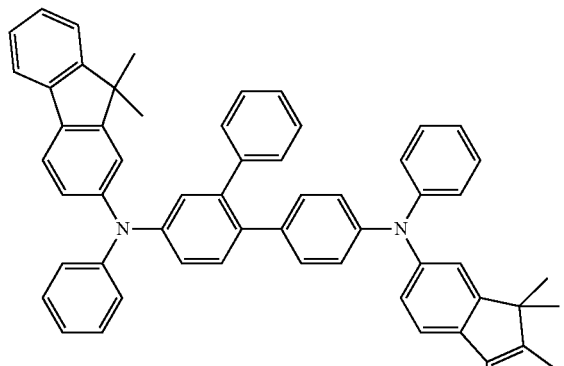

(1-39)

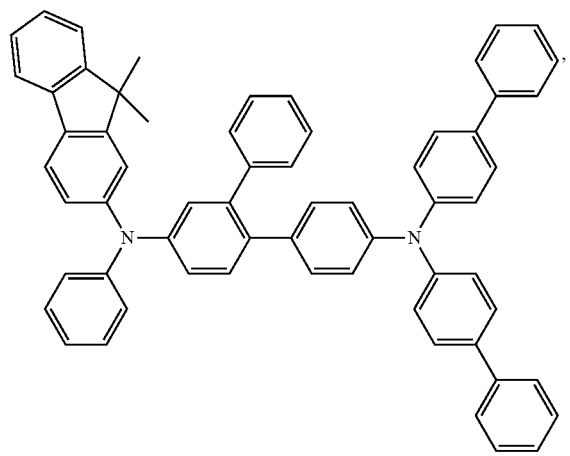

(1-40)

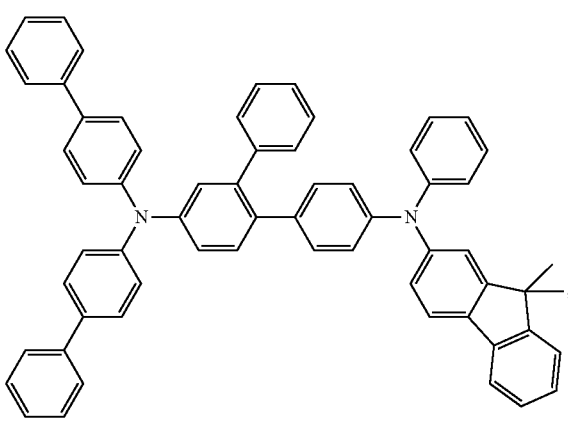

(1-41)

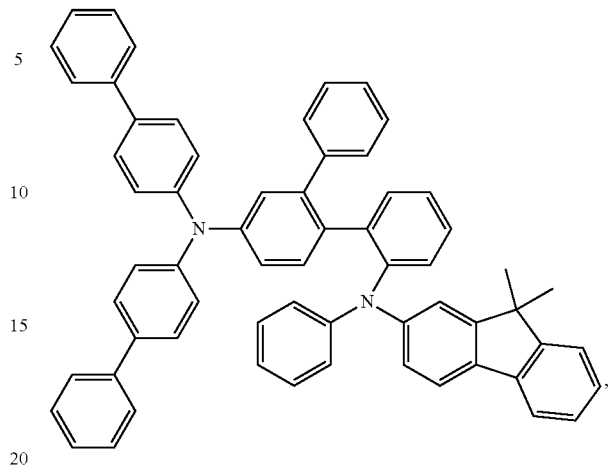

(1-42)

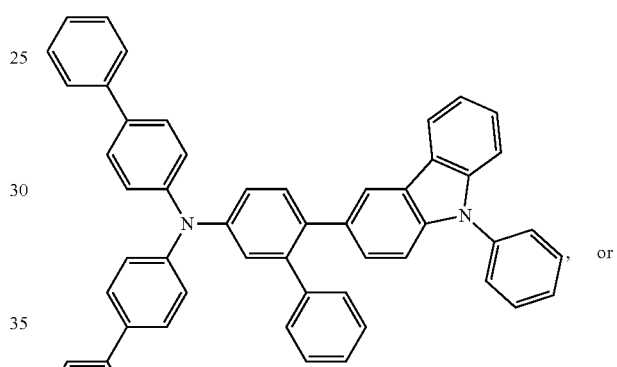

(1-43)

and wherein the hole transport layer has a two-layer structure of a first hole transport layer on the anode side and a second hole transport layer, and the second hole transport layer includes the arylamine compound of the formula (1-1) through (1-43).

2. The organic electroluminescent device according to claim 1, wherein the electron transport layer includes a compound of the following general formula (2) having a pyrimidine ring structure:

(2)

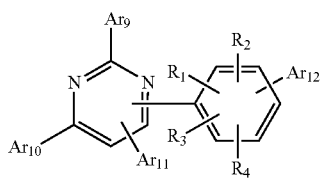

wherein, Ar₉ represents a substituted or unsubstituted aromatic hydrocarbon group or a substituted or unsubstituted condensed polycyclic aromatic group, and Ar₁₀ to Ar₁₁ may be the same or different, and represent a hydrogen atom, a substituted or unsubstituted aromatic hydrocarbon group or a substituted or unsubstituted condensed polycyclic aromatic group, and Ar₁₂ represents a substituted or unsubstituted aromatic heterocyclic group, and R₁ to R₄ may be the same or different, and represent a hydrogen atom, a deuterium atom, a fluorine atom, a chlorine atom, cyano, trifluoromethyl, linear or branched alkyl of 1 to 6 carbon atoms, a substituted or unsubstituted aromatic hydrocarbon group, a substituted or unsubstituted aromatic heterocyclic group, or a substituted or unsubstituted condensed polycyclic aromatic group, and Ar₁₀ and Ar₁₁ are not simultaneously a hydrogen atom.

3. The organic electroluminescent device according to claim 1, wherein the first hole transport layer includes a triphenylamine derivative different from the arylamine compound included in the second hole transport layer, and the triphenylamine derivative is a compound having a molecular structure containing two triphenylamine skeletons bonded to each other via a single bond or a divalent hydrocarbon group, and having 2 to 6 triphenylamine skeletons as a whole molecule.

4. The organic electroluminescent device according to claim 3, wherein the triphenylamine derivative contained in the first hole transport layer is a derivative of the following general formula (3):

(3)

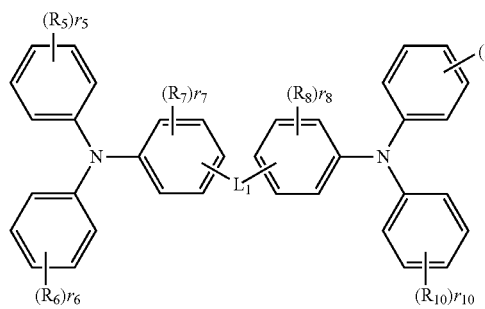

wherein, R₅ to R₁₀ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, and r₅ to r₁₀ may be the same or different, r₅, r₆, r₉ and r₁₀ representing 0 to 5, and r₇ and r₈ representing 0 to 4, and when r₅, r₆, r₉ and r₁₀ are 2 to 5, or when r₇ and r₈ are 2 to 4, R₅ to R₁₀, a plurality of which bind to the same benzene ring, may be the same or different and may bind to each other via a single bond, substituted or unsubstituted methylene, an oxygen atom, or a sulfur atom to form a ring, and L₁ represents a divalent group of the following structural formulas (C) to (G), or a single bond

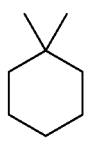
(C)

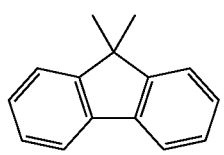
(D)

—CH₂— (E)

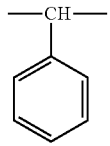
(F)

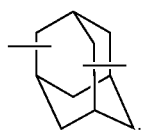
(G)

5. The organic electroluminescent device according to claim 3, wherein the triphenylamine derivative contained in the first hole transport layer is a derivative of the following general formula (4):

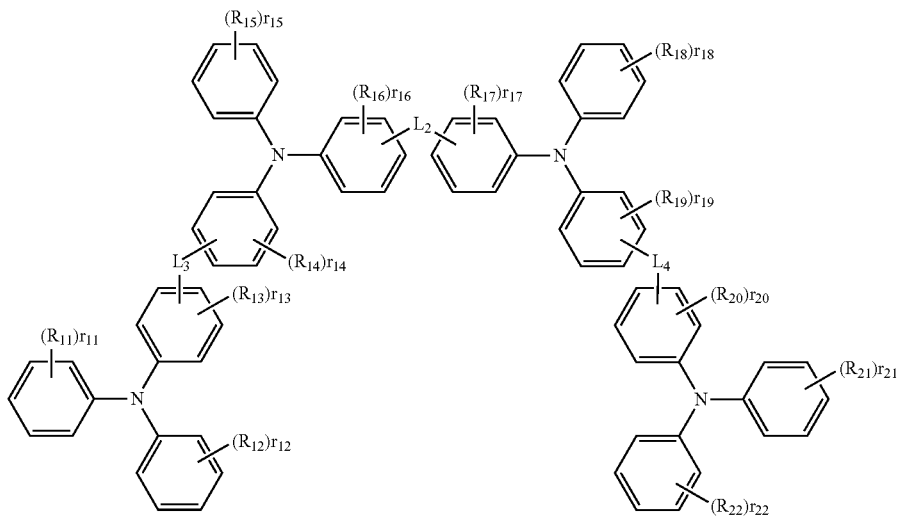

(4)

wherein, $R_{11}$ to $R_{22}$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, and $r_{11}$ to $r_{22}$ may be the same or different, $r_{11}$, $r_{12}$, $r_{15}$, $r_{18}$, $r_{21}$ and $r_{22}$ representing 0 to 5, and $r_{13}$, $r_{14}$, $r_{16}$, $r_{17}$, $r_{19}$ and $r_{20}$ representing 0 to 4, and when $r_{11}$, $r_{12}$, $r_{15}$, $r_{18}$, $r_{21}$ and $r_{22}$ are 2 to 5, or when $r_{13}$, $r_{14}$, $r_{16}$, $r_{17}$, $r_{19}$ and $r_{20}$ are 2 to 4, $R_{11}$ to $R_{22}$, a plurality of which bind to the same benzene ring, may be the same or different and may bind to each other via a single bond, substituted or unsubstituted methylene, an oxygen atom, or a sulfur atom to form a ring, and $L_2$, $L_3$ and $L_4$ may be the same or different, and represent a divalent group of the following structural formulas (B) to (G), or a single bond

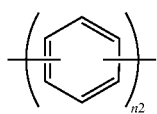

(B)

(In the formula, n2 represents 1 to 3)

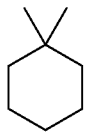

(C)

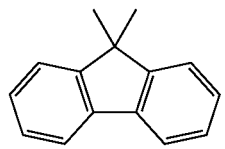

(D)

—CH$_2$—  (E)

—CH—  (F)

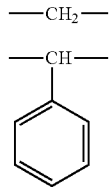

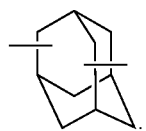

(G)

6. The organic electroluminescent device according to claim 1, wherein the light emitting layer includes a blue light emitting dopant.

7. The organic electroluminescent device according to claim 6, wherein the light emitting layer includes a blue light emitting dopant, which is a pyrene derivative.

8. The organic electroluminescent device according to claim 1, wherein the light emitting layer includes an anthracene derivative.

9. The organic electroluminescent device according to claim 8, wherein the light emitting layer includes a host material which is the anthracene derivative.

10. The organic electroluminescent device according to claim 2, wherein the light emitting layer includes a blue light emitting dopant.

11. The organic electroluminescent device according to claim 2, wherein the light emitting layer includes an anthracene derivative.

* * * * *